US009280718B2

(12) United States Patent
Claude et al.

(10) Patent No.: US 9,280,718 B2
(45) Date of Patent: Mar. 8, 2016

(54) SYSTEMS AND METHODS FOR AUTOMATED VOXELATION OF REGIONS OF INTEREST FOR MAGNETIC RESONANCE SPECTROSCOPY

(71) Applicant: NociMed, LLC, Redwood City, CA (US)

(72) Inventors: John P. Claude, Redwood City, CA (US); James C. Peacock, III, San Carlos, CA (US); Paul H. Kane, Albuquerque, NM (US)

(73) Assignee: Nocimed, LLC, Redwood City, CA (US)

( * ) Notice: Subject to any disclaimer, the term of this patent is extended or adjusted under 35 U.S.C. 154(b) by 133 days.

(21) Appl. No.: 13/830,632

(22) Filed: Mar. 14, 2013

(65) Prior Publication Data
US 2013/0230224 A1    Sep. 5, 2013

Related U.S. Application Data

(63) Continuation-in-part of application No. PCT/US2011/062137, filed on Nov. 23, 2011.

(60) Provisional application No. 61/417,182, filed on Nov. 24, 2010.

(51) Int. Cl.
G06K 9/00    (2006.01)
G06K 9/34    (2006.01)
(Continued)

(52) U.S. Cl.
CPC . G06K 9/34 (2013.01); A61B 5/055 (2013.01); G01R 33/485 (2013.01);
(Continued)

(58) Field of Classification Search
None
See application file for complete search history.

(56) References Cited

U.S. PATENT DOCUMENTS 4,983,920 A    1/1991   Lampman et al.
5,068,098 A    11/1991  Schweighardt et al.
(Continued)

FOREIGN PATENT DOCUMENTS

JP    S63-204143    8/1988
JP    H05-509162    12/1993
(Continued)

OTHER PUBLICATIONS
U.S. Appl. No. 14/625,918, filed Feb. 19, 2015, Peacock, III et al.
(Continued)

Primary Examiner — Bhavesh Mehta
Assistant Examiner — Oneal R Mistry
(74) Attorney, Agent, or Firm — Knobbe, Martens, Olson & Bear, LLP

(57) ABSTRACT

A system and method for automating an appropriate voxel prescription in a uniquely definable region of interest (ROI) in a tissue of a patient is provided, such as for purpose of conducting magnetic resonance spectroscopy (MRS) in the ROI. The dimensions and coordinates of a single three dimensional rectilinear volume (voxel) within a single region of interest (ROI) are automatically identified. This is done, in some embodiments by: (1) applying statistically identified ROI search areas within a field of view (FOV); (2) image processing an MRI image to smooth the background and enhance a particular structure useful to define the ROI; (3) identifying a population of pixels that define the particular structure; (4) performing a statistical analysis of the pixel population to fit a 2D model such as an ellipsoid to the population and subsequently fit a rectilinear shape within the model; (5) repetiting elements (1) through (4) using multiple images that encompass the 3D ROI to create a 3D rectilinear shape; (6) a repetition of elements (1) through (5) for multiple ROIs with a common FOV. A manual interface may also be provided, allowing for override to replace by manual prescription, assistance to identify structures (e.g. clicking on disc levels), or modifying the automated voxel (e.g. modify location, shape, or one or more dimensions).

19 Claims, 17 Drawing Sheets

(51) Int. Cl.
*A61B 5/055* (2006.01)
*G01R 33/485* (2006.01)
*G01R 33/54* (2006.01)
*G06T 7/00* (2006.01)

(52) U.S. Cl.
CPC .......... *G01R 33/543* (2013.01); *G06T 7/0083* (2013.01); *G06T 2207/10088* (2013.01); *G06T 2207/30012* (2013.01)

(56) References Cited

U.S. PATENT DOCUMENTS

| | | | |
|---|---|---|---|
| 5,201,311 | A | 4/1993 | Bottomley et al. |
| 5,207,715 | A | 5/1993 | Fossel |
| 5,270,651 | A | 12/1993 | Wehrli |
| 5,617,861 | A | 4/1997 | Ross et al. |
| 5,844,097 | A | 12/1998 | Cameron, Sr. et al. |
| 5,903,149 | A | 5/1999 | Gonen et al. |
| 6,018,675 | A | 1/2000 | Apkarian et al. |
| 6,069,478 | A | 5/2000 | Hurd |
| 6,278,891 | B1 | 8/2001 | Reiderman et al. |
| 6,472,871 | B2 | 10/2002 | Ryner |
| 6,552,541 | B2 | 4/2003 | Nauerth |
| 6,617,169 | B2 | 9/2003 | Ke et al. |
| 6,639,405 | B2 | 10/2003 | Liu et al. |
| 6,674,282 | B2 | 1/2004 | Pines et al. |
| 6,683,455 | B2 | 1/2004 | Ebbels et al. |
| 6,686,348 | B2 | 2/2004 | De Nanteuil et al. |
| 6,835,572 | B1 | 12/2004 | Mountford et al. |
| 6,836,114 | B2 | 12/2004 | Reddy et al. |
| 6,943,033 | B2 | 9/2005 | Van Zijl et al. |
| 6,987,997 | B1 | 1/2006 | Hurd et al. |
| 7,042,214 | B2 | 5/2006 | Cunningham et al. |
| 7,116,104 | B2 | 10/2006 | Reddy et al. |
| 7,181,348 | B2 | 2/2007 | Wishart et al. |
| 7,184,813 | B1 | 2/2007 | Hurd et al. |
| 7,288,521 | B2 | 10/2007 | Franco |
| 7,319,784 | B2 | 1/2008 | Ryner et al. |
| 7,323,871 | B2 | 1/2008 | Foo |
| 7,411,396 | B1 | 8/2008 | Schirmer et al. |
| 7,676,254 | B2 | 3/2010 | Siddall et al. |
| 7,705,596 | B2 | 4/2010 | Witschey et al. |
| 7,749,275 | B2 * | 7/2010 | Lambrecht .......... A61B 5/1076 606/279 |
| 8,076,936 | B2 | 12/2011 | Borthakur et al. |
| 8,208,709 | B2 | 6/2012 | Ding et al. |
| 8,344,728 | B2 | 1/2013 | Majumdar et al. |
| 8,761,860 | B2 | 6/2014 | Peacock, III et al. |
| 8,798,351 | B2 | 8/2014 | Ding et al. |
| 8,825,131 | B2 | 9/2014 | Peacock, III et al. |
| 2001/0003423 | A1 | 6/2001 | Wald |
| 2002/0037251 | A1 | 3/2002 | Driehuys |
| 2004/0006376 | A1 | 1/2004 | Falci |
| 2004/0214348 | A1 | 10/2004 | Nicholson et al. |
| 2005/0024051 | A1 | 2/2005 | Doddrell et al. |
| 2005/0054910 | A1 | 3/2005 | Tremblay et al. |
| 2005/0240104 | A1 | 10/2005 | Shim et al. |
| 2005/0251025 | A1 | 11/2005 | Hancu et al. |
| 2007/0167729 | A1 | 7/2007 | Mistretta et al. |
| 2007/0253910 | A1 | 11/2007 | Ahrens et al. |
| 2008/0220530 | A1 | 9/2008 | Bahn et al. |
| 2008/0226148 | A1 * | 9/2008 | Gu et al. ................. 382/128 |
| 2009/0030308 | A1 | 1/2009 | Bradford et al. |
| 2009/0076481 | A1 | 3/2009 | Stegmann et al. |
| 2009/0134869 | A1 | 5/2009 | Lee |
| 2009/0191131 | A1 | 7/2009 | Fossheim et al. |
| 2009/0261823 | A1 | 10/2009 | Yu et al. |
| 2010/0086185 | A1 | 4/2010 | Weiss |
| 2010/0166278 | A1 | 7/2010 | Witschey |
| 2010/0244834 | A1 * | 9/2010 | Mori et al. .............. 324/310 |
| 2010/0264920 | A1 | 10/2010 | Witschey et al. |
| 2010/0268225 | A1 | 10/2010 | Coe et al. |
| 2011/0087087 | A1 * | 4/2011 | Peacock et al. .......... 600/410 |
| 2011/0230755 | A1 | 9/2011 | MacFarlane et al. |
| 2012/0155731 | A1 * | 6/2012 | Weersink et al. ........ 382/131 |
| 2013/0144155 | A1 | 6/2013 | Majumdar et al. |
| 2014/0064586 | A1 | 3/2014 | Peacock, III et al. |
| 2015/0112183 | A1 | 4/2015 | Peacock, III et al. |
| 2015/0119688 | A1 | 4/2015 | Peacock, III et al. |

FOREIGN PATENT DOCUMENTS

| | | |
|---|---|---|
| JP | H06-503418 | 4/1994 |
| JP | 2003524490 | 8/2003 |
| JP | 2004526130 | 8/2004 |
| JP | 2004528559 | 9/2004 |
| WO | WO 2006/081471 | 8/2006 |
| WO | WO 2007/035906 | 3/2007 |
| WO | WO 2009/058915 | 5/2009 |
| WO | WO 2009/148550 | 12/2009 |
| WO | WO 2011/060237 | 5/2011 |
| WO | WO 2012/071566 | 5/2012 |

OTHER PUBLICATIONS

Bartels, E.M., J.C. Fairbank, et al. (1998) "Oxygen and lactate concentrations measured in vivo in the intervertebral discs of patients with scoliosis and back pain." Spine 23 (1): 1-7; discussion 8.

Bottomley PA. "Spatial localization in NMR spectroscopy in vivo." Ann N Y Acad Sci 1987; 508:333-348.

Brown TR, Kincaid BM, Ugurbil K. "NMR chemical shift imaging in three dimensions." Proc. Natl. Acad. Sci. USA 1982; 79:3523-3526.

Brown, M.F., M.V. Hukkanen, et al. (1997). "Sensory and sympathetic innervation of the vertebral endplate in patients with degenerative disc disease." J Bone Joint Surg Br 79(1):147-53.

Buenaventura, R.M., R.V. Shah, et al. (2007). "Systematic review of discography as a diagnostic test for spinal pain: an update." Pain Physician 10(1): 147-64.

Carragee et al., "2009 ISSLS Prize Winner: Does Discography Cause Accelerated Progression of Degeneration Changes in the Lumbar Disc," Spine vol. 34, No. 21, pp. 2338-2345, 2009.

Carragee, E. J., T. Lincoln, et al. (2006). "A gold standard evaluation of the "discogenic pain" diagnosis and determined by provocative discography." Spine 31(18): 2115-23.

Carragee, E.J. and T.F. Alamin (2001). "Discography, a review." Spine J 1(5): 364-72.

Carragee, E.J., T.F. Alamin, et al. (2006). "Low-pressure positive Discography in subjects asymptomatic of significant low back pain illness." Spine 31(5): 505-9.

Cohen, S.P., T.M. Larkin, et al. (2005). "Lumbar discography: a comprehensive review of outcome studies, diagnostic accuracy, and principles." Reg Anesth Pain Med 30(2): 163-83.

Coppes, M.H., E. Marani, et al. (1997). "Innervation of "painful" lumbar discs." Spine 22(20):2342-9; discussion 2349-50.

Cunningham CH, Vigneron DB, Chen AP, Xu D, Hurd RE, Sailasuta N, Pauly JM. "Design of symmetric-sweep spectral-spatial RF pulses for spectral editing." Magn Reson Med 2004; 52: 147-153.

Derby, R., R.M. Baker, et al. (2008). "Analgesic Discography: Can Analgesic Testing Identify a Painful Disc?" SpineLine (November-December): 17-24.

Diamant, B., J. Karlsson, et al. (1968). "Correlation between lactate levels and pH in discs of patients with lumbar rhizopathies." Experientia 24(12): 1195-6.

Jiru, F., "Introduction to Post-Processing Techniques," Europeant Journal of Radiology 67, (2008) 202-217.

Frahm J, Bruhn H, Gyngell ML, Merboldt KD, Hanicke W, Sauter R. "Localized high-resolution proton NMR spectroscopy using stimulated echoes: initial applications to human brain in vivo." Magn Reson Med 1989; 9:79-93.

Freemont, A.J., A. Watkins, et al. (2002). "Nerve growth factor expression and innervation of the painful intervertebral disc." J Pathol 197(3): 286-92.

Freemont, A.J., T.E. Peacock, et al. (1997). "Nerve ingrowth into diseased intervertebral disc in chronic back pain." Lancet 350(9072): 178-81.

Grunhagen, T., G. Wilde, et al. (2006). "Nutrient supply and intervertebral disc metabolism." J Bone Joint Surg Am 88 Suppl 2: 30-5.

(56) References Cited

OTHER PUBLICATIONS

Guyer, R.D. and D.D. Ohnmeiss (2003). "Lumbar discography." Spine J 3(3 Suppl): 11S-27S.
Immke, D. C. and E.W. McCleskey (2001). "Lactate enhances the acid-sensing Na+ channel on ischemia-sensing neurons." Nat Neurosci 4(9): 869-70.
Ishihara, H. and J.P. Urban (1999). "Effects of low oxygen concentrations and metabolic inhibitors on proteoglycan and protein synthesis rates in the intervertebral disc." J Orthop Res 17(6): 829-35.
Jain, A., S.M Brady-Kalnay, et al. (2004). "Modulation of Rho GTPase activity alleviates chondroitin sulfate proteoglycan-dependent inhibition of neurite extension." J Neurosci Res 77(2): 299-307.
Jones, L.L., D. Sajed, et al. (2003). "Axonal regeneration through regions of chondroitin sulfate proteoglycan deposition after spinal cord injury: a balance of permissiveness and inhibition." J Neurosci 23(28): 9276-88.
Keshari, K. R., A. S. Zektzer, et al. (2005). "Characterization of intervertebral disc degeneration by high-resolution magic angle spinning (HR-MAS) spectroscopy." Magn Reson Med 53(3): 519-27.
Keshari, K.R., J.C. Lotz, et al. (Dec. 1, 2005). "Correlation of HR-MAS spectroscopy derived metabolite concentrations with collagen and proteoglycan levels and Thompson grade in the degenerative disc." Spine 30(23): 2683-88.
Keshari, K.R., J.C. Lotz, et al. (2008). "Lactic acid and proteoglycans as metabolic markers for discogenic back pain." Spine 33(3): 312-317.
Klapka, N. and H. W. Muller (2006). "Collagen matrix in spinal cord injury." J Neurotrauma 23(3-4): 422-35.
Molliver, D. C., D. C. Immke, et al. (2005). "ASIC3, an acid-sensing ion channel, is expressed in metaboreceptive sensory neurons." Mol Pain 1: 35.
Nachemson, A. (1969). "Intradiscal measurements of pH in patients with lumbar rhizopathies." Acta Orthop Scand 40(1): 23-42.
Naves, L. A. and E. W. McCleskey (2005). "An acid-sensing ion channel that detects ischemic pain." Braz J Med Biol Res 38(11): 1561-9.
O'Neill, C. and M. Kurgansky (2004). "Subgroups of positive discs on discography." Spine 29(19): 2134-9.
Pauly J, Le Roux P, Nishimura D, Macovski A. "Parameter relations for the Shinnar-Le Roux selective excitation pulse design algorithm [NMR imaging]." IEEE Trans Med Imaging 1991; 10: 53-65.
Properzi, F., R. A. Asher, et al. (2003). "Chondroitin sulphate proteoglycans in the central nervous system: changes and synthesis after injury." Biochem Soc Trans 31(2): 335-6.
Roberts, S., H. Evans, et al. (2006). "Histology and pathology of the human intervertebral disc." J Bone Joint Surg Am 88 Suppl 2: 10-4.
Roughley, P. J., M. Alini, et al. (2002). "The role of proteoglycans in aging, degeneration and repair of the intervertebral disc." Biochem Soc Trans 30(Pt 6): 869-74.
Rukwied, R., B. A. Chizh, et al. (2007). "Potentiation of nociceptive responses to low pH injections in humans by prostaglandin E2." J Pain 8(5): 443-51.
Scuderi, G. J., G. V. Brusovanik, et al. (2008). "A critical evaluation of discography in patients with lumbar intervertebral disc disease." Spine J 8(4): 624-9.
Star-Lack J, Nelson SJ, Kurhanewicz J, Huang LR, Vigneron DB. "Improved water and lipid suppression for 3D PRESS CSI using RF bank selective inversion with gradient dephasing (BASING)." Magn Reson Med 1997; 38: 311-321.
Sutherland, S. P., C. J. Benson, et al. (2001). "Acid-sensing ion channel 3 matches the acid-gated current in cardiac ischemia-sensing neurons." Proc Natl Acad Sci U S A 98(2): 711-6.
Urban, J. P., S. Smith, et al. (2004). "Nutrition of the intervertebral disc." Spine 29(23): 2700-9.
Wichman, H. J. (2007). "Discography: over 50 years of controversy." Wmj 106(1): 27-9.
Wolfer, L. R., R. Derby, et al. (2008). "Systematic review of lumbar provocation discography in asymptomatic subjects with a meta-analysis of false-positive rates." Pain Physician 11(4):513-38.
Zuo, J., D. Neubauer, et al. (1998). "Degradation of chondroitin sulfate proteoglycan enhances the neurite-promoting potential of spinal cord tissue." Exp Neurol 154(2): 654-62.
Zuo, J., Y. J. Hernandez, et al. (1998). "Chondroitin sulfate proteoglycan with neurite-inhibiting activity is up-regulated following peripheral nerve injury." J Neurobiol 34(1): 41-54.
Haro, H. et al. "Matrix metalloproteinase-7-dependent release of tumor necrosis factor in a model of herniated disc resorption," Jour. of Clinical Inv., vol. 105, No. 2, Jan. 2000, pp. 143-150.
Mow, V.C. et al. "Basic Orthopaedic Biomechanics—Chapter 10—Bomechanics of the Human Spine," 1997, pp. 353-393.
Thompson, J. et al. "Preliminary Evaluation of a Scheme for Grading the Gross Morphology of the Human Intervertebral Disc," Spine, vol. 15, 1990, pp. 411-415.
Iatridis, J. et al. "Alterations in the Mechanical Behavior of the Human Lumbar Nucleas Pulposus with Degeneration and Aging," Jour. of Ortho Research, vol. 15, 1997, pp. 318-322.
Beall, et al. "NMR Data Handbook for Biomedical Applications," New York, Pergamon Press, 1984, 11 pages.
Boos, N. et al.—Quantitative Magnetic Resonance Imaging of the Lumbar Spine, Spine, vol. 20, No. 21, pp. 2358-2366.
Bottomley, P. et al. "A review of normal tissue hydrogen NMR relaxation times and relaxation mechanisms from 1-100 MHz: Dependence on tissue type, NMR frequency, temperature, species, excision and age," Med. Phys., vol. 11, No. 4, Jul./Aug. 1984, pp. 425-448.
Lyons, G. et al. "Biochemical Changes in Intervertebral Disc Degeneration," Biochimica Biophys Acta, vol. 673, 1981, pp. 443-453.
Maroudas, A.—"The Biology of the Intervertebral Disc"—In: Ghosh, P. el. The Biology of the Intervertebral Disc, vol. II, Chapter 9, 1988.
Pearce, R. et al.—"Degeneration and the Chemical Composition of the Human Lumbar Intervertebral Disc"—Jour. of Ortho. Research, vol. 5, 1987, pp. 198-205.
Tertii, M. et al.—"Disc Degeneration in Magnetic Resonance Imaging: A Comparative Biochemical, Histologic, and Radiologic Study in Cadaver Spines"—Spine, 1991, pp. 629-634.
Chiu, E. et al.—"Magnetic Resonance Imaging Measurement of Relaxation and Water Diffusion in the Human Lumbar Intervertebral Disc Under Compression in Vitro"—Spine, vol. 26, No. 19, 2001, pp. E437-E444.
Gundry, C. et al.—"Magnetic Resonance Imaging of the Musculoskeletal System, Part 8. The Spine, Section 1", Clinical Ortho. and Related Research, vol. 338, May 1997, pp. 275-287.
Gunzburg, R. et al.—"A Cadaveric Study Comparing Discography, Magnetic Resonance Imaging, Histology, and Mechanical Behavior of the Human Lumbar Disc"—Spine, 1991, pp. 417-423.
Modic, M. et al.—"Magnetic Resonance Imaging of Intervertebral Disk Disease"—Radiology, vol. 152, 1984, pp. I03-111.
Modic, M. et al.—"Lumbar Herniated Disk Disease and Canal Stenosis: Prospective Evaluation by Surface Coil MR, CT, and Myelography"—AJR, vol. 147, Oct. 1986, pp. 757-765.
Modic, M. et al.—"Imaging of Degenerative Disk Disease"—Radiology, vol. 168, 1988, pp. 177-186.
Sether, L. et al.—"Intervertebral Disk: Normal Age-related Changes in MR Signal Intensity"—Radiology, vol. 177, 1990, pp. 385-388.
Pfirrmann, C. et al.—"Magnetic Resonance Classification of Lumbar Intervertebral Disc Degeneration"—Spine, vol. 26, No. 17, pp. 1873-1878.
Nieminen, M. et al.—"Spatial Assessment of Articular Cartilage Proteoglycans with Gd-DTPA-Enhanced TI Imaging"—Mag. Res. in Med., vol. 48, 2002, pp. 640-648.
Mosher, T. et al.—"Human Articular Cartilage: Influence of Aging and Early Symptomatic Degeneration on the Spatial Variation of T2-Preliminary Findings at 3 TI"—Radiology, vol. 214, 2000, pp. 259-266.
Burstein, D. et al.—"Diffusion of Small Solutes in Cartilage as Measured by Nuclear Magnetic Resonance (NMR) Spectroscopy and Imaging"—Jour. of Ortho. Res., vol. 11, 1993, pp. 465-478.
Abdulkarim, J. et al.—"Magnetic Resonance Imaging of the Cervical Spine: Frequency of Degenerative Changes in the Intervertebral Disc With Relation to Age"—Clinical Radiology, vol. 58, 2003, pp. 980-984.

(56) References Cited

OTHER PUBLICATIONS

Swanson, M. et al.—"Proton HR-MAS Spectroscopy and Quantitative Pathologic Analysis of MRI/3D-MRSI-Targeted Postsurgical Prostate Tissues"—Mag. Resonance in Med., vol. 54, 2003, pp. 944-954.
Schiller, J., et al. "H and C-13 HR-MAS NMR Investigations on Native and Enzymatically Digested Bovine Nasal Certilage." Magnetic Resonance Materials in Physics 2001; 13:19-27.
Carr, H. et al.—"Effects of Diffusion on Free Precession in Nuclear Magnetic Resonance Experiments"—Phys. Review, vol. 94, No. 3, May 1, 1954, pp. 630-638.
Kupce, E.—"Applications of Adiabatic Pulses in Biomolecular Nuclear Magnetic Resonance"—Methods in Enzymology, vol. 338, 2001, pp. 82-111.
Mucci, A. et al.—"1 Hand 13C nuclear magnetic resonance identification and characterization of components of chondroitin sulfates of various origin"—Carbohydrate Polymers, vol. 41, 2003, pp. 37-45.
Groupille, P. et al.—"Matrix Metalloproteinases: The Clue to Intervertebral Disc Degeneration?"—Spine, vol. 23, No. 14, Jul. 1998, pp. 1612-1626.
Kang, J. et al.—"Towards a Biochemical Understanding of Human Intervertebral Disc Degeneration and Herniation: Contributions of Nitric Oxide, Interleukins, Prostaglandin E2, and Matrix Metalloproteinases"—spine, vol. 22, No. 10, May 15, 1997, pp. 1065-1073.
Weiler, C. et al.—"2002 SSE Award Competition in Basic Science: Expression of major matrix metalloproteinases is associated with intervertebral disc degradation and resorption"—Eur. Spine Jour., vol. 11, 2002, pp. 308-320.
Urban, J. et al.—"The Nucleus of the Intervertebral Disc from Development to Degeneration"—American Zoologist, vol. 40, No. 1, Feb. 2000, pp. 53-61.
Weidenbaum, M. et al.—"Correlating Magnetic Resonance Imaging with the Biochemical Content of the Normal Human Intervertebral Disc"—Jour. of Ortho. Research, vol. 10, 1992, pp. 552-561.
Boos, N. et al.—"Quantitative MR Imaging of Lumbar Intervertebral Disks and Vertebral Bodies: Influence of Diurnal Water Content Variations"—Radiology, vol. 188, 1993, pp. 351-354.
Boos, N. et al.—"Quantitative MR Imaging of Lumbar Intervertebral Discs and Vertebral Bodies: Methodology, Reproducibility, and Preliminary Results"—Mag. Res. Imaging, vol. 12, No. 4, 1994, pp. 577-587.
Keshari, K et al.—Poster and Abstract—"Identification of Chondroitin Sulfate as a Marker for Human Intervertebral disc Degeneration Using Proton High Resolution Magic Angle Spinning *HR-MAS) Spectroscopy"—The 44th ENC, Mar. 30-Apr. 4, 2003, 22 pages.
Majumdar, S.—Abstract—"Spectroscopic Markers of Disc Degeneration."—downloaded from CRISP website Nov. 23, 2004, 2 pages.
Petrantonaki, M., et al. "MRI Techniques for the Examination of Trabecular Bone Structure." Current Medical Imaging Reviews 2005, 1:35-41.
Ford, J. C., et al. "In Vivo Quantitative Characterization of Trabecular Bone by NMR Interferometry and Localized Proton Spectroscopy." Magnetic Resonance in Medicine 1991; 17: 543-551.
Schiller, J., et al. "Evaluation of Cartilage Composition and Degradation by High-Resolution Magic-Angle Spinning Nuclear Magnetic Resonance." Methods in Molecular Medicine 2004; 101:267-285.
Chung, C. T., et al. "Single photon emission computed tomography (SPECT) for low back pain induced by extension with no root sign." J. Chin. Med. Assoc. vol. 67, pp. 349-354 (2004).
Lusins, J. O., et al. "SPECT and lumbar MRI in back pain with emphasis on changes in end plates in association with disc degeneration (abstract)." J. Neuroimaging, vol. 8, No. 2, pp. 78-82 (1998).
McDonald, M., et al. "Use of computer tomography—single-photon emission computed tomography fusion for diagnosing painful facet arthropathy." Neurosurg. Focus, vol. 22, No. 1, E2 (2007).
Mulconrey, D. S., et al. "Interobserver reliability in the interpretation of diagnostic lumbar MRI and Nuclear imaging." The Spine Journal, vol. 6, pp. 177-184 (2006).

Keshari, K., et al. "Potential metabolic markers for intervertebral disc pain." Proc. Intl. Soc. Mag. Reson. Med. 14, p. 1710. May 9, 2006.
Savvopoulou, V., et al. "Degenerative Endplate Changes of the Lumbosacral Spine: Dynamic Contrast-Enhanced MRI Profiles Related to Age, Sex, and Spinal Level." Journal of Magnetic Resonance Imaging 33:382-389 (2011).
Hassler, O. "The Human Intervertebral Disc: A Micro-Angiographical Study on Its Vascular Supply at Various Ages." Acta Orthop. Scandinay. 40, 765-772, 1970.
Niinimaki, J., et al. "Association of lumbar artery narrowing, degenerative changes in disc and endplate and apparent diffusion in disc on postcontrast enhancement of lumbar intervertebral disc." Magn. Reson. Mater Phy. 22:101-109 (2009).
Rajasekaran, S., et al. "ISSLS Prize Winner: A Study of Diffusion in Human Lumbar Discs: A Serial Magnetic Resonance Imaging Study Documenting the Influence of the Endplate on Diffusion in Normal and Degenerate Discs." Spine vol. 29, No. 23, pp. 2654-2667 (2004).
Liu, Y., et al. "Intervertebral Disk Degeneration Related to Reduced Vertebral Marrow Perfusion at Dynamic Contrast-Enhanced MRI." AJR:192: 974-979, Apr. 2009.
Bolan, Patrick J., et al., "Measurement and Correction of Repiration-Induced Bo Variations in Breast 1H MRS at 4 Tesla," Magnetic Resonance in Medicine 52:000-000 (2004).
Lorenz, C., et al. "3D Statistical Shape Models for Medical Image Segmentation," pp. 414-423, Second International Conference on 3-D Imaging and Modeling (3DIM '99), 1999.
Lin C S et al: "2D CSI proton MR spectroscopy of human spinal vertebra: feasibility studies.", Journal of Magnetic Resonance Imaging : JM RI Mar. 2000, vol. II, No. 3, Mar. 2000, pp. 287-293.
"Spectroscopy reconstruction" and "Spectroscopy processing" In: "Intera Spectroscopy—Instructions for Use", Jul. 2002, Philips Medical Systems, Netherlands, pp. 6-1 to 7-6.
Dubey P. et al.: "Proton MR Spectroscopic Imaging of the Human Cervical Spine at 3 Tesla", Proceedings of the International Society for Magnetic Resonance in Medicine, 13th Meeting Proceedings, May 7, 2005, p. 812.
Majumdar, "Review Article Magnetic resonance imaging and spectroscopy of the intervertebral disc," NMR in Biomed (2006) 19: 894-903.
Carragee et al., "Prospective Controlled Study of the Development of Lower Back Pain in Previously Asymptomatic Subjects Undergoing Experimental Discography." Spine vol. 29, No. 10, pp. 1112-1117 (2004).
Carrino et al., "Prospective evaluation of contrast-enhanced MR imaging after uncomplicated lumbar discography." Skeletal Radiol (2007) 36:293-299.
Derincek et al., "Discography: can pain in a morphologically normal disc be due to an adjacent abnormal disc?" Arch Orthop Trauma Surg (2007) 127:699-703.
Boden et al., "Abnormal magnetic-resonance scans of the lumbar spine in asymptomatic subjects. A prospective investigation." The Journal of Bone & Joint Surgery (1990) 72:403-408.
Boos et al., "Natural History of Individuals With Asymptomatic Disc Abnormalities in Magnetic Resonance Imaging; Predictors of Low Back Pain-Related Medical Consultation and Work Incapacity." Spine vol. 25, No. 12, pp. 1484-1492 (2000).
Borenstein et al., "The Value of Magnetic Resonance Imaging of the Lumbar Spine to Predict Low-Back Pain in Asymptomatic Subjects: A Seven-Year Follow-up Study." The Journal of Bone & Joint Surgery (2001) 83:1306-1311.
Carragee et al., "2004 Outstanding Paper Award: Nonoperative Science; Discographic, MRI and psychosocial determinants of low back pain disability and remission: a prospective study in subjects with benign persistent back pain." The Spine Journal 5 (2005) 24-35.
Cherkin et al., "Physician Variation in Diagnostic Testing for Low Back Pain." Arthritis & Rheumatism, vol. 37, No. 1, Jan. 1994, pp. 15-22.
Freeborn et al., Primary Care Physicians' Use of Lumbar Spine Imaging Tests: Effects of Guidelines and Practice Pattern Feedback. JGIM, vol. 12, Oct. 1997, pp. 619-625.

(56) References Cited

OTHER PUBLICATIONS

Peng Z, "Automated Vertebra Detection and Segmentation from the Whole Spine MR Images," Proceedings of the 2005 IEEE Engineering in Medicine and Biology 27th Annual Conference, Shanghai, China, Sep. 1-4, 2005.

Wu M et al., "Quantitative comparison of AIR, SPM, and the fully deformable model for atlas-based segmentation of functional and structural MR images." Hum Brain Mapp. Sep. 2006; 27(9):747-54.

Liu J et al., "Rigid model-based 3D segmentation of the bones of joints in MR and CT images for motion analysis." Med Phys. Aug. 2008;35(8):3637-49.

Liu J et al., "Oriented active shape models." IEEE Trans Med Imaging. Apr. 2009; 28(4):571-84.

Chevrefils C et al., "Texture analysis for automatic segmentation of intervertebral disks of scoliotic spines from MR images." IEEE Trans Inf Technol Biomed. Jul. 2009; 13(4):608-20.

Huang SH et al., "Learning-based vertebra detection and iterative normalized-cut segmentation for spinal MRI." IEEE Trans Med Imaging. Oct. 2009; 28(10):1595-605.

Michopoulou SK et al., "Atlas-based segmentation of degenerated lumbar intervertebral discs from MR images of the spine." IEEE Trans Biomed Eng. Sep. 2009; 56(9):2225-31.

Kadoury S et al., "Personalized X-ray 3-D reconstruction of the scoliotic spine from hybrid statistical and image-based models." IEEE Trans Med Imaging. Sep. 2009; 28(9):1422-35.

Koh J et al., "Automatic segmentation of the spinal cord and the dural sac in lumbar MR images using gradient vector flow field." Conf Proc IEEE Eng Med Biol Soc. 2010; 2010:3117-20.

Hao S et al., "[Spine disc MR image analysis using improved independent component analysis based active appearance model and Markov random field]." Sheng Wu Yi Xue Gong Cheng Xue Za Zhi. Feb. 2010;27(1):6-9, 15.

Horsfield MA et al., "Rapid semi-automatic segmentation of the spinal cord from magnetic resonance images: application in multiple sclerosis." Neuroimage. Apr. 1, 2010; 50(2):446-55.

Bechara BP et al., "Application of a semiautomated contour segmentation tool to identify the intervertebral nucleus pulposus in MR images." AJNR Am J Neuroradiol. Oct. 2010; 31(9):1640-4.

Ben Ayed I et al., "Graph cuts with invariant object-interaction priors: application to intervertebral disc segmentation." Inf Process Med Imaging. 2011;22:221-32.

Dalca A et al., "Segmentation of nerve bundles and ganglia in spine MRI using particle filters." Med Image Comput Comput Assist Interv. 2011; 14(Pt 3):537-45.

Michopoulou S et. al., "Texture-based quantification of lumbar intervertebral disc degeneration from conventional T2-weighted MRI," Acta Radiologica 2011; 52: 91-98.

Neubert A, "Automated 3D Segmentation of Vertebral Bodies and Intervertebral Discs from MRI," 2011 International Conference on Digital Image Computing: Techniques and Applications.

Strickland CG et al., "Development of subject-specific geometric spine model through use of automated active contour segmentation and kinematic constraint-limited registration." J Digit Imaging. Oct. 2011; 24(5):926-42.

Giulietti G et al., "Semiautomated segmentation of the human spine based on echoplanar images," Magn Reson Imaging. Dec. 2011; 29(10):1429-36.

Stern D et al., "Parametric modelling and segmentation of vertebral bodies in 3D CT and MR spine images." Phys Med Biol. Dec. 7, 2011; 56(23):7505-22.

Neubert A et. al., "Automated detection, 3D segmentation and analysis of high resolution spine MR images using statistical shape models." Phys Med Biol. Dec. 21, 2012; 57(24):8357-76.

Egger J et al., "Square-cut: a segmentation algorithm on the basis of a rectangle shape." PLoS One. 2012;7(2).

Vrtovec T et al., "Automated curved planar reformation of 3D spine images." Phys Med Biol. Oct. 7, 2005; 50(19):4527-40.

International Search Report and Written Opinion dated Jul. 27, 2011 issued to international application No. PCT/US2010/052737.

International Search Report and Written Opinion dated Jul. 26, 2013 for international application No. PCT/US2013/036014.

International Search Report and Written Opinion dated Aug. 1, 2012 for PCT Application No. PCT/US2011/062137.

International Search Report and Written Opinion dated Sep. 25, 2014 for PCT Application No. PCT/US2014/022845.

\* cited by examiner

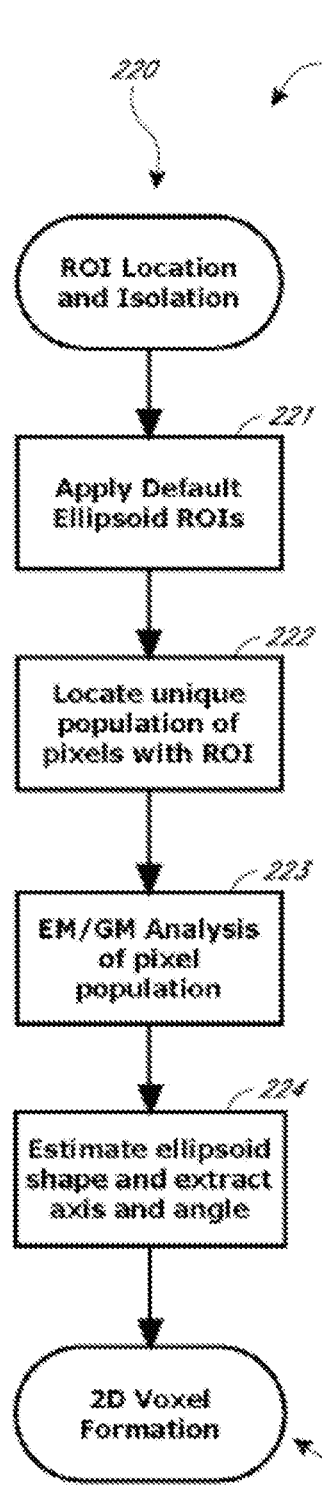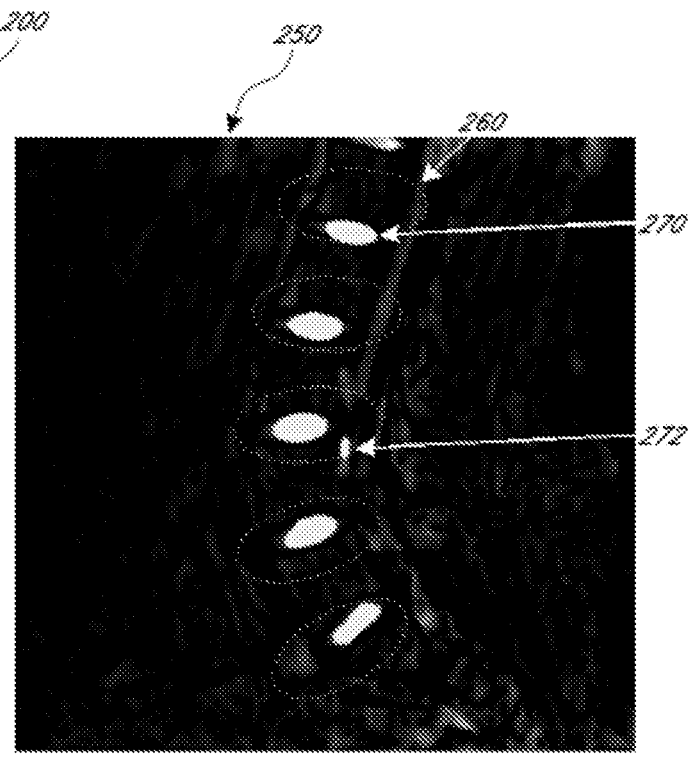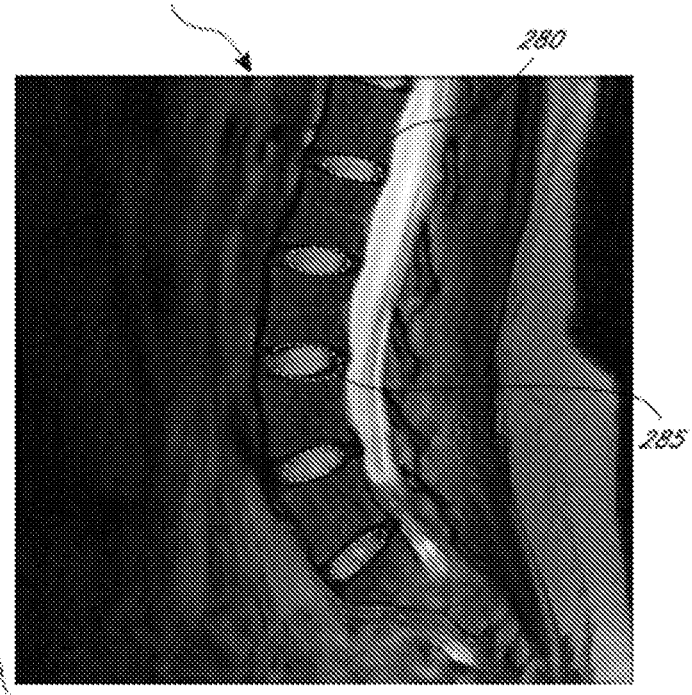
FIG. 8A
FIG. 8B
FIG. 8C

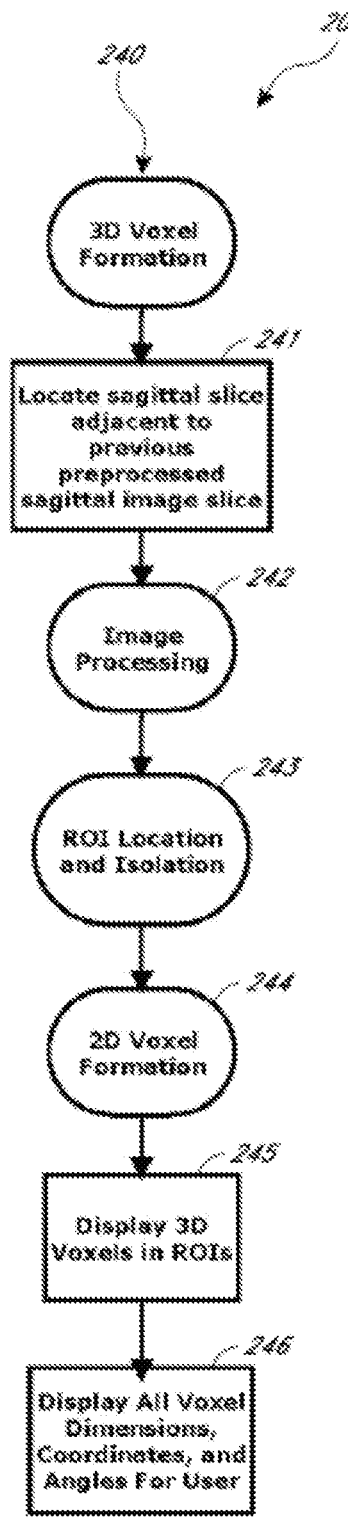
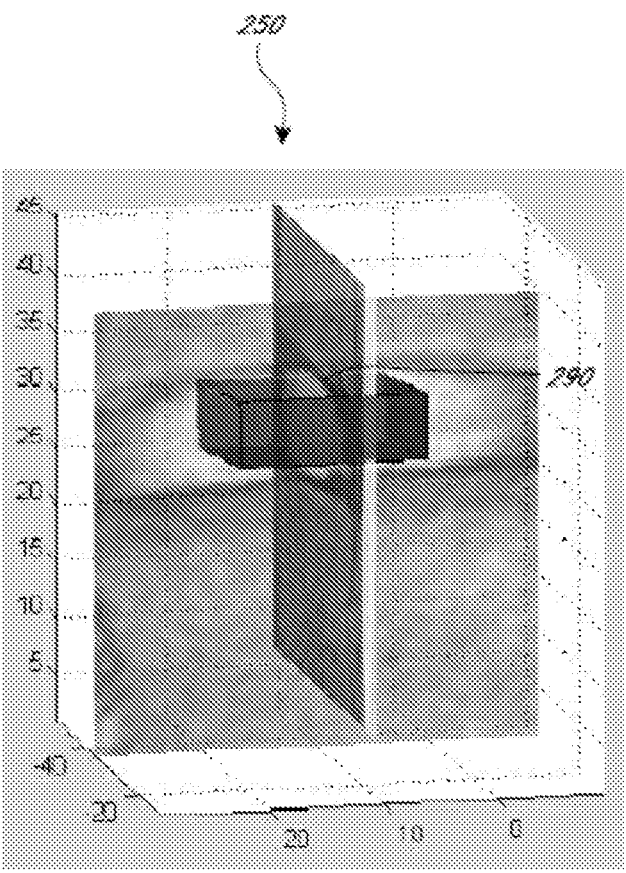
*FIG. 10B*
*FIG. 10A*
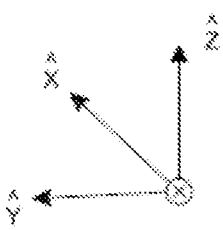

SYSTEMS AND METHODS FOR AUTOMATED VOXELATION OF REGIONS OF INTEREST FOR MAGNETIC RESONANCE SPECTROSCOPY

RELATED APPLICATIONS

This application is a continuation-in-part of PCT International Patent Application Number PCT/US2011/062137 (Publication Number WO 2012/071566), filed Nov. 23, 2011 and titled "SYSTEMS AND METHODS FOR AUTOMATED VOXELATION OF REGIONS OF INTEREST FOR MAGNETIC RESONANCE SPECTROSCOPY", which claims the benefit of U.S. Provisional Patent Application No. 61/417,182, filed Nov. 24, 2010, and titled "SYSTEMS AND METHODS FOR AUTOMATED VOXELATION OF REGIONS OF INTEREST FOR SINGLE VOXEL MAGNETIC RESONANCE SPECTROSCOPY." The entirety of each of these related priority patent applications is hereby incorporated by reference and made a part of this specification for all that it discloses.

INCORPORATION BY REFERENCE

The following disclosures are hereby incorporated by reference in their entirety and made a part of this specification for all that they disclose: U.S. Patent Publication No. 2008/0039710, filed Jul. 27, 2007, and titled "SYSTEM AND METHODS USING NUCLEAR MAGNETIC RESONANCE (NMR) SPECTROSCOPY TO EVALUATE PAIN AND DEGENERATIVE PROPERTIES OF TISSUE"; U.S. Patent Publication No. 2009/0030308, filed Mar. 21, 2008, and titled "SYSTEM, COMPOSITION, AND METHODS FOR LOCAL IMAGING AND TREATMENT OF PAIN"; International Patent Publication No. WO 2009/148550, filed May 29, 2009, and titled "BIOMARKERS FOR PAINFUL INTERVERTEBRAL DISCS AND METHODS OF USE THEREOF"; U.S. Patent Publication No. 2011/0087087, filed Oct. 14, 2009, and titled "MR SPECTROSCOPY SYSTEM AND METHOD FOR DIAGNOSING PAINFUL AND NON-PAINFUL INTERVERTEBRAL DISCS"; and International Patent Publication No. WO 2011/047197, filed Oct. 14, 2010, and titled "MR SPECTROSCOPY SYSTEM AND METHOD FOR DIAGNOSING PAINFUL AND NON-PAINFUL INTERVERTEBRAL DISCS".

BACKGROUND

1. Field of the Disclosure

The present disclosure relates to segmentation of electronic images to specific regions of interest in a field of view, such as for example tissue structures in medical imaging; and also for improvements to clinical magnetic resonance spectroscopy (MRS), for example, to single or multi-voxel MRS; and also to the automated prescription of voxels within regions of interest where MRS is to be performed, such as for example in intervertebral discs.

2. Description of the Related Art

Conventional systems and methods for prescribing voxel size and position within a region of interest (ROI) for magnetic resonance spectroscopy (MRS) applications involve manual techniques by an operator technician working from magnetic resonance imaging (MRI) images taken prior to the prescription operation. This standard approach suffers from various drawbacks. These include, for example but without limitation: (1) limitations in the ability to accurately define the ROI boundaries within which the voxel should be fit; and (2) drawbacks from manual prescription such as (a) time required to perform the prescription under time constraints of an overall exam, and (b) achieving optimal trade off between (i) maximizing voxel volume within the ROI for maximum signal:noise ratio (SNR) and (ii) confining the voxel within only the ROI boundaries and avoiding overlap with adjacent tissues outside of the ROI—which can potentially blend chemical information between tissue constituents within the ROI and extraneous constituents outside of the ROI into the acquired spectra, and thus potentially compromise diagnostic interpretation and results.

In addition, diagnostic imaging exams are typically reliant upon a fixed positioning of the patient during the exam, and may be compromised by patient motion during the image acquisition. This also directly applies, for example but without limitation, to MRS exams. In particular, an accurate voxel prescription which aligns the region for MRS data acquisition to an ROI will become mis-registered with that tissue ROI if the patient moves after the prescription but before completion of the image acquisition. The information acquired may blur pre- and post-motion information during the image acquisition process, and/or may introduce chemical information from tissues which originally were extraneous to the voxel location, but due to the motion were introduced into the voxel location due to moving the anatomy relative to the fixed voxel.

These issues represent particularly poignant challenges for conducting MRS in musculoskeletal applications, in particular skeletal joints, and still more particularly intervertebral discs. This is also especially for example the case in settings where, but without limitation, target tissue ROIs have limited volumes, requiring maximum voxel volume to achieve sufficient SNR, and are located adjacent to other tissues (e.g. next to or between bones, such as for example in skeletal joints) with dramatically different chemical constituents than the ROI—and thus could introduce significant unintended chemical signatures into acquired spectra if there is voxel overlap outside the ROI or due to patient motion during an exam.

In the particularly unique setting of intervertebral discs, the disc tissues are bordered by opposite end-plates of superior and inferior vertebral bodies, in addition to laterally by a number of different tissue structures (e.g. spinal canal). These introduce dramatically higher contents of lipid (in the case of bony structures), and water (e.g. in the case of spinal canal), than in the disc itself. Moreover, the discs are relatively small for conventional MRS voxel purposes. This is further confounded by prevalent disease conditions where diagnostic imaging (and MRS in particular) may often be indicated, such as degenerative disc disease, that are specifically characterized by abnormally reduced disc height and volume as well as dehydration and dessication of the disc tissue. These issues represent a landscape that is more challenging for defining (e.g. "segmenting") the disc material ROI from surrounding structures, such as for example for diagnostic image analysis or to define regions for directed therapies. In particular context of MRS, they also represent an environment for inherently low SNR, and accordingly require maximum possible voxel volume to be prescribed. Furthermore, the relatively small geographies and close proximities of discs relative to their bordering tissues heightens the risks and potential impact of patient motion during a disc-related imaging exam, such as especially but not limited to disc MRS exams.

These issues noted above are uniquely implicated in the ability to successfully perform single voxel spectroscopy in skeletal joints, and especially intervertebral discs, though they also relate to multi-voxel spectroscopy, and other imaging considerations (MR-related or otherwise), and other tissue structures.

SUMMARY OF SOME EMBODIMENTS

The current disclosure includes, among other aspects, certain solutions which address and overcome one or more of issues noted above. While such solutions are herein presented as uniquely tailored and beneficial for addressing the specific challenges relative to particular anatomies and related considerations, they will also be applicable and present benefits elsewhere in other anatomies and/or indications or purposes.

Accordingly, certain aspects of this disclosure provide, and address and overcome a need for, a reliable automated system and method for segmenting target tissue regions of interest (ROIs) from medical diagnostic images.

Other aspects of this disclosure provide, and address and overcome a need for, a reliable automated system and method for prescribing a voxel in an ROI for magnetic resonance spectroscopy (MRS) applications.

Still other aspects of this disclosure provide, and address and overcome a need for, a reliable automated system and method for identifying patient motion during an imaging exam.

Specific modes of these aspects are in particular tailored and suitable for providing beneficial use in, without limitation: skeletal joints, and in particular connective tissue regions between bones of such joints, and in particular intervertebral discs.

The disclosed systems and methods also provide useful, beneficial solutions for other applications, including for example but not limited to image data post-processing and analysis (e.g. quantification), directed therapies targeting tissue ROIs defined by such segmentation, patient motion assessment during an imaging exam (and potentially including dynamic adjustment of the imaging parameters), and single and multi-voxel MRS (including without limitation automated voxel prescription).

Various embodiments disclosed in the present disclosure relate to systems and methods for locating, analyzing, or otherwise obtaining information relating to a region of interest related to an electronic image (and real world spatial coordinates represented by such images). Various embodiments relate to automated voxelation of regions of interest for single (or multi-) voxel magnetic resonance spectroscopy. Various features are described below and can be used in various combinations with each other. Many combinations of the features described below will be apparent which are not specifically discussed and are a part of this disclosure, as would be apparent to one of ordinary skill.

One aspect of the present disclosure includes one or more computer readable media comprising computer instructions configured to cause one or more computer processors to perform actions comprising:
  accessing an electronic image of an area that includes a region of interest;
  processing the electronic image to emphasize pixels associated with at least one structure useful for identifying the region of interest;
  identifying a population of pixels in the electronic image associated with the at least one structure;
  selecting one or more image coordinates based on the population of pixels; and
  converting the image coordinates to world coordinates corresponding to at least a portion of the region of interest.
This aspect of the disclosure can be combined with the other aspects, modes, embodiments, variations, and features described herein to form various combinations and sub-combinations.

According to one mode of the present disclosure, the electronic image comprises a magnetic resonance imaging (MRI) image.

According to one mode of the present disclosure, selecting image coordinates comprises selecting a two dimensional shape that covers a selected area of the region of interest when converted to world coordinates.

According to one embodiment of the present disclosure, the two dimensional shape is rectilinear.

According to one mode of the present disclosure, selecting image coordinates comprises calculating a two dimensional model that approximates the region of interest based on the population of pixels.

According to one embodiment of the present disclosure, calculating the two dimensional model comprises applying an expectation maximization algorithm for estimating parameters of one or more Gaussian distributions for the population of pixels.

According to one embodiment of the present disclosure, the computer instructions are configured to cause the one or more computer processors to position a two dimensional shape based on the two dimensional model to cover a selected area of the region of interest.

According to one mode of the present disclosure, the computer instructions are further configured to cause the one or more computer processors to output information relating to the region of interest based on the world coordinates, the information comprising one or more of a location, an orientation, a shape, an area, and a volume of the region of interest.

According to one mode of the present disclosure, the computer instructions are configured to cause the one or more computer processors to perform additional actions comprising:
  accessing one or more additional electronic images of one or more areas that also include the region of interest;
  processing the one or more additional electronic images to emphasize pixels that are associated with the at least one structure useful for identifying the region of interest in the one or more additional electronic images;
  identifying one or more additional populations of pixels in the corresponding one or more additional electronic images, the one or more additional populations of pixels being associated with the at least one structure;
  selecting one or more additional image coordinates from the one or more additional electronic images, the one or more additional image coordinates being based on the one or more additional populations of pixels; and
  converting the one or more additional image coordinates to world coordinates corresponding to at least a portion of the region of interest.

According to one embodiment of the present disclosure, the electronic images are of slices substantially parallel to, and spaced apart from, each other.

According to one embodiment of the present disclosure, the world coordinates define a three dimensional selected volume of the region of interest.

According to one variation of the present disclosure, the computer readable media is configured to be used with a magnetic resonance spectroscopy (MRS) system in communication with the one or more computer processors, wherein the MRS system is configured to provide an MRS spectrum of chemical constituents within the three dimensional selected volume.

According to one variation of the present disclosure, the computer instructions are further configured to cause the one or more computer processors to analyze a post-acquisition scan to determine whether the region of interest moved during an MRS acquisition.

According to one variation of the present disclosure, the region of interest is a nucleus of an intervertebral disc of a spine.

According to one variation of the present disclosure, the computer instructions are configured to analyze the MRS spectrum and to determine whether the three dimensional selected volume was likely mis-prescribed based on one or more signals.

According to one variation of the present disclosure, the one or more signals comprise a lipid signal.

According to one variation of the present disclosure, the computer instructions are configured to provide a single three dimensional scan volume to the MRS system configured for single voxel MRS.

According to one variation of the present disclosure, the computer instructions are configured to cause the one or more computer processors to select multiple three dimensional volumes corresponding to multiple regions of interest and to provide the multiple three dimensional volumes to the MRS system configured for multivoxel MRS.

According to one variation of the present disclosure, the electronic image is of a first acquisition mode, and the MRS spectrum is of a second acquisition mode different than the first acquisition mode.

According to one embodiment of the present disclosure, the three dimensional selected volume is a rectilinear volume.

According to one embodiment of the present disclosure, the computer instructions are configured to cause the one or more computer processors to define a two dimensional shape using the initial electronic image, the two dimensional shape corresponding to a cross sectional shape of the three dimensional selected volume, and to modify the cross sectional shape of the three dimensional selected volume to fit the region of interest corresponding to at least one of the one or more additional electronic images.

According to one embodiment of the present disclosure, the computer instructions are configured to cause the one or more computer processors to define a plurality of two dimensional shapes associated with the region of interest for the corresponding electronic images, and wherein the three dimensional selected volume has a cross sectional shape corresponding to the overlapping area of the plurality of two dimensional shapes.

According to one embodiment of the present disclosure, the computer readable media can be configured to be used with a patient therapy system configured to provide a therapy procedure to a patient based at least in part on the three dimensional selected volume.

According to one variation of the present disclosure, the patient therapy system is a radiation therapy system or an ultrasound therapy system configured to direct energy to the three dimensional selected volume.

According to one embodiment of the present disclosure, the computer instructions are configured to cause the one or more computer processors to calculate a three dimensional model that approximates the region of interest based on the populations of pixels from the electronic images.

According to one embodiment of the present disclosure, the electronic images are magnetic resonance imaging (MRI) images and the computer instructions are configured to cause the one or more computer processors to receive the MRI images from an MRI system in communication with the one or more computer processors.

According to one mode of the present disclosure, processing the electronic image comprises smoothing the electronic image.

According to one embodiment of the present disclosure, smoothing the electronic image comprises modifying a brightness value for a pixel based on the brightness of neighboring pixels.

According to one variation of the present disclosure, the neighboring pixels comprise one or more pixels from one or more additional neighboring electronic images.

According to one mode of the present disclosure, processing the electronic image comprises performing at least one top-hat filtering operation.

According to one mode of the present disclosure, processing the electronic image comprises performing at least one morphological image processing operation.

According to one embodiment of the present disclosure, processing the electronic image comprises performing a first top-hat filtering operation on an upper portion of the spine and performing a second top-hat filtering operation on a lower curved portion of the spine.

According to one mode of the present disclosure, processing the electronic image comprises performing an order statistic filtering operation.

According to one mode of the present disclosure, the at least one structure comprises the region of interest, the computer instructions being configured to cause the one or more computer processors to process the electronic image to emphasize the region of interest.

According to one mode of the present disclosure, the at least one structure comprises at least one structure adjacent to the region of interest.

According to one mode of the present disclosure, indentifying the population of pixels in the electronic image comprises analyzing pixels in a predefined search area of the electronic image and assigning analyzed pixels having a particular property to the population of pixels associated with the at least one structure.

According to one embodiment of the present disclosure, the particular property is a pixel brightness intensity.

According to one embodiment of the present disclosure, the predefined search area is based on statistical analysis of historical data relating to a likely location for the at least one structure.

According to one mode of the present disclosure, indentifying the population of pixels in the electronic image is based on input from an operator, the input comprising one or more locations associated with the at least one structure.

According to one mode of the present disclosure, the computer instructions are further configured to cause the one or more computer processors to analyze the population of pixels based on at least one reliability criteria.

According to one mode of the present disclosure, the at least one reliability criteria comprises a comparison of a number of pixels in the population of pixels to a threshold pixel number.

According to one embodiment of the present disclosure, when the population of pixels does not satisfy the reliability criteria, the computer instructions cause the one or more processors to flag the population of pixels for review by a user.

According to one embodiment of the present disclosure, when the population of pixels does not satisfy the reliability criteria, the computer instructions cause the one or more processors to employ additional algorithms to modify the population of pixels to improve reliability.

One aspect of the present disclosure is a system for obtaining information relating to a region of interest, the system comprising:
- a one or more computer readable media according to (or configured to perform the method of) any one of the aspects, modes, embodiments, or variations identified herein; and
- one or more computer processors in communication with the computer readable media for executing the computer instructions. This aspect of the disclosure can be combined with the other aspects, modes, embodiments, variations, and features described herein to form various combinations and sub-combinations.

One mode of the present disclosure further comprises a magnetic resonance spectroscopy (MRS) system in communication with the one or more computer processors, wherein the MRS system is configured to provide an MRS spectrum of chemical constituents within the region of interest.

One mode of the present disclosure further comprises a magnetic resonance imaging (MRI) system in communication with the one or more computer processors, wherein the MRI system is configured to provide a plurality of MRI images.

According to one mode of the present disclosure, the electronic image is of a first imaging mode, wherein the computer instructions are further configured to cause the one or more processors to access an additional electronic image of a second imaging mode different than the first imaging mode, the additional electronic image being of the substantially the same area as the initial electronic image, wherein the world coordinates are based in part on the additional electronic image of the second imaging mode.

According to one embodiment of the present disclosure, the computer instructions are further configured to cause the one or more processors to:
- process the additional electronic image to emphasize pixels in the additional electronic image that are associated with the at least one structure useful for identifying the region of interest;
- identify a population of pixels in the additional electronic image associated with the at least one structure; and
- combine information based on the population of pixels in the additional electronic image with information based on the population of pixels in the initial electronic image to generate the world coordinates.

According to one mode of the present disclosure, the computer instructions are further configured to cause the one or more processors to:
- process the additional electronic image to emphasize pixels in the additional electronic image that are associated with the at least one structure useful for identifying the region of interest;
- identify a population of pixels in the additional electronic image associated with the at least one structure; and
- compare information based on the population of pixels in the additional electronic image with information based on the population of pixels in the initial electronic image to generate the world coordinates to evaluate accuracy of the world coordinates.

One aspect of the present disclosure is a method for obtaining information relating to a region of interest, the method comprising:
- accessing an electronic image of an area that includes a region of interest;
- processing the electronic image, using one or more computer processors, to emphasize pixels associated with at least one structure useful for identifying the region of interest;
- identifying a population of pixels in the electronic image associated with the at least one structure;
- selecting one or more image coordinates based on the population of pixels; and
- converting the image coordinates to world coordinates corresponding to at least a portion of the region of interest. This aspect of the disclosure can be combined with the other aspects, modes, embodiments, variations, and features described herein to form various combinations and sub-combinations.

According to one mode of the present disclosure, the electronic image comprises a magnetic resonance imaging (MRI) image.

According to one embodiment of the present disclosure, selecting image coordinates comprises selecting a two dimensional shape that covers a selected area of the region of interest when converted to world coordinates.

According to one mode of the present disclosure, selecting image coordinates comprises calculating a two dimensional model that approximates the region of interest based on the population of pixels.

According to one embodiment of the present disclosure, calculating the two dimensional model comprises applying an expectation maximization algorithm for estimating parameters of one or more Gaussian distributions for the population of pixels.

According to one embodiment of the present disclosure, the computer instructions are configured to cause the one or more computer processors to position a two dimensional shape based on the two dimensional model to cover a selected area of the region of interest.

One mode of the present disclosure further comprises outputting information relating to the region of interest based on the world coordinates, the information comprising one or more of a location, an orientation, a shape, an area, and a volume of the region of interest.

One mode of the present disclosure further comprises:
- accessing one or more additional electronic images of one or more areas that also include the region of interest;
- processing the one or more additional electronic images, with the one or more computer processors, to emphasize pixels that are associated with the at least one structure useful for identifying the region of interest in the one or more additional electronic images;
- identifying one or more additional populations of pixels in the corresponding one or more additional electronic images, the one or more additional populations of pixels being associated with the at least one structure;
- selecting one or more additional image coordinates from the one or more additional electronic images, the one or more additional image coordinates being based on the one or more additional populations of pixels; and
- converting the one or more additional image coordinates to world coordinates corresponding to at least a portion of the region of interest.

According to one embodiment of the present disclosure, the world coordinates define to a three dimensional selected volume of the region of interest.

One variation of the present disclosure further comprises scanning the three dimensional selected volume with a magnetic resonance spectroscopy (MRS) system in communication with the one or more computer processors to provide an MRS spectrum of chemical constituents within the three dimensional selected volume.

One variation of the present disclosure further comprises analyzing a post-acquisition scan, using the one or more computer processors, to determine whether the region of interest moved during an MRS acquisition.

According to one variation of the present disclosure, the region of interest is a nucleus of an intervertebral disc of a spine.

One variation of the present disclosure further comprises analyzing the MRS spectrum, using the one or more computer processors, to determine whether the three dimensional selected volume was likely mis-prescribed based on one or more signals.

One variation of the present disclosure further comprises defining one or more additional three dimensional selected volumes covering at least portions of one or more additional regions of interest, and scanning the additional three dimensional selected volumes one at a time with the MRS system using single voxel MRS.

One variation of the present disclosure further comprises defining one or more additional three dimensional selected volumes covering at least portions of one or more additional regions of interest, and scanning the additional three dimensional selected volumes simultaneously with the MRS system using multivoxel MRS.

According to one variation of the present disclosure, the electronic image is of a first acquisition mode, and wherein the MRS spectrum is of a second acquisition mode different than the first acquisition mode.

One variation of the present disclosure further comprises:
defining a two dimensional shape using the initial electronic image, the two dimensional shape corresponding to a cross sectional shape of the three dimensional selected volume; and
modifying the cross sectional shape of the three dimensional selected volume to fit the region of interest corresponding to at least one of the one or more additional electronic images.

One variation of the present disclosure further comprises defining a plurality of two dimensional shapes associated with the region of interest for the corresponding electronic images, wherein the three dimensional selected volume has a cross sectional shape corresponding to the overlapping area of the plurality of two dimensional shapes.

One variation of the present disclosure further comprises using with a patient therapy system to provide a therapy procedure to a patient based at least in part on the three dimensional selected volume.

According to one variation of the present disclosure, the patient therapy system is a radiation therapy system or an ultrasound therapy system configured to direct energy to the three dimensional selected volume.

One embodiment of the present disclosure further comprises calculating a three dimensional model that approximates the region of interest based on the populations of pixels from the electronic images.

According to one embodiment of the present disclosure, the electronic images comprise magnetic resonance imaging (MRI) images, and the method further comprising acquiring the MRI images using an MRI system in communication with the one or more computer processors.

According to one mode of the present disclosure, processing the electronic image comprises smoothing the electronic image.

According to one embodiment of the present disclosure, smoothing the electronic image comprises modifying a brightness value for a pixel based on the brightness of neighboring pixels.

According to one embodiment of the present disclosure, the neighboring pixels comprise one or more pixels from one or more additional neighboring electronic images.

According to one mode of the present disclosure, processing the electronic image comprises performing at least one top-hat filtering operation.

According to one mode of the present disclosure, processing the electronic image comprises performing at least one morphological image processing operation.

According to one embodiment of the present disclosure, processing the electronic image comprises performing a first top-hat filtering operation on an upper portion of the spine and performing a second top-hat filtering operation on a lower curved portion of the spine.

According to one mode of the present disclosure, processing the electronic image comprises performing an order statistic filtering operation.

According to one mode of the present disclosure, the at least one structure comprises the region of interest, wherein processing the electronic image comprises emphasizing the region of interest.

According to one mode of the present disclosure, the at least one structure comprises at least one structure adjacent to the region of interest.

According to one mode of the present disclosure, indentifying the population of pixels in the electronic image comprises analyzing pixels in a predefined search area of the electronic image and assigning analyzed pixels having a particular property to the population of pixels associated with the at least one structure.

According to one embodiment of the present disclosure, the particular property is a pixel brightness intensity.

According to one embodiment of the present disclosure, the predefined search area is based on statistical analysis of historical data relating to a likely location for the at least one structure.

One mode of the present disclosure further comprises receiving input from an operator, the input comprising one or more locations associated with the at least one structure, and wherein identifying the population of pixels in the electronic image is based on the input.

One mode of the present disclosure further comprises analyzing the population of pixels, using the one or more computer processors, based on at least one reliability criteria.

According to one embodiment of the present disclosure, the at least one reliability criteria comprises a comparison of a number of pixels in the population of pixels to a threshold pixel number.

One embodiment of the present disclosure further comprises, when the population of pixels does not satisfy the reliability criteria, flagging the population of pixels for review by a user.

One embodiment of the present disclosure further comprises, when the population of pixels does not satisfy the reliability criteria, employing additional algorithms to modify the population of pixels to improve reliability.

According to one mode of the present disclosure, each of the actions recited is performed by the one or more processors.

According to one mode of the present disclosure, the electronic image is of a first imaging mode, and wherein the method further comprises accessing an additional electronic image of a second imaging mode different than the first imaging mode, the additional electronic image being of the substantially the same area as the initial electronic image, wherein the world coordinates are based in part on the additional electronic image of the second imaging mode.

One mode of the present disclosure further comprises:
processing the additional electronic image to emphasize pixels in the additional electronic image that are associated with the at least one structure useful for identifying the region of interest;
identify a population of pixels in the additional electronic image associated with the at least one structure; and
combining information based on the population of pixels in the additional electronic image with information based on the population of pixels in the initial electronic image to generate the world coordinates.

One embodiment of the present disclosure further comprises:
processing the additional electronic image to emphasize pixels in the additional electronic image that are associated with the at least one structure useful for identifying the region of interest;
identify a population of pixels in the additional electronic image associated with the at least one structure; and
comparing information based on the population of pixels in the additional electronic image with information based on the population of pixels in the initial electronic image to generate the world coordinates to evaluate accuracy of the world coordinates.

One aspect of the present disclosure is a method for prescribing a shape within a region of interest (ROI) in an electronic image of a body portion of a patient, comprising:
defining the ROI in the electronic image;
prescribing the shape to fit within the ROI in the electronic image; and
using one or more processors to process the electronic image to perform at least one of defining the ROI and prescribing the shape. This aspect of the disclosure can be combined with the other aspects, modes, embodiments, variations, and features described herein to form various combinations and sub-combinations.

One aspect of the present disclosure is a method for configuring a medical system to be used in performing an operation on a region of interest (ROI) in a body portion of a patient, the method comprising:
using one or more processors to process an electronic image to define the ROI in the electronic image; and
configuring the medical system in a configuration that is operable to perform the operation on at least a portion of the ROI. This aspect of the disclosure can be combined with the other aspects, modes, embodiments, variations, and features described herein to form various combinations and sub-combinations.

One aspect of the present disclosure is a method for defining a region of interest (ROI) between bones in an electronic image of a body portion comprising a skeletal joint in a patient, the method comprising:
using one or more processors to process the electronic image to identify a region between the bones and bordered at least in part by the bones, and to define the ROI to coincide with at least a part of the region. This aspect of the disclosure can be combined with the other aspects, modes, embodiments, variations, and features described herein to form various combinations and sub-combinations.

One mode of the present disclosure further comprises configuring a medical system in a configuration that is operable to perform an operation on the ROI.

According to one mode of the present disclosure, the body portion comprises a skeletal joint and the ROI is located at least in part between bones of the skeletal joint, the method further comprising using the one or more processors to process the electronic image to identify a region between the bones and bordered at least in part by the bones, and to define the ROI to coincide with at least a part of the region.

One embodiment of the present disclosure further comprises configuring a medical system in a configuration that is operable to perform an operation on the ROI.

According to one mode of the present disclosure, the body portion comprises a skeletal joint and the ROI is located at least in part between bones of the skeletal joint, and further comprising using the one or more processors to process the electronic image to identify a region between the bones and bordered at least in part by the bones, and to define the ROI to coincide with at least a part of the region.

One mode of the present disclosure further comprises using the one or more processors to process the electronic image to define the ROI.

One mode of the present disclosure further comprises using the one or more processors to process the electronic image to prescribe the shape.

According to one embodiment of the present disclosure, prescribing the shape is entirely performed using the one or more processors.

According to one embodiment of the present disclosure, prescribing the shape is partially performed using the one or more processors.

One mode of the present disclosure further comprises prescribing a shape to fit within the ROI.

One embodiment of the present disclosure further comprises using the one or more processors to process the electronic image to prescribe the shape.

One mode of the present disclosure further comprises prescribing a shape to fit within the ROI.

One embodiment of the present disclosure further comprises using the one or more processors to process the electronic image to prescribe the shape.

According to one mode of the present disclosure, said electronic image comprises a 2D planar image.

One embodiment of the present disclosure further comprises using the one or more processors to process the 2D planar image to define the ROI as a 2D ROI in the 2D planar image.

One variation of the present disclosure further comprises using the one or more processors to process the 2D planar image to prescribe a 2D shape to fit within the 2D ROI.

One embodiment of the present disclosure further comprises using the one or more processors to process the 2D planar image to prescribe a 2D shape to fit within a 2D ROI.

According to one mode of the present disclosure, said electronic image comprises a 3D electronic image constructed from a series of spatially unique but related 2D planar images of the body portion, and further comprising using the one or more processors to: process multiple said 2D planar images within the series to define multiple respective 2D ROIs therein, and to construct a 3D ROI in the 3D image from the multiple 2D ROIs.

According to one embodiment of the present disclosure, the 3D ROI corresponds with a definable structure within the body portion, and further comprising using the one or more processors to process the 3D electronic image to define the 3D ROI by applying a template map to each of said plurality of 2D planar images and providing a default region predictive of locating said structure in each said respective 2D planar images based on prior knowledge derived from other similar 2D planar images from other patients, and processing the default region in the 2D planar image to define the 2D ROI from which the 3D ROI is constructed.

One variation of the present disclosure further comprises using the one or more processors to process multiple of the 2D planar images to prescribe a 3D shape to fit within the 3D ROI in the 3D image.

According to one mode of the present disclosure, the ROI corresponds with a definable structure within the body portion, and further comprising using the one or more processors to process the electronic image to define the ROI using a template map providing a default region predictive of locating said structure based on location information derived from other electronic images from other patients, and processing the default region in the electronic image to define the ROI.

According to one embodiment of the present disclosure, the default region processing comprises at least one of edge detection and a contrast filter.

One mode of the present disclosure further comprises using the one or more processors to process the electronic image to define the ROI using edge detection.

One mode of the present disclosure further comprises using the one or more processors to process the electronic image to define the ROI using a contrast filter.

One embodiment of the present disclosure further comprises using the one or more processors to process the electronic image to define the ROI using edge detection.

One variation of the present disclosure further comprises prescribing the 3D shape to achieve a criteria related to volume or dimension of the 3D shape.

According to one variation of the present disclosure, the criteria comprises a maximum contained volume or dimension within the 3D ROI.

One variation of the present disclosure further comprises:
  using the one or more processors to process the electronic image to determine an initial 3D ROI and to apply an inward dimensional off-set from an outer boundary of the initial 3D ROI to define an off-set 3D region in the image; and
  using the one or more processors to define the ROI to coincide at least in part with the off-set 3D region.

One variation of the present disclosure further comprises using the one or more processors to process the electronic image to prescribe multiple said 3D shapes within the 3D ROI.

One variation of the present disclosure further comprises prescribing the multiple 3D shapes to collectively achieve a criteria relating to volume of the 3D shapes.

According to one variation of the present disclosure, the criteria comprises a maximum contained volume within the 3D ROI.

One variation of the present disclosure further comprises using the one or more processors to apply an inward dimensional off-set from an outer boundary of the 3D ROI for form an off-set 3D ROI, and prescribing the multiple 3D shapes to collectively achieve a criteria relating to a volume of the 3D shapes.

According to one variation of the present disclosure, the criteria comprises a maximum contained volume within the off-set 3D ROI.

One variation of the present disclosure further comprises configuring a medical system to perform an operation on at least a part of the 3D ROI corresponding with the multiple 3D shapes.

According to one variation of the present disclosure, the medical system comprises a nuclear magnetic resonance (MR) system, and further comprising:

configuring the MR system in a configuration that is operable in an operating mode to acquire MR-based data from at least the part of the 3D ROI, such that multiple portions of the MR-based data acquired in the operating mode correspond with each of the multiple 3D shapes; and
  correlating the multiple portions of the MR-based data with unique locations of the respective multiple 3D shapes.

According to one variation of the present disclosure, the configuration comprises a T2-weighted imaging sequence.

According to one variation of the present disclosure, the configuration comprises a T1-weighted imaging sequence.

According to one variation of the present disclosure, the configuration comprises an MR spectroscopy (MRS) pulse sequence.

According to one variation of the present disclosure, the configuration comprises a T1-rho pulse sequence.

One variation of the present disclosure further comprises correlating a value of the MR-based data for each of the 3D shapes with a diagnostic criteria.

One variation of the present disclosure further comprises displaying an indicia related to the correlation for each of the 3D shapes as an overlay to the electronic image.

One variation of the present disclosure further comprises defining the 3D ROI and prescribing the 3D shapes before configuring the operating the medical system in the configuration.

One variation of the present disclosure further comprises using the defined 3D ROI and 3D shape prescriptions to configure the medical system in the configuration.

One variation of the present disclosure further comprises defining the 3D ROI and prescribing the 3D shapes after configuring the medical system in the configuration and after operating the medical system in the operating mode.

One variation of the present disclosure further comprises using the 3D shapes to correlate the operation corresponding with portions of the ROI represented by the respective 3D shapes.

One variation of the present disclosure further comprises:
  using the one or more processors to prescribe said multiple 3D shapes as voxels; and
  after prescribing the voxels, configuring a magnetic resonance spectroscopy (MRS) system in a configuration that is operable to acquire MRS information from each of the voxels.

One mode of the present disclosure further comprises using the one or more processors to process the electronic image to prescribe a single shape that is a different shape than the ROI to fit within the ROI to achieve a criteria relating to volume or dimension of the single shape.

According to one embodiment of the present disclosure, the criteria comprises a maximized dimension or contained volume within the single shape.

One mode of the present disclosure further comprises:
  using the one or more processors to process the electronic image to determine an initial ROI comprising an outer boundary, and to apply an inward dimensional off-set from the outer boundary to define an off-set region in the image; and
  using the one or more processors to define the ROI to coincide at least in part with the off-set region.

According to one mode of the present disclosure, the ROI and the shape comprise different respective geometries.

According to one embodiment of the present disclosure, the ROI comprises a geometry comprising at least one non-straight linear edge boundary.

According to one variation of the present disclosure, the ROI comprises at least in part a curvilinear edge boundary.

According to one embodiment of the present disclosure, the shape comprises a rectilinear geometry.

One mode of the present disclosure further comprises prescribing the shape for achieving a criteria related to volume or dimension of the shape.

According to one embodiment of the present disclosure, the criteria comprises a maximized dimension or contained volume within the ROI.

According to one mode of the present disclosure, the ROI comprises at least a portion of an intervertebral disc between two superior and inferior respective vertebral bodies bordering the disc.

One embodiment of the present disclosure further comprises using the one or more processors to define the ROI at least in part by locating two superior and inferior borders between the disc and the vertebral bodies in the electronic image.

According to one variation of the present disclosure, the borders comprise vertebral body end-plates.

One variation of the present disclosure further comprises defining the ROI by defining at least one annular wall of the disc and connecting the vertebral bodies in the electronic image, such that the ROI is defined as a region contained between the borders and the at least one annular wall of the disc.

According to one variation of the present disclosure, the electronic image comprises a 2D planar image through the disc and vertebral bodies, and further comprising defining the ROI by defining first and second opposite portions of the annular wall in the electronic image, such that the ROI is defined as a region contained between the borders and the two opposite portions of the annular wall.

According to one variation of the present disclosure, the electronic image comprises a 2D planar image and each of the borders comprises a line first end and a second end, and further comprising defining the ROI by defining two connecting lines between first ends and second ends of the respective borders, thereby confining the ROI as an area contained within the borders and connecting lines.

According to one variation of the present disclosure, the ROI comprises a nucleus portion of the intervertebral disc.

According to one variation of the present disclosure, the ROI comprises an annulus portion of the intervertebral disc.

One variation of the present disclosure further comprises defining first and second said ROIs comprising a nucleus portion and an annulus portion of the disc, respectively, and prescribing a first shape to fit within the first ROI and a second shape to fit within the second ROI.

One mode of the present disclosure further comprises using the one or more processors to operate a computer program in a computer readable medium for performing the processing of the electronic image.

One mode of the present disclosure further comprises configuring an MR system in a configuration that is operable to perform an MR operation on at least a portion of the ROI corresponding with the shape.

One embodiment of the present disclosure further comprises configuring the MR system in a configuration that is operable to acquire a T1-weighted image of at least the portion of the ROI.

One embodiment of the present disclosure further comprises configuring the MR system in a configuration that is operable to acquire a T2-weighted image of at least the portion of the ROI.

One embodiment of the present disclosure further comprises configuring the MR system in a configuration that is operable to acquire T1-rho data of at least the portion of the ROI.

One embodiment of the present disclosure further comprises configuring the MR system in a configuration that is operable to acquire an MR spectroscopy data from at least the portion of the ROI.

One mode of the present disclosure further comprises configuring a CT system in a configuration that is operable to perform a CT imaging operation on at least a portion of the ROI corresponding with the shape.

One mode of the present disclosure further comprises configuring an X-ray system in a configuration that is operable to perform an X-ray imaging operation on at least a portion of the ROI corresponding with the shape.

One mode of the present disclosure further comprises configuring a nuclear imaging system in a configuration that is operable to perform a nuclear imaging operation on at least a portion of the ROI corresponding with the shape.

One mode of the present disclosure further comprises configuring a PET imaging system in a configuration that is operable to perform a PET imaging operation on at least a portion of the ROI corresponding with the shape.

One mode of the present disclosure further comprises configuring a medical diagnostic system in a configuration that is operable to perform a medical diagnostic imaging operation on at least a portion of the ROI corresponding with the shape.

According to one embodiment of the present disclosure, the medical diagnostic system comprises a combination of multiple unique imaging modalities comprising first and second modalities, and further comprising configuring at least the first modality in a respective first configuration to perform a first operation on at least the portion of the ROI.

One embodiment of the present disclosure further comprises configuring the second modality in a respective second configuration to perform a second operation on at least the portion of the ROI.

One variation of the present disclosure further comprises:
configuring the first modality in a configuration that is operable to acquire the electronic image;
defining the ROI based upon the electronic image acquired by the first modality; and
configuring the second modality in the second configuration based upon the electronic image acquired by the first modality.

According to one variation of the present disclosure, the medical diagnostic system comprises a combination MR/CT, PET/CT, or PET/MR system.

According to one mode of the present disclosure, the body portion comprises a foramen.

According to one mode of the present disclosure, the body portion comprises a body space defined by at least one tissue wall.

According to one mode of the present disclosure, the body portion comprises at least a portion of an organ.

According to one mode of the present disclosure, the body portion comprises at least a portion of a prostate gland.

According to one mode of the present disclosure, the body portion comprises at least a portion of a breast.

According to one mode of the present disclosure, the body portion comprises at least a portion of a brain.

According to one mode of the present disclosure, the body portion comprises at least a portion of a tumor.

According to one mode of the present disclosure, the body portion comprises at least a portion of a bone.

According to one mode of the present disclosure, the electronic image comprises an image coordinate system, and further comprising defining the ROI in image coordinates.

One embodiment of the present disclosure further comprises prescribing the shape in image coordinates.

One variation of the present disclosure further comprises prescribing the shape in world coordinates.

One mode of the present disclosure further comprises processing the electronic image to define multiple ROIs in the electronic image.

According to one embodiment of the present disclosure, the multiple ROIs correspond to multiple intervertebral discs.

One embodiment of the present disclosure further comprises prescribing a plurality of shapes to fit within the plurality of ROIs in the electronic image.

One mode of the present disclosure further comprises:
using the one or more processors to process the electronic image to determine a recommended shape to fit within the ROI; and
allowing a user to accept the recommended shape or to manually prescribe a second shape as the shape.

According to one embodiment of the present disclosure, the allowing comprises allowing the user to modify the recommended shape to prescribe the second shape as the shape.

According to one mode of the present disclosure, the electronic image is of a first imaging mode, the method further comprising modifying the defined ROI or the prescribed shape based on an additional electronic image of a second imaging mode different than the first imaging mode.

According to one mode of the present disclosure, the electronic image is of a first imaging mode, the method further comprising comparing the defined ROI or the prescribed shape to information derived from an additional electronic image of a second imaging mode different than the first imaging mode.

One aspect of the invention is a method for determining patient motion during a medical procedure on a patient, comprising:
comparing a first image from the patient acquired at a first time relative to the procedure against a second image acquired from the patient at a second time relative to the procedure;
observing a difference between the first and second images based upon the comparison; and
determining patient motion between the first and second times based upon the difference between the first and second images. This aspect of the disclosure can be combined with the other aspects, modes, embodiments, variations, and features described herein to form various combinations and sub-combinations.

One mode of the present disclosure further comprises mapping a voxel prescribed in a region of interest (ROI) based upon the first image onto same coordinates in the second image.

One embodiment of the present disclosure further comprises determining change of voxel location relative to the ROI in the first and second images.

Another aspect of the present disclosure is a method for determining motion of a defined region of interest (ROI) of a body of a patient from a first position to a second position during a medical procedure being conducted on a patient. This method according to one mode comprises comparing a first image from the patient acquired at a first time relative to the procedure against a second image acquired from the patient at a second time relative to the procedure, wherein the first and second images comprise the ROI; observing a difference between the first and second images based upon the comparison; and determining motion of the ROI between the first and second positions at the first and second times, respectively, based upon the difference between the first and second images.

Another mode of this aspect comprises re-prescribing a voxel prescribed in a first prescription within the ROI based upon the first position in the first image onto same voxel prescription coordinates in a second prescription relative to the ROI in the second position in the second image.

Another mode comprises determining change of voxel location relative to the ROI in the first and second images.

According to another mode, the determining comprises quantifying an extent of patient motion to a value.

One embodiment of this mode comprises comparing the value to a reference value to determine a difference value.

Another embodiment further comprises adjusting the procedure based upon the difference value. According to one further embodiment, this adjusting comprises terminating the procedure based upon the difference value. According to another embodiment, the adjusting comprises changing a spatial orientation or direction parameter of the procedure initially registered with the ROI in the first position to register the procedure with the ROI in the second position.

According to another embodiment, observing the difference is based upon adjusting one of the first and second images in overlay to the other of the first and second images while performing a correlation comparison of an image parameter between the first and second images, determining the adjustment corresponding with maximum correlation of the image parameter, and deriving the difference from the adjustment. In one further embodiment, the correlation comparison is based upon a registration of a segmented structure between the first and second initial images. In another further embodiment, the segmented structure comprises a border or shape of the ROI.

One aspect of the present disclosure is a medical device system, comprising one or more processors configured to run computer instructs stored on one or more computer readable media to perform one or more of the actions described herein. This aspect of the disclosure can be combined with the other aspects, modes, embodiments, variations, and features described herein to form various combinations and sub-combinations.

One aspect of the present disclosure is one or more computer readable media comprising computer instructions configured to cause one or more computer processors to perform one or more of the actions described herein. This aspect of the disclosure can be combined with the other aspects, modes, embodiments, variations, and features described herein to form various combinations and sub-combinations.

According to one mode of the present disclosure, the defining the ROI in the electronic image comprises:
accessing the electronic image;
processing the electronic image, using one or more computer processors, to emphasize pixels associated with at least one structure useful for identifying the region of interest; and
identifying a population of pixels in the electronic image associated with the at least one structure.

One embodiment of the present disclosure further comprises:
selecting one or more image coordinates based on the population of pixels; and
converting the image coordinates to world coordinates corresponding to at least a portion of the region of interest.

Another aspect of the present disclosure comprises one or more non-transitory computer readable media comprising computer instructions configured to cause one or more computer processors to perform the following actions: performing image fusion between multiple initial electronic images of a region of interest (ROI) of a body of a patient to generate a fused image providing an enhanced definition of the ROI or border thereof relative to the initial images; and processing the fused image as the electronic image according to any one or more of the other aspects, modes, embodiments, or variations elsewhere herein disclosed. In various embodiments, processing the fused image comprises obtaining information relating to the ROI, prescribing a shape within the ROI, configuring a medical system to be used in performing an operation on the ROI, or defining the ROI between bones as described elsewhere herein.

According to one mode of this aspect, the initial images comprise magnetic resonance images.

According to one embodiment of this mode, the initial images comprise a T1-weighted and a T2-weighted image.

In another mode, performing the image fusion comprises differencing the initial images; and the fused image comprises a differenced image.

In another mode, performing the image fusion comprises blending the initial images; and the fused image comprises a blended image. In one embodiment of this mode, blending the initial images comprises alpha-blending; and the blended image comprises an alpha-blended image.

In another mode, the non-transitory computer readable media comprises further computer instructions configured to cause the one or more processors to perform actions comprising enhancing contrast along a population of pixels corresponding with a border of the ROI using the fused image.

Another aspect of the current disclosure is a method for automated diagnostic image processing, comprising performing image fusion between multiple initial electronic images to generate a fused image; post-processing the fused image as the electronic image, such as according to any of the other aspects, modes, embodiments, or variations elsewhere herein disclosed; and causing one or more computer processors to perform the image fusion and post-processing via a set of computer instructions from one or more non-transitory computer readable media. In various embodiments, post-processing the fused image comprises obtaining information relating to the ROI, prescribing a shape within the ROI, configuring a medical system to be used in performing an operation on the ROI, or defining the ROI between bones as described elsewhere herein.

In one mode of this aspect, the initial electronic images comprise magnetic resonance images. According to one embodiment of this mode, the initial electronic images comprise a T1-weighted and a T2-weighted image.

In another mode, performing the image fusion comprises differencing the initial images; and the fused image comprises a differenced image.

In another mode, performing the image fusion comprises blending the initial images; and the fused image comprises a blended image. According to one embodiment of this mode, blending the initial images comprises alpha-blending; and the blended image comprises an alpha-blended image.

In another mode, the actions of the processor conducted according to the computer instructions further comprise enhancing contrast along a population of pixels corresponding with a border of the ROI via the fused image.

The aspects, modes, embodiments, variations, and features noted above, and those noted elsewhere herein, can be combined to form various combinations and sub-combinations, even where not specifically discussed. For example, the methods and systems disclosed herein can perform one or more of the operations shown in FIG. 5 or described herein alone or with various combinations of the other operations shown in FIG. 5 or disclosed herein.

As would be apparent to one of ordinary skill, use of particular terms at specific places in this disclosure above shall be considered to relate consistently to similar features as other uses of same terms in other places in this disclosure, including in context of providing certain combinations between then and which are contemplated hereunder (though such combinations are not necessarily required limitations); provided, however, to the extent such different uses are compatible and would not create inconsistencies (in which case the different uses of the terms should be considered independently of each other).

BRIEF DESCRIPTION OF THE DRAWINGS

Various features, aspects, and advantages of the present disclosure will now be described with reference to the drawings of embodiments, which embodiments are intended to illustrate and not to limit the disclosure.

FIG. 8A is a flow diagram showing the ROI location and isolation portions of the flowchart of FIG. 5.

FIG. 8B is the mid-sagittal MRI image of FIG. 6 with increased contrast to highlight the intervertebral discs and showing default ROI areas.

FIG. 8C is the mid-sagittal MRI image with ellipsoids surrounding the automatically identified disc locations.

FIG. 10A is a flow diagram showing the 3D voxel formation portions of the flowchart of FIG. 5.

FIG. 10B shows a 3D voxel relative to two transverse mid-sagittal and mid-coronal 2D MRI images.

DETAILED DESCRIPTION OF SOME EMBODIMENTS

Figure 1:
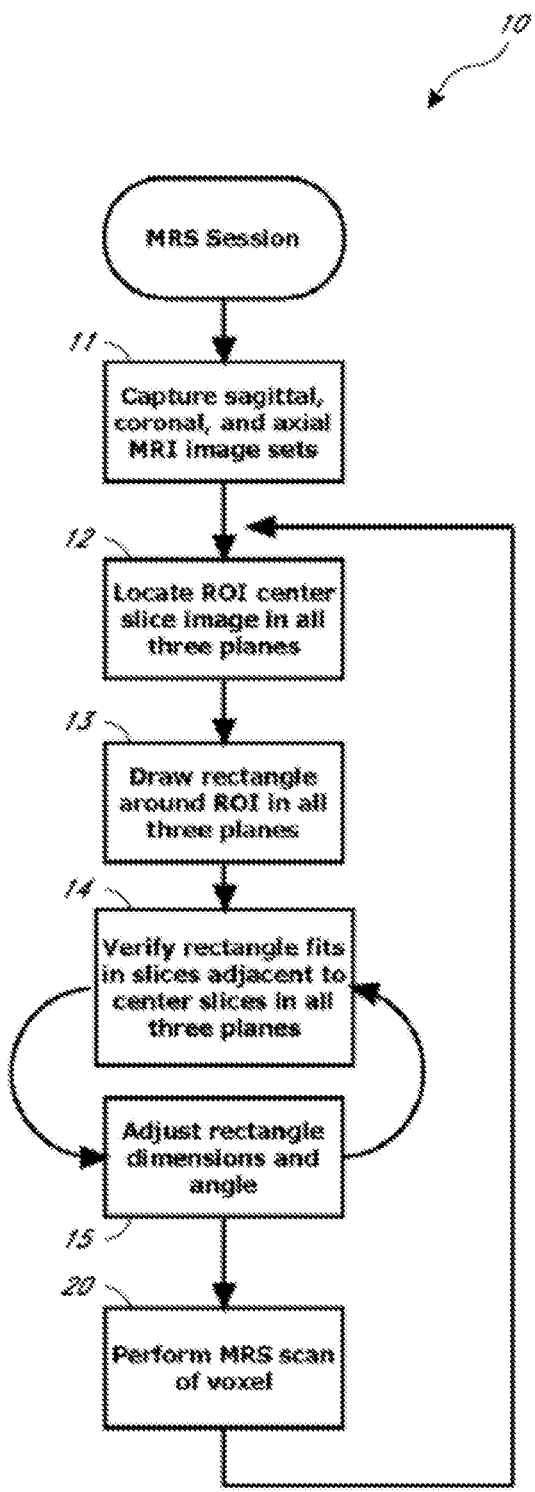
FIG. 1 is a flowchart that shows a method for performing manual voxelation.

Various embodiments disclosed in the present disclosure relate to clinical magnetic resonance spectroscopy (MRS), in particular single voxel MRS, and still more particularly to the automated prescription of voxels within regions of interest where MRS is to be performed, such as, for example, intervertebral discs. One example application of the present disclosure is to single voxel MRS of the intervertebral discs of the lumbar spine, such as the three to five lower lumbar discs, such as for the purpose of diagnosing disc degeneration or discogenic pain. The systems and methods described herein can be used in the application of MRS to diagnose chronic, severe discogenic low back pain by identifying discs that are more likely to be painful versus non-painful though chemical signature analysis of disc tissue.

Magnetic resonance imaging (MRI), and in particular magnetic resonance spectroscopy (MRS), uses a combination of radiofrequency (RF) pulses and dynamic magnetic fields to energize a target volume of material resulting in the generation of resonant frequencies that are characteristic of the chemical constituents within the energized volume. In a clinical MRS application, the target volume or three dimensional (3D) volume is referred to as a voxel (e.g., a single point or pixel with volume). As used herein the term voxel can refer to the three dimensional target volume. In some embodiments, a two dimensional voxel shape can be a slice or cross section of the three dimensional voxel volume. Although various embodiments are disclosed herein in connection with forming a voxel for a three dimensional volume, it will be understood that the embodiments also relate to forming two dimensional shape associated with a two dimensional portion of the ROI. In some embodiments, information identifying a ROI in only a two dimensional area can be useful. In clinical MRS, voxels are typically defined or prescribed using the sagittal, coronal, and axial or oblique axial two dimensional (2D) MRI images that include the region of interest ("ROI"). Using a graphical interface, the MRS technician manually draws or enters coordinates for a pattern (typically a rectangle) in each of the three plane images, for example according to various present embodiments to outline the nucleus of a lumbar disc. The graphical interface converts the 2D patterns in multiple transverse (in some cases orthogonal) planes into a 3D volume or voxel.

As a prescribed MRS voxel defines the volume of interest ("VOI") where MRS signatures are taken, its location and tissue defined therein defines what signatures are captured. If tissue within the ROI is distinctive from tissue bordering the ROI, mis-prescription of the voxel in terms of size and/or location to extend beyond the ROI could confound MRS results by capturing unwanted signal from the bordering tissue unintended to be "voxelated" for the MRS signature acquisition. Furthermore, if it is not readily apparent that the voxel was mis-prescribed, then the MRS spectrum resulting from the mis-prescribed acquisition and including bordering tissue signatures could be misinterpreted to represent the intended tissue within the target ROI itself. If signatures from bordering tissues are not related to "biomarker" chemicals of interest for a particular diagnosis, this may be less concerning in such circumstances. However, if signatures from bordering tissues relate directly or indirectly (such as by overlapping MRS signature regions between different chemicals) to such biomarker signals being targeted for MRS analysis of the ROI, mis-prescription of the voxel could lead to mis-diagnosis of the tissue within the intended ROI.

Still further, aside from bordering tissue issues, voxel volume will typically directly correlate with signal strength. A general goal of most MRS voxel prescriptions is thus to maximize voxel volume within a desired ROI for a tissue, so as to increase the signal strength, while still excluding bordering tissues or structures of potentially different chemical composition relevant to MRS spectral acquisitions from the ROI.

In many applications, a rectilinear voxel may fit easily into a large ROI. This may be the case for example in many cases involved in applications for the brain or breast where the voxel volume is a small percentage of the ROI volume. However in many certain other applications, such as intervertebral discs, the ROI may be rather small and non-rectilinear and may consist of compound surfaces (e.g., having different curvature and/or shape at different portions of the perimeter of the ROI, such as nodules, which in some cases do not correspond to a smooth geometric equation or curve), such as resulting in a more ellipsoidal type shape (e.g. intervertebral discs). As such, manual prescription of one shape inside of another may not be readily optimized. A rectangle that is fitted for a particular planar slice through an ellipsoid ROI may not fit in the ROI of an adjacent slice, resulting in the voxel dimensions exceeding the shape of the ROI. This is one illustrative example of a mis-prescription that would be desirable to avoid. To avoid a voxel mis-prescription, the MRS technician typically verifies that the voxel prescribed in one set of 2D images fits within the adjacent 2D images or slices that encompass the voxel. Even for skilled technicians, this can be challenging to get correct in many cases. Also, the trade off between maximizing voxel volume for optimal signal-to-noise (SNR) ratio, versus excluding bordering different tissue structures, is an exercise in "risk-reward" trade-offs that may be challenging to optimize for a particular case (especially challenging cases, where the ROI is small and bordering structures can introduce significant error if captured, as is the case for intervertebral discs).

In the particular case of a voxel intended to capture an intervertebral disc for MRS chemical signature analysis, and more specifically the nucleus of an intervertebral disc, this structure can be bordered on some or all sides by different structures that are chemically distinct from the intended disc tissue. This is in particular the case superiorly (vertically above) and inferiorly (below) the disc, where vertebral body end-plates reside. These structures involve, among other constituents, bone marrow which are rich in lipid that has an MRS signature that overlaps with and may mask other target chemicals (such as for example lactic acid and alanine). A mis-prescribed voxel for a disc nucleus MRS exam thus may contain tissue from the vertebral endplate adjacent to the nucleus resulting in resonant frequencies from both tissues. The MRS signatures (e.g., lipid) from tissue surrounding the ROI can compromise the ability to assess overlapping chemicals of the ROI (e.g., lactic acid and alanine), in addition to simply representing the wrong tissue. Additionally, in some cases, a degenerative painful disc itself may contain lipid. To the extent a lipid signal is representative only of bordering bone or end-plates and not the intervertebral disc, a lipid signature in a resulting acquired spectrum could indicate a mis-prescription and motivate a re-prescription in a repeat scan, such as by moving or shrinking the voxel. However, because lipids and associated MRS signatures can be present both in some actual disc tissues, and in a mis-prescription involving bordering vertebral bodies or the end-plates, the ability to recognize whether a mis-prescription occurred based on a lipid signal may be compromised in some cases. Thus, in some cases, the identification of a lipid signature in an acquired spectrum is not useful as an indicator of voxel mis-prescription, while in other cases a lipid signature may be indicative of a voxel mis-prescription. In some embodiments, detection of a lipid signal over a threshold level can cause an MRS acquisition to be repeated (with a voxel of the same or different size), disregarded, flagged for user review, and/or further analyzed for accuracy.

Further to the issues elsewhere noted surrounding manual voxel prescriptions, the process of defining single voxels may be very time consuming. For example, in a single voxel MRS exam of three lower lumbar discs, if each voxel prescription took from about 2.5 to about 5 minutes, that represents between about 7.5 to about 15 minutes total time for voxelation during the exam. For an actual pulse sequence acquisition that may take for example about 2.5 to about 5 minutes, or 7.5 to about 15 minutes total "scan time," that manual voxelation essentially doubles the time of the exam (not accounting for other activities, such as imaging sequences, shimming, etc.). Where mis-prescriptions occur and are caught, rescanning can further increase the time of the exam.

Time means money in imaging, and healthcare costs have become among the most prominent issues in all of modern society world-wide. At least near the top of such issues reside the rising costs of imaging. Moreover, time that a patient resides in an MRI environment for an exam, or "in the tube," is limited due to patient comfort and other concerns. Over extended exam times, patients will often become more restless, thus more likely to move, and movement can confound an MR exam (e.g. patient movement after a voxel prescription can move the patient's tissues while the voxel location remains fixed in MR machine coordinates, effectively creating a voxel mis-prescription). Furthermore, patients such as low back pain patients may be in tremendous discomfort to begin with. If the manual process were replaced by one that was at least partially automated, significant time could be saved. For illustration, by reference to the example immediately above, replacing manual voxelation with a fully automated process could potentially cut the time of the exam by as much as 25-50%.

Manual voxelation thus represents a human operator-dependent process, and the results of the MRS exam can directly (and in some cases critically) depend on correct performance of the manual voxelation. Thus, manual voxelation introduces the risk of human error. When the risk of human error is high, and the impacts of the potential error can be critical, the need to find a solution to remove this potential opportunity and source for human error becomes that much more important. This does not necessarily reflect badly on the human operators themselves. Manual voxelation for single voxel spectroscopy may be very difficult to get right, especially in challenging MRS applications in small defined tissue regions. Inter-operator variability could be high even between the most highly skilled and diligent of operators, especially in particularly challenging cases. Thus, an automated voxelation process can reduce or eliminate the occurrence of human error and can increase consistency and predictability in the voxelation process and in the MRS results.

Accordingly, one aspect of this disclosure provides a useful solution to replace, or at least augment, manual voxel prescription (e.g., for single voxel MRS exams) by an at least partially automated voxelation system and method. In fact, in some embodiments herein described, the voxelation is either fully or nearly fully automated. According to one particular benefit, this can mitigate certain associated potential risks and issues that may impact single voxel MRS exams. According to another benefit, it shortens the time necessary for the voxelation portion of the exam, which shortens the time for the overall exam, which may result in more efficient delivery of healthcare, more patient comfort, and more robust results.

In particular, one mode of this aspect provides a system and method to automate the voxel prescription process by identifying the boundaries of the ROI in a set of 2D images that encompass the ROI, creating a 3D model of the ROI, and fitting a rectilinear shape/voxel within the ROI. The resulting dimensions and coordinates of the voxel are then presented to the MRS technician for entry into the graphical user interface. The system may also process/define multiple voxels for multiple ROI within a common field of view (FOV) simultaneously. Thus, although many embodiments are described herein in connection with single voxel MRS, the systems and methods may also be applied to multivoxel MRS (e.g., for multiple ROI). In the example of lower lumbar applications, voxels may be automatically prescribed for multiple (e.g., all five) lower lumbar discs.

Some embodiments of the present disclosure can be used in automating the voxel prescription of an intervertebral disc, such as for MRS exams to provide diagnostic information related to disc degeneration and/or discogenic pain.

FIG. 1 shows the flow process of an MRS session 10 that uses manual voxel prescription. The process is illustrated by blocks 11-15 shown in FIG. 1 as described in further detail below. Detailed numbers such as for dimensions etc., as indicated immediately below and elsewhere herein this disclosure, are provided in order to describe specific illustrative embodiments only, and are provided as "about" approximations, and may vary from such specified values as apparent to one of ordinary skill.

At block 11, sagittal, coronal, and axial or oblique axial MRI image sets can be captured. For example, a series (e.g., 13 slices) of high resolution T2-w MRI images of the ROI in the sagittal plane can be captured using a field of view (FOV) of 40 cm×40 cm and a 4 mm slice thickness. A series (e.g., 13 slices) of high resolution T2-w MRI images of the ROI in the coronal plane can be captured using a field of view (FOV) of 40 cm×40 cm and a 4 mm slice thickness. A single high resolution T2-w MRI image of the ROI in the axial or axial oblique plane (e.g., typically more angulated at the L5/S1 level) can be captured using a field of view (FOV) of 40 cm×40 cm and a 4 mm slice thickness. It will be understood that MRI images may be produced using various other suitable parameters. Also, in some embodiments, a series of multiple MRI images can be used in the axial or oblique axial plane instead of a single MRI image, and the series of sagittal and coronal MRI images may contain more or fewer than the 13 images described above.

At block 12, the MRI image of the slice that intersects the center of the ROI in the sagittal plane can be identified. Typically, the MRI image having the largest cross-sectional area of the ROI is the slice that intersects the center of the ROI. In a series of 13 MRI images as described above, slice number 7 or 8 will typically intersect the center of the ROI. In some embodiments, this process may be repeated for the MRI images in the coronal plane, to identify the MRI image of the slice that intersects the center of the ROI in the coronal plane. If a series of MRI images are used in the axial or oblique axial plane, an MRI image that intersects the center of the ROI in the axial or oblique axial plane can also be identified. If the axial or oblique axial MRI image set includes only a single image, that single MRI image can be used as the center image.

At block 13, a rectangle can be drawn using the MRI graphical user interface in each of the three planes. For each axis, if an MRI image was identified in block 12 as intersecting the center of the ROI (e.g., having the largest cross-sectional area), that MRI image can be used to draw the rectangle for that axis.

At block 14, the system can present the adjacent MRI images from the MRI image sets with the drawn rectangle projected onto the image. The user can observe the projected rectangle in some or all of the MRI images in the sagittal MRI image set to verify that the rectangle fits inside the ROI for each slice in the sagittal orientation. The user can observe the projected rectangle in some or all of the MRI images in the coronal MRI image set to verify that the rectangle fits inside the ROI for each slice in the coronal orientation. If multiple images are used in the axial or axial oblique angle, the user can observe the projected rectangle in some or all of the MRI images in the axial or oblique axial MRI image set to verify that the rectangle fits inside the ROI for each slice in the axial or oblique axial orientation.

At block 15, if needed, the user can adjust the dimensions, coordinates, and angle of the rectangle so as to keep the rectangle within the ROI. It will be understood that in some embodiments, block 15 can be omitted, for example, if no adjustments to the rectangle are needed after the initial rectangle designation. In some cases, the user may reduce the size of the rectangle so as to exclude area outside the region of interest. The user may also increase the size of the rectangle so as to capture more volume of the region of interest. The user may also change the angle or orientation of the rectangle so as to better fit the volume of the ROI.

If the rectangle is adjusted in block 15, the process can repeat block 14 to confirm that the adjusted rectangle fits into the ROI in some or all of the slices of the MRI images sets. In some embodiments, the user can repeat blocks 14 and 15 (multiple times if needed) until a rectangle is defined that covers a large portion of the ROI but does not extend outside the ROI. In some embodiments, the user may first adjust the rectangle in the sagittal and coronal directions and once satisfied with their positioning can confirm in the single axial or oblique axial plane MRI image that the rectangular dimensions are contained within the ROI in the axial or oblique axial direction.

Once the user is satisfied with the rectangle dimensions and angles, the process can proceed to block 20 and perform the MRS scan. Blocks 11 through 20 can then be repeated for additional ROIs (e.g., additional intervertebral discs) to be scanned.

Figure 2A:
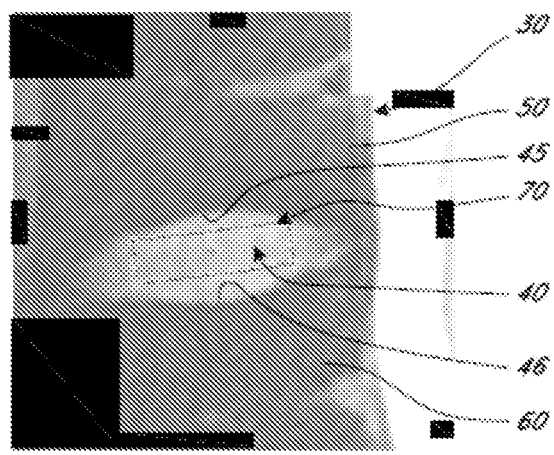
FIG. 2A shows a mid-sagittal 2-dimensional MRI image of an intervertebral disc with a voxel manually applied thereto.
Figure 2B:
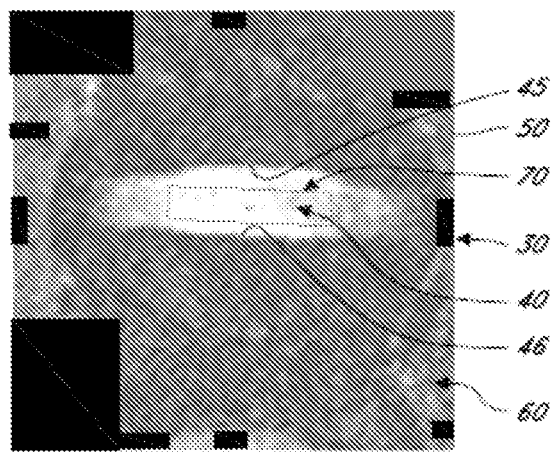
FIG. 2B shows a mid-coronal 2-dimensional MRI image of an intervertebral disc with a voxel manually applied thereto.
Figure 2C:
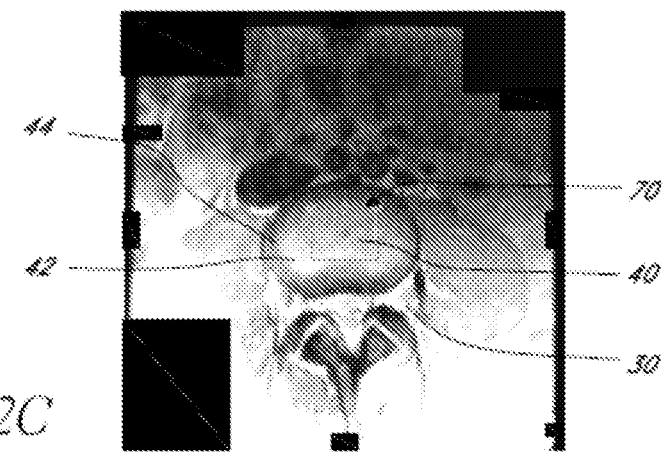
FIG. 2C shows an axial or oblique axial 2-dimensional MRI image of an intervertebral disc with a voxel manually applied thereto.

FIGS. 2A-C show mid-sagittal (FIG. 2A), mid-coronal (FIG. 2B), and axial or oblique axial (FIG. 2C) 2-dimensional (2D) planar views of MRI images taken during imaging phase of one illustrative MRS exam of a human subject's spine 30, including a disc 40 bordered by superior and inferior end-plates 45, 46 between disc 40 and superior and inferior vertebral bodies 50, 60 located above and below disc 40. The disc 40 can include a disc nucleus 42 and a disc annulus 44. Shown superimposed on these planar MRI images is a rectangular voxel 70 drawn per a manual prescription as described above.

An example of the potential risks associated with manual prescription is illustrated by reference to FIGS. 3A-3D and 4A-4D, which illustrate another MRS exam of another subject where one MRS exam conducted according to a mis-prescribed voxel (FIGS. 3A-3D) is compared against the MRS results of another MRS exam conducted with a more appropriate prescription (FIGS. 4A-4D).

Figure 3A:
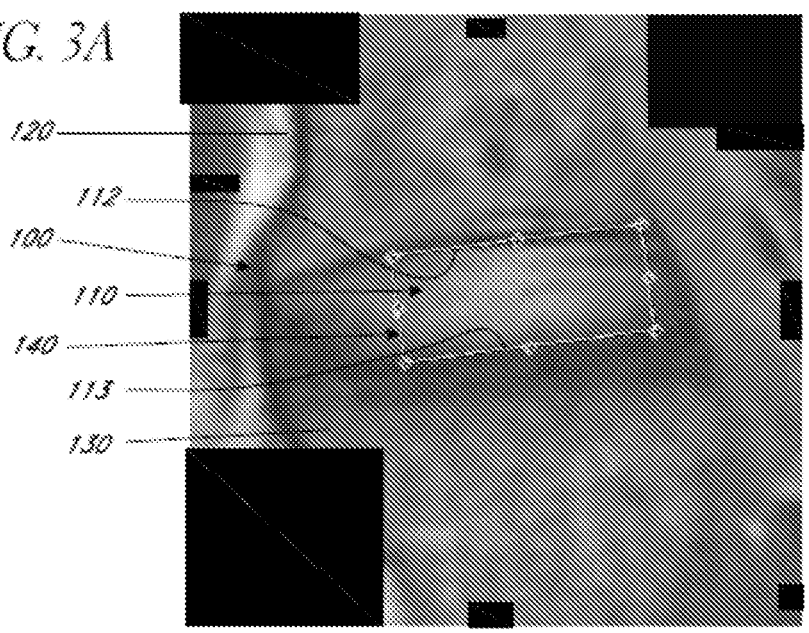
FIG. 3A shows a mid-sagittal 2-dimensional MRI image of an intervertebral disc with a mis-prescribed voxel applied thereto.
Figure 3B:
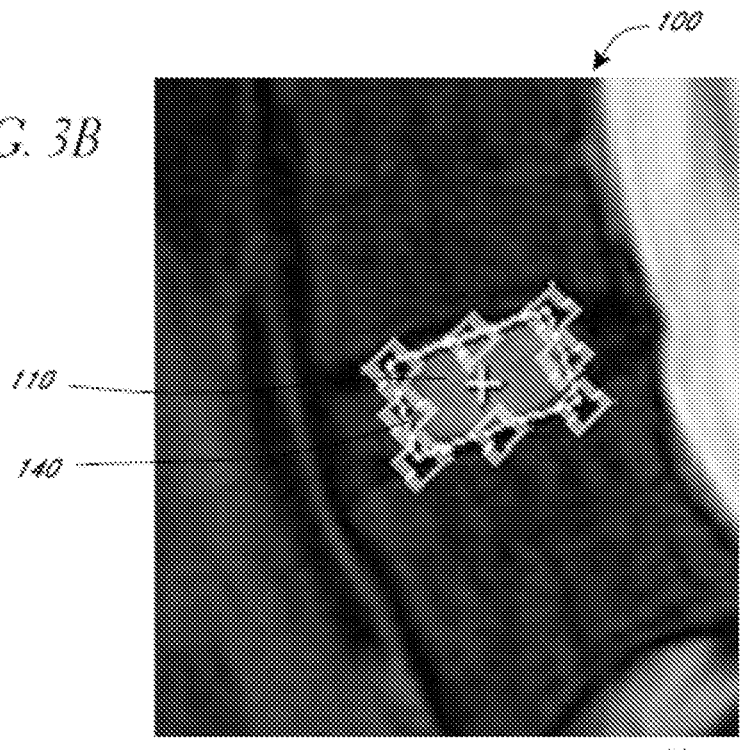
FIG. 3B shows a mid-coronal 2-dimensional MRI image of an intervertebral disc with a mis-prescribed voxel applied thereto.
Figure 3C:
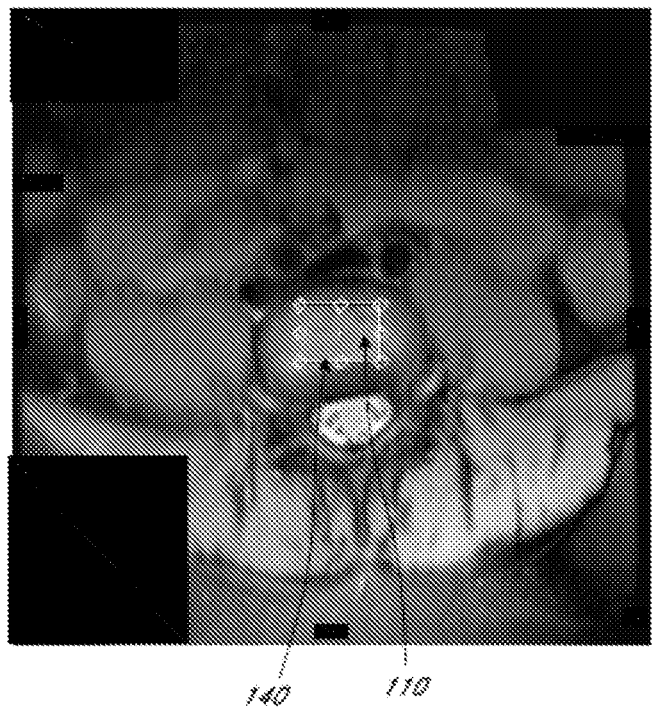
FIG. 3C shows an axial or oblique axial 2-dimensional MRI image of an intervertebral disc with a mis-prescribed voxel applied thereto.

More specifically, FIGS. 3A-3C show mid-sagittal (FIG. 3A), mid-coronal (FIG. 3B), and axial or oblique axial (FIG. 3C) 2-dimensional (2D) planar views of MRI images taken during imaging phase of an illustrative MRS exam of a human subject's spine 100, including a disc 110 bordered by superior and inferior end-plates 112, 113 between disc 110 and superior and inferior vertebral bodies 120, 130 located above and below disc 110. Shown superimposed on these planar MRI images is a rectangular voxel 140 drawn per a manual prescription as described above. The voxel 140 as shown in FIG. 3A potentially impinges on one or both of end-plates 112, 113. An MRS exam per this manual voxel prescription, conducted according to an MRS pulse sequence and post-processing system and method similar to that described in PCT Patent Publication No. WO 2011/047197, produced the MRS spectrum 150 shown in FIG. 3D. MRS spectrum 150 includes a relatively narrow and distinctive n-acetyl aspartate (NAA) peak 152 typically representative of proteoglycan (PG) in disc nucleus tissues, and a still stronger peak 154 with much wider line width (e.g. broad between opposite sides of the peak, such as at 50% power of peak) that spans across spectral regions 156, 158 associated with lactic acid and alanine, respectively. This strong, broad peak region 154 is characteristic of lipid signal. If and to the extent any lactic acid or alanine signal may or may not contribute to the signal intensity in this region is difficult to ascertain.

Figure 4A:
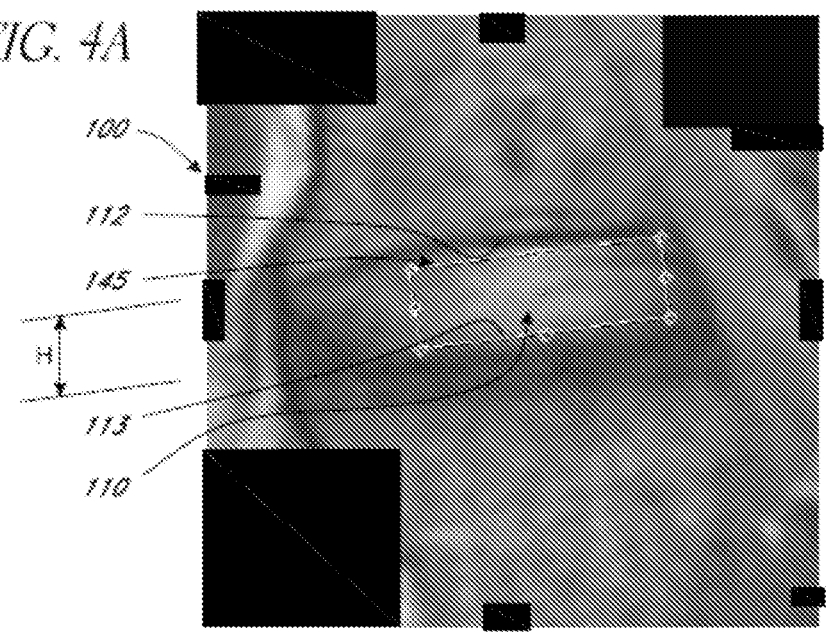
FIG. 4A shows a mid-sagittal 2-dimensional MRI image of an intervertebral disc with a correctly prescribed voxel applied thereto.
Figure 4B:
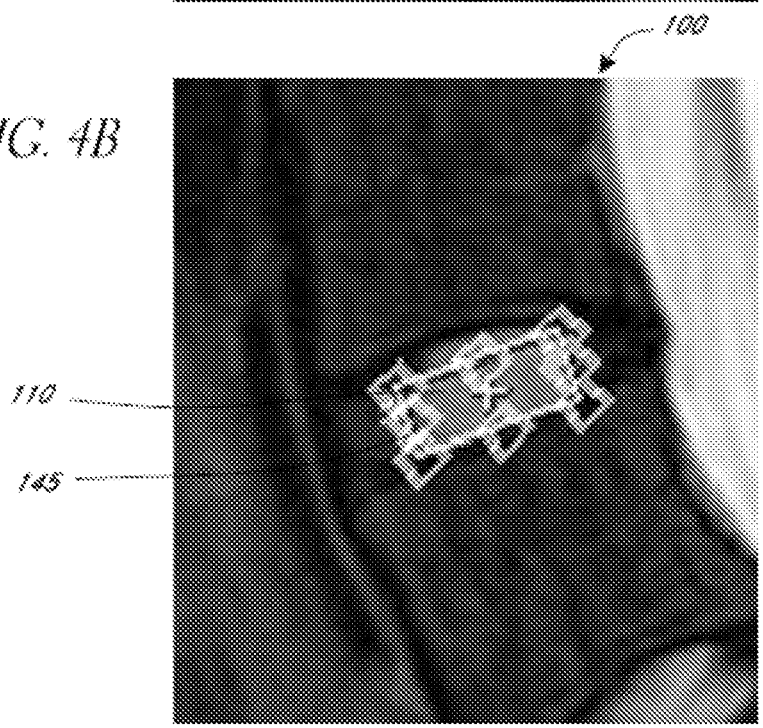
FIG. 4B shows a mid-coronal 2-dimensional MRI image of an intervertebral disc with a correctly prescribed voxel applied thereto.
Figure 4C:
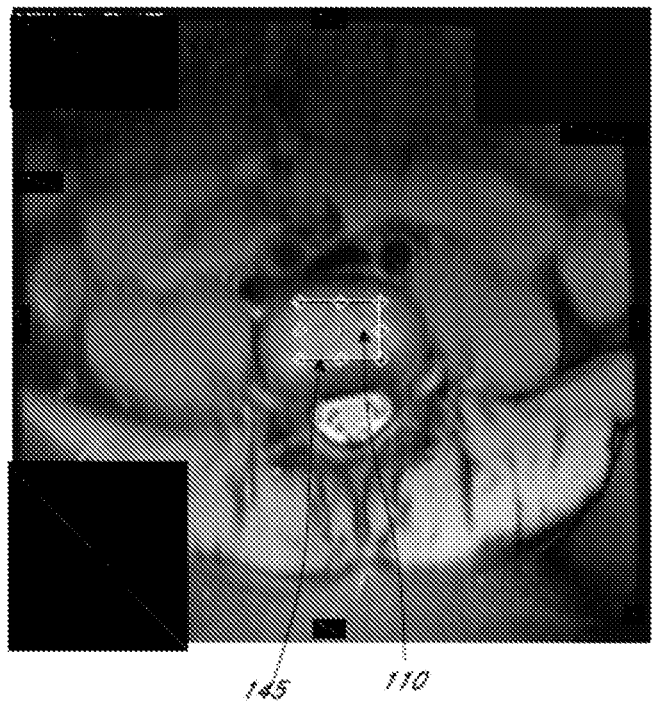
FIG. 4C shows an axial or oblique axial 2-dimensional MRI image of an intervertebral disc with a correctly prescribed voxel applied thereto.
Figure 3D:
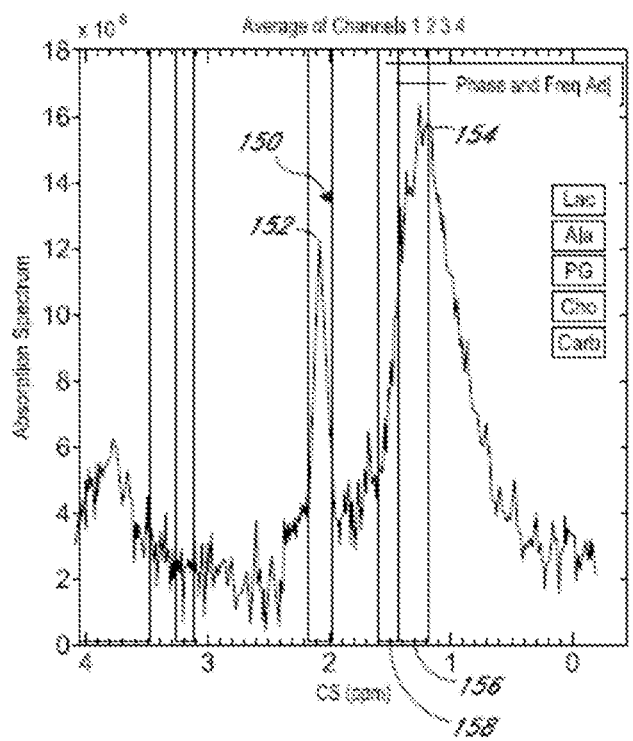
FIG. 3D shows an MRS spectrum resulting from the mis-prescribed voxel of FIGS. 3A-C.
Figure 4D:
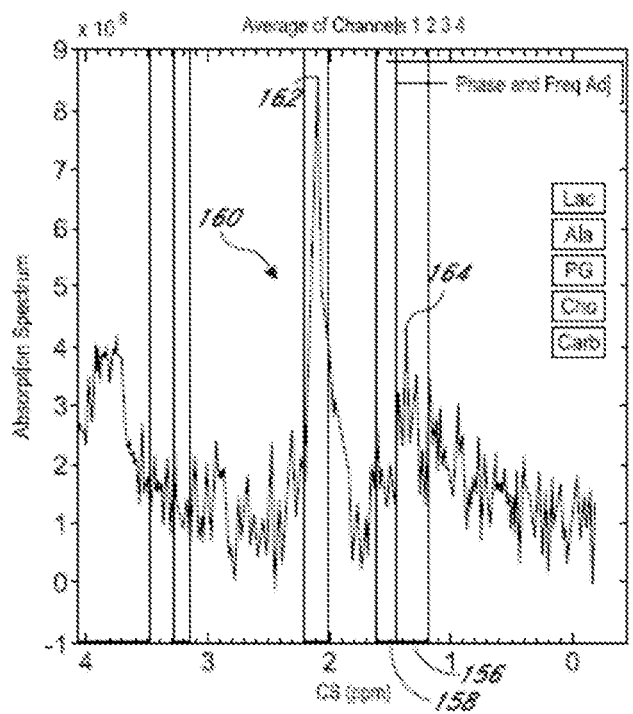
FIG. 4D shows an MRS spectrum resulting from the correctly prescribed voxel of FIGS. 4A-C.

In contrast, FIGS. 4A-4C show similar images for the same spine 100 in the same subject, and in fact during the same MR study session, but for a different MRS exam scan according to a different manual voxel prescription shown at voxel 145. As compared against voxel 140 shown in the prior manually prescribed exam of FIGS. 3A-C, voxel 145 has slightly reduced height vertically across disc 110 and potentially excludes end-plates 112, 113, either of which may have been partially captured by the larger voxel 140 with the larger vertical height dimension in the prior exam. The MRS spectrum 162 acquired and processed for this voxel prescription, according to similar MRS pulse sequence and post-processing methods as reflected in the spectral results shown in FIG. 3D for the prior exam, is shown in FIG. 4D. The Proteoglycan-related n-acetyl aspartate (NAA) peak 162 for spectrum 160 is slightly reduced signal intensity than the similar peak 152 shown in FIG. 3D (between about 8 to 9×10$^8$ for peak 162 versus about 12×10$^8$ for peak 152), as would be expected from a smaller voxel in the second case. However, the overall signal quality is apparent to be much more robust, as the lactate-related and alanine-related spectral ranges 166, 168 include only a slight peak 164, possibly related to small level of lactic acid, but the spectrum 160 appears to be substantially devoid of prominent lipid. By comparison of this first and second voxel prescription results, lipid peak 154 appears to have been the result of captured end-plate contaminant in the MRS spectrum 150 of the "over-prescribed" voxel dimensions in that case.

Figure 5:
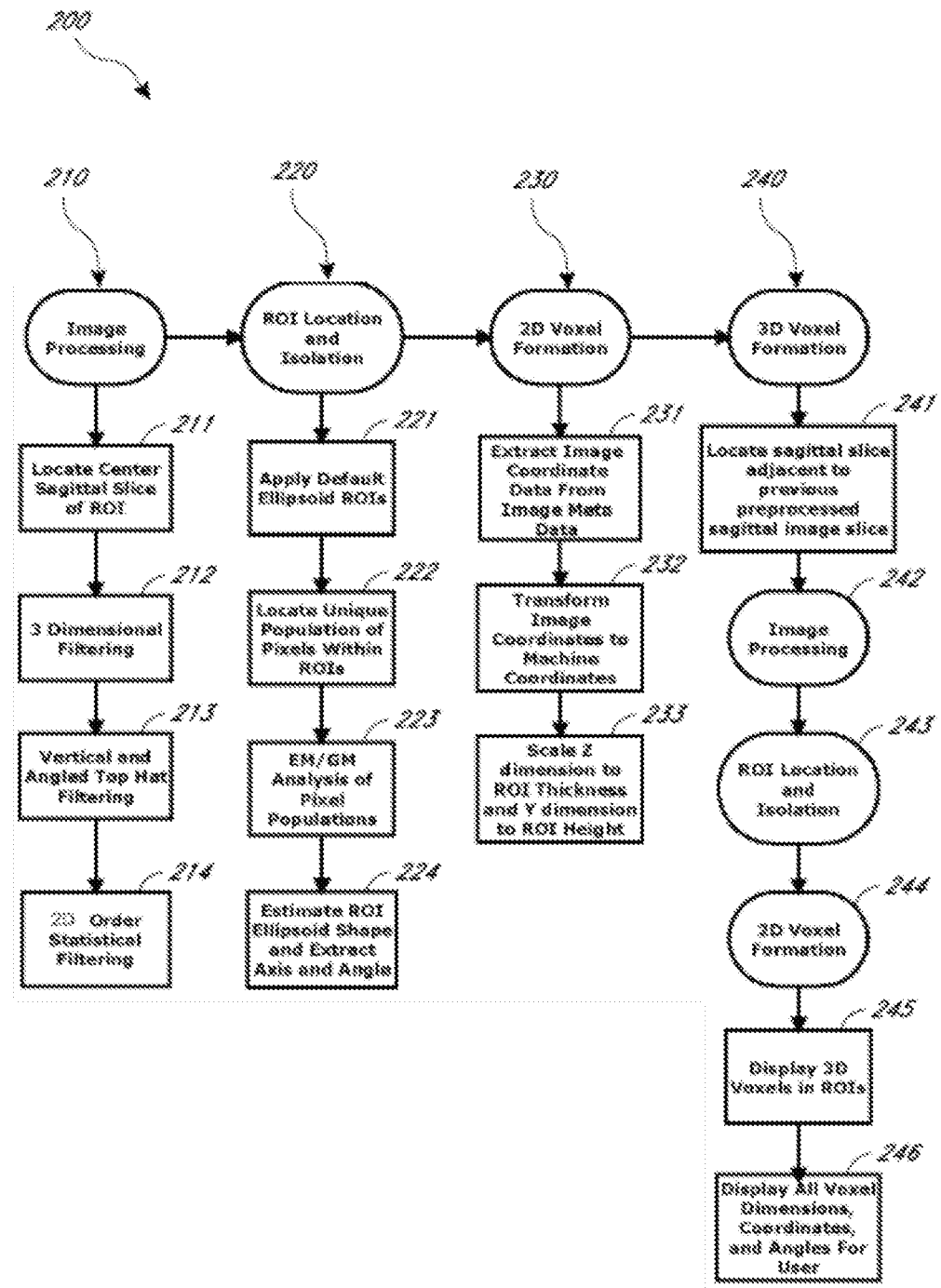
FIG. 5 is a flow diagram for an automated voxelation method.

Example embodiments relating to automated voxelation methods are provided below by reference to FIGS. 5-10B. More specifically, FIG. 5 shows a software flow diagram 200 of an automated voxelation method that can be used by an automated voxelation system, such as the system of FIG. 11 discussed below. As discussed in more detail below, the system can include an MRI/MRS system configured to acquire MRI images of a region of interest in a portion of a patient's body and/or to perform an MRS exam or procedure using the voxelation. The system can also include a computer system that can have a processor and a computer readable medium, which can be configured to execute a program that performs some or all of the method shown in FIG. 5. The method of FIG. 5 can include: image processing 210, including further detailed blocks 211-214 shown; ROI location and isolation 220, including further detailed blocks 221-224 shown; 2D voxel formation 230, including further detailed blocks 231-233 shown; and 3D voxel formation 240, including further detailed blocks 241-246 shown. Various aspects of the method are further illustrated in additional FIGS. 6-10B as follows.

Figure 6:
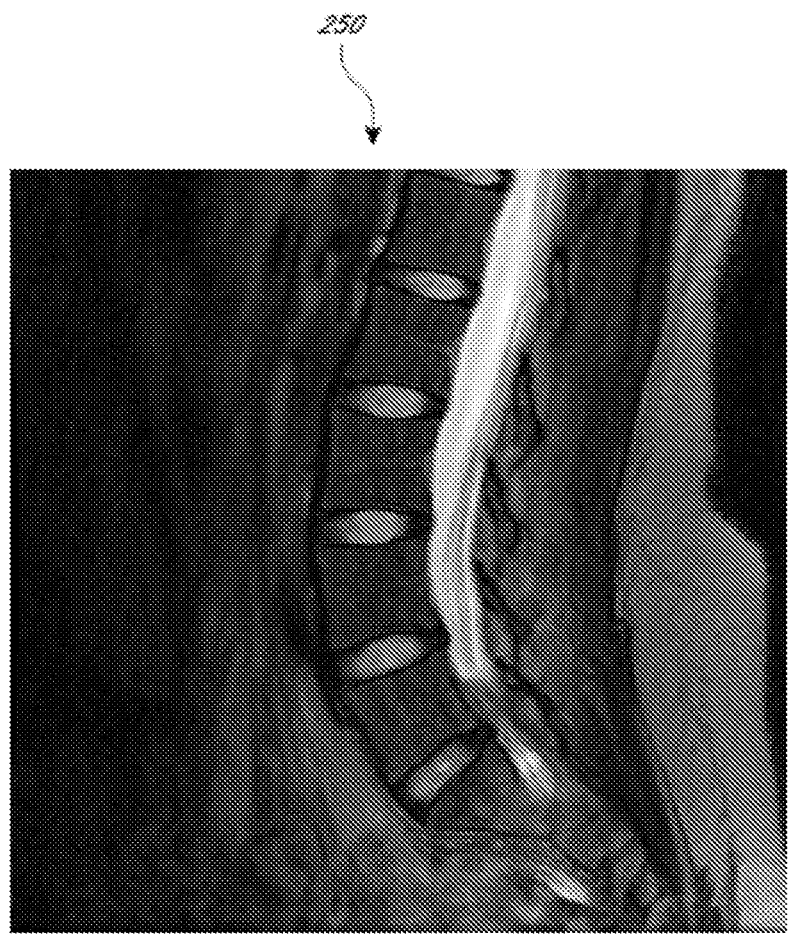
FIG. 6 shows a mid-sagittal 2D planar MRI image of a spine.

FIG. 6 shows a mid-sagittal 2D planar MRI image 250 of the same spine illustrated in the examples of manual voxel prescription shown and described above by reference to FIGS. 3A-4D, but prior to an automated voxel prescription process according to some embodiments.

Figures 7A, 7B:
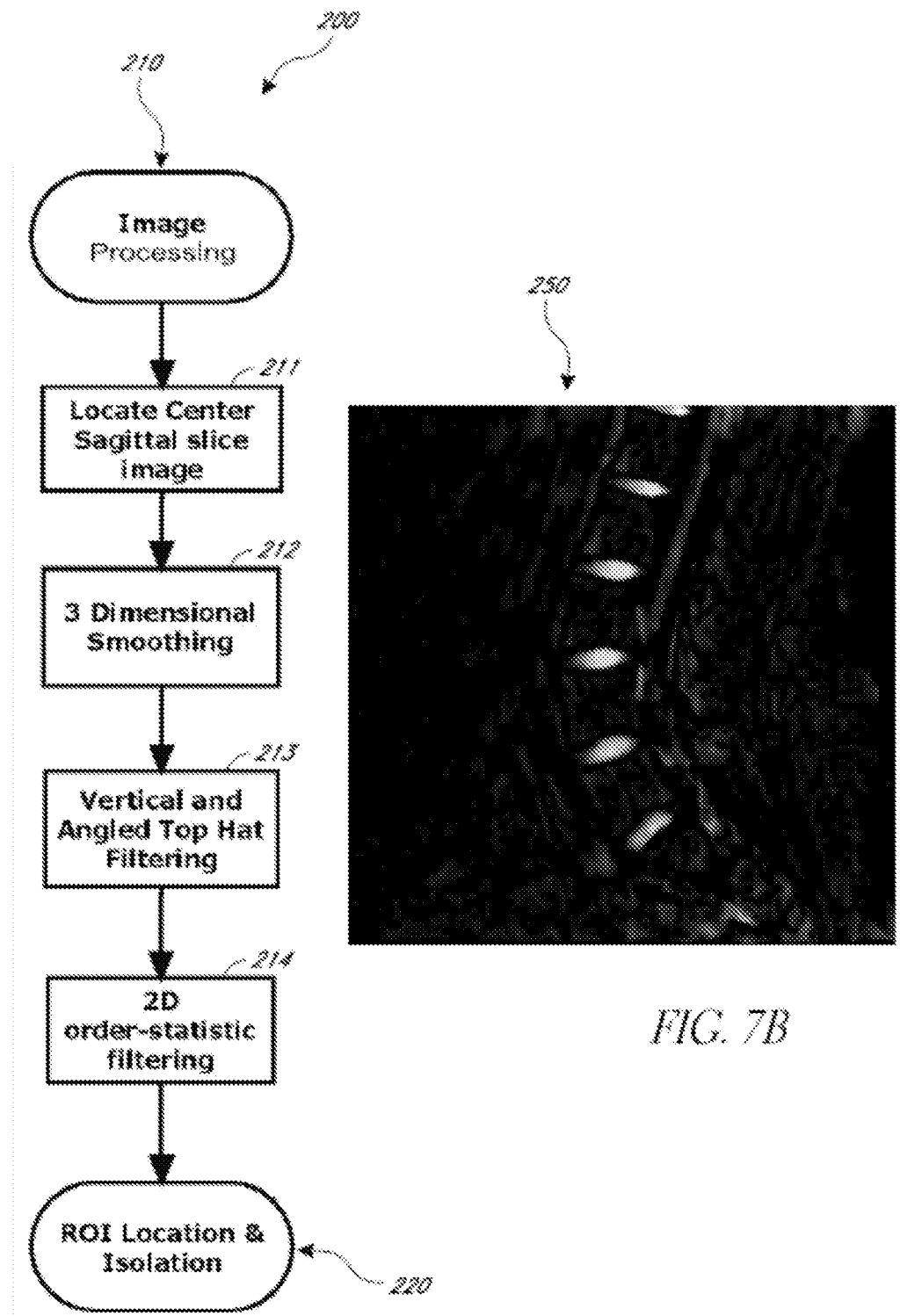
FIG. 7A is a flow diagram showing the image processing portions of the flowchart of FIG. 5.
FIG. 7B is the mid-sagittal MRI image of FIG. 6 after the performance of certain image processing portions.

FIG. 7A shows a flow diagram which reintroduces various detailed blocks 211-214 of image processing phase 210 of the automated voxelation approach illustrated above in FIG. 5. The modified mid-sagittal 2D planar image 250 shown in FIG. 7B illustrates the results from the image processing described.

FIG. 8A reintroduces the flow diagram from FIG. 5 for a ROI location and isolation phase 220 of the automated voxelation program 200, including detailed blocks 221-224. FIG. 8B shows a mid-sagittal 2D planar MRI image 250 as in prior figures for the exemplary spine, but as modified to reflect the results arrived at following completion of the location of a unique population of pixels for the ROI at block 222 shown in FIG. 8A. More specifically, FIG. 8B shows default ellipsoid search areas 260 applied to the image 250, with the unique population of pixels estimated to represent the disc ROI shown at contrast enhanced bright pseudo-ellipsoidal regions 270 within default ellipsoid search areas 260. FIG. 8C shows the same MRI image 250 as prior FIGS. 6, 7B, and 8B above, but as further modified to reflect and plot the estimated ellipsoid shapes 280 generated by the program for the respective disc nucleus regions at block 224 shown in FIG. 8A.

Figures 9A, 9B:
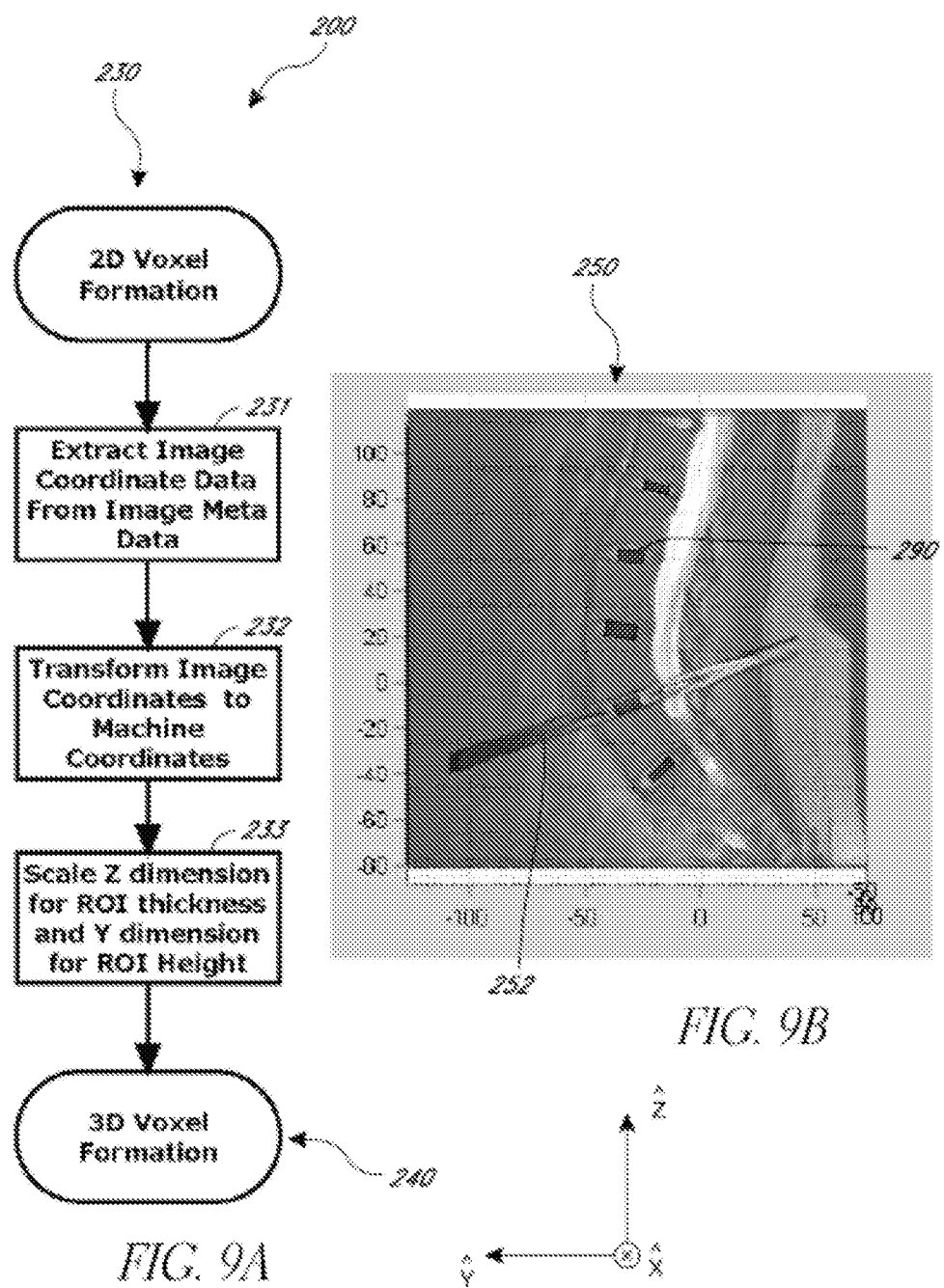
FIG. 9A is a flow diagram showing the 2D voxel formation portions of the flowchart of FIG. 5.
FIG. 9B is the mid-sagittal MRI image showing 2D voxel prescriptions within the respective discs of the 5 lumbar disc levels.

FIG. 9A reintroduces flow diagram 200 with respect to the 2D voxel formation phase 230, including more detailed blocks 231-233 in order to prepare for 3D voxel formation phase 240. An illustrative result of this phase is shown in FIG. 9B, which shows the mid-saggital 2D planar image 250 with the 2D voxel prescriptions 290 shown within the respective discs of the 5 lumbar disc levels. FIG. 9B also shows the 2D planar image 252 for the orthogonal transverse oblique axial plane for the L4-L5 disc in this example.

FIGS. 10A-B illustrate the result of this process as follows. FIG. 10A reintroduces for flow diagram 200 the flow for 3D voxel formation phase 240, including more detailed blocks thereof 241-246. An illustrative 3D voxel prescription result is shown for one disc of the spine in angular perspective view relative to two transverse mid-sagittal (e.g., yz plane) and mid-coronal (e.g., xz plane) 2D MRI images.

Additional details relating to various aspects of the process 200 described above are provided below. It is generally to be appreciated that the current systems and methods may be employed using a variety of different types of resources, including software programs, utilities, etc. According to certain detailed present embodiments, a software utility program "MATLAB" can be used. More specifically, the specific examples provided for detailed illustration in some embodiments have been put into actual use using the R2010b version of MATLAB along with the MATLAB Statistics and Image Processing toolboxes within that version.

At block 211, the process locates an MRI image, which can be a sagittal MRI image through the center of the ROI (e.g., having the largest ROI cross-sectional area). In some embodiments, the automated voxelation can use the same working set of MRI images used in manual voxel prescription process. Prior to image use, in some embodiments, the automated voxelation system and method can access the image files in each series and form a volume image structure for each consisting of a stack of image arrays.

In some embodiments, the method for collecting the sagittal, coronal, and axial or oblique axial image sets can be performed automatically or can be partially automatic. In some embodiments, a user can identify a mid-sagittal location for the mid-sagittal image (e.g., by selecting one of a series of low resolution images that corresponds to a sagittal center position), and the system can automatically compile a series of high resolution MRI images including a mid-sagittal MRI image at the location indicated by the user as well as other sagittal images taken at planes substantially parallel to, and space from, the mid-sagittal image. In some embodiments, some or all of the image processing phase 210 and ROI location and isolation phase 220 can be performed on a plurality of MRI images before a center slice is identified, so that a center MRI image can be identified by automatically comparing the sizes of the ROI in the plurality of MRI images. For example, the system can access a plurality of MRI images taken from substantially parallel planes that intersect the ROI, can calculate an area of the ROI in the plurality of MRI images, and can use the image with the largest ROI area as the center slice for voxel positioning. When multiple ROI (e.g., multiple intervertebral discs) are being analyzed, the system can calculate the ROI area for the multiple ROI in the plurality of MRI images and can select a center MRI image having the largest aggregate ROI area combined from the multiple ROI. This approach can be beneficial, for example, when identifying multiple voxels, e.g., for multivoxel MRS procedures with multiple ROI. In some embodiments, a center MRI image can be selected based on the largest ROI area for a single ROI, and in some cases, the system can allow for different MRI images to be selected as the center MRI image for different ROI. This approach can be beneficial, for example, for single voxel MRS procedures. The system can access multiple MRI images (e.g., taken from substantially parallel planes), and can test all or a subset of the images (e.g., the middle 7 images of an array of 13 image slices) to identify a center image. The system can start with an image at the middle of a series of images and can measure the ROI area for a number of images (e.g., 3 images) on either side of the middle image in the series of images.

In some embodiments, the selected center image can be an image other than the middle image of the series of MRI images, and the selected center image can, in some cases, correspond to a slice that is not through a center of the disc, or spine, or patient's body. A center image can be the middle image of a series of MRI image slices, and can, in some cases, pass through substantially the center of the ROI, the disc, the spine, and/or the patient's body. Many other variations are possible. In some embodiments, the system can identify the MRI images that have an ROI interest that meets a threshold amount, and can define the center MRI image to be the image at the middle of the series of images that meet the threshold FOI area amount. In some embodiments, the system can omit the identification of a center image. For example, the system can use some or all of the MRI images to generate a 3D model of the ROI without identifying a center image for the ROI. A voxel can be formed based on the 3D model of the ROI without identification of a center image for the ROI.

In some embodiment, the center image identification process can be repeated for the coronal series and axial or oblique axial series of MRI images in the coronal and axial or oblique axial planes. In some embodiments, the voxelation method 200 can use MRI images taken from only a single axis (e.g., the sagittal axis) for prescribing a voxel for the ROI. Thus, in some embodiments, the images of one or both of the other two axes (e.g., the coronal and/or the axial images) can be omitted. In some embodiments, the system can locate the ROI and/or positioned the voxel based on images from a single axis (e.g., sagittal) and the system can use one or more images from one or both of the other axes (e.g., coronal and/or axial) for displaying information to the user, such as for showing a 3D voxel in a 3D presentation between multiple images of different planes, as shown in FIG. 10B and discussed below.

In some embodiments, as part of the image processing 210, the system can convert the MRI image to a different format, such as from DICOM (Digital Imaging and Communications in Medicine) image data to MATLAB "gray" format with double precision intensity values in the range from 0 to 1. Portions of the MRI image can correspond to the ROI and surrounding area in a physical target object (e.g., a patient's spine). Although many embodiments disclosed herein are described in connection with MRI images, it will be understood that various types of electronic images can be used. An electronic image can be any electronic representation of an image, and may be related to MRI, CT, PET, X-ray, or other modality. The electronic image can include an image coordinate system and a plurality of pixels with unique respective image coordinates. Such electronic images may be considered "acquired" from a subject by virtue of the respective imaging modality that gathers information from the body which is then converted to the electronic image. An electronic image may comprise for example a single 2D planar image with x-y, x-z, or y-z coordinates, or a series of related 2D images in different planes that provide a coordinated "picture" of a region, such as may be combined in an array of images to provide a 3D image. Thus, throughout this disclosure, various types of electronic images can be used in place of the MRI images that are specifically discussed. The system can access metadata from the image files to support 3D interpretation of the image-coordinate data in 3D machine coordinates, also referred to as world coordinates for current purposes of this disclosure. For example, the system can form 4×4 homogeneous coordinate transformation matrices from the metadata to support image to machine coordinate transformation. Thus, images coordinate data corresponding to portions of the MRI image can be converted or transformed into world coordinates corresponding to portions of the target object. In some embodiments, the system can then organize all the above data into an AutoVox data structure that contains all the information to create a 3D volume display in machine (or world) coordinates. One example of a 3D volume display is shown in FIG. 10B, which is discussed below.

In order to analyze an MRI image, image processing can be performed to smooth the image, level the intensity variation from anterior to posterior, remove the bright spinal column and posterior fat signal, and finally emphasize the ROI (e.g., disc nucleus). The result of image processing 210 can be an image consisting almost exclusively of emphasized sub-images of multiple ROIs, as shown in FIG. 7B.

Various types of image smoothing can be used at block 212. For example, the system can perform 3D smoothing using the MATLAB function "smooth3" with a 3×3×3 cubic kernel. This 3D smoothing algorithm accesses the selected sagittal image and the sagittal images which bracket it in the image stack. This algorithm was found to provide notably better smoothing than a 2D algorithm with the 3D smoothing algorithm producing essentially no loss of edge acuity. Thus, in some embodiments an image smoothing operation 212 can modify the brightness of a pixel based on the brightness values of neighboring pixels, for example setting the pixel brightness to an average value, or a weighted average value, etc. In some embodiments, the neighboring pixels can be part of the same image (e.g., a 3×3 or 5×5 area around the pixel) and/or can be part of other images in the series of substantially parallel images (e.g., sagittal MRI images). For example, in the 3×3×3 kernel mentioned above, can use the adjacent image on both sides of the image containing the pixel being processed. The kernel can be referred to as cubic because the number of pixels that are used to modify the brightness of a pixel are equal (e.g., 3) in each direction (e.g., x, y, and z), even though the physical volume may not form a cube. For example, in the 3×3×3 cubic kernel example, the distance between adjacent MRI slices can be larger than the distance between pixels within the same image resulting in the cubic kernel coving a somewhat elongated rectilinear volume rather than a cube.

At block 213, top-hat filtering can be performed on the MRI image. The top-hat filtering can be configured to deemphasize (e.g., darken or remove) portions of the image that correspond to features other than the ROI while preserving the ROI portions of the image. In the example of intervertebral discs, the spinal column and posterior fat can form bright portions of the image (e.g., due to high water content), and the top-hat filtering operation can be configured to deemphasize these features while preserving the disc portions of the image. The system can perform, for example, morphological top-hat filtering on the image using vertical linear structuring element 50 pixels tall and 5 pixels wide. The structuring element can be effectively 50 running averages with 5 data points per average that is shifted across the image. The structuring element can be generally shaped like the shape of the structures to be deemphasized. As the structuring element is swept across the image, if the pixels covered by the structuring element satisfy a criteria (e.g., a threshold brightness level) then the pixels covered by the structuring element can be deemphasized (e.g., darkened or removed). In the illustrated example, the structuring element can be generally tall and thin (e.g., 50 pixels tall and 5 pixels wide) so that the structuring element can fit into the vertically oriented spinal column and fat portions of the image and not fit into the intervertebral disc portions of the image which are generally ellipsoidal in shape and relatively short and wide. Thus, the top-hat filtering can primarily target removing the bright water signal of the spinal canal and minimizing the signal from the posterior fat. The top-hat filtering can primarily deconstruct the bright water-rich image of the spinal canal in the MRI image to facilitate the algorithm that searches for the bright (e.g., water-rich) oval shape associated with the disc nucleus. It also can have the effect of leveling the intensity of the image. The top-hat filtering operation can basically remove (or darken) any parts of the image which it can encompass by the structuring element. Its dimensions are selected so it does not affect the ROI (e.g., disc nucleus) images.

In some embodiments, a first top-hat operation does not effectively remove the signal from the lower curved portion of the spinal canal, typically below L4L5. The system can then perform a second top-hat filtering operation with the structuring element as a line 50 pixels long and at a 45 degree slope to target the sloping lower portion of the spinal canal to target the lower curved portion of the spinal canal. Many variations are possible. Many different configurations of top-hat filtering operations can be performed depending on the shape and structure of the ROI and the surrounding area, and multiple top-hat filtering operations of various different numbers can be performed. In some embodiments, other forms of morphological image processing operations can be performed to either emphasize the ROI or to deemphasize the regions of the image not associated with the ROI.

At block 214, the system can perform order statistic filtering to further smooth and level the image while preserving edges. In some embodiments, two dimensional (2D) order statistic filtering can be used. The kernel, or domain, for the order statistic filtering can be a 5 by 5 pixel square, although other sizes can be used. The order statistic filtering can set the brightness of a pixel based on the brightness of neighboring pixels. In some embodiments the sixth order can be used, although other orders can be used. For example, in the sixth order embodiment, the filter operation can order the neighboring pixels and the analyzed area (e.g., 25 pixels in the 5×5 example) from darkest to brightest, and the filter operation can set the brightness value of the analyzed pixel to the sixth brightness value from the darkest. Thus, the order statistic filtering operation can generally darken the image except for pixels of the image that are generally surrounded by other bright pixels. The 5×5 kernel and sixth order parameters were optimized experimentally for some applications relating to intervertebral disc ROI, but many other configurations (e.g., of size, shape, and/or orders) can be used depending on the application. This operation can serve to remove small speckles and fill small holes while generally preserving edges of the ROI.

Many variations to the disclosed image processing 210 can be made. For example, in some embodiments, one or more of the operations discussed herein can be omitted or combined with other operations. For example, in some embodiments, the method can use only one of 3D image smoothing 212 and order statistic filtering 214 for removing noise, etc. and the other of 3D image smoothing 212 and order statistic filtering 214 can be omitted. Also, as discussed elsewhere herein, in some embodiments, the method can locate a center image 211 at a later stage of the method or the locating of a center image 211 can be omitted entirely. Also, additional image processing operations can be added in combination with or in place of the operations illustrated in the image processing phase 210 of FIG. 7A. For example, various other types of noise reduction filters can be applied. Also, a contrast enhancing filter can be applied to emphasize contrast in the image to facilitate identification of the edges of the ROI. In some embodiments, edge detection can be performed on the image to identify or emphasize the edges of the ROI. The methods and systems disclosed herein can perform one or more of the operations of the image processing phase alone or with various combinations of the other components of the method shown in FIG. 5 or described herein.

Having processed the image to emphasize the ROI (e.g, disc nuclei) while preserving their location, the system can next isolate and locate the ROI (e.g., disc nuclei) at phase 220. At block 221, default search areas 260 can be applied to the image. For example, in the illustrated embodiment, statistics on the location of each disc level in the image have been developed. For the default search areas 260 shown in FIG. 8B, a training set of ten MRI studies where digitized to locate disc center and disc tilt. The means of the disc centroid and disc tilt were used to define an ellipsoid search area for each level, such as shown at default ellipsoid search areas 260 in FIG. 8B. For each level, the search area ellipse 260 has a semi-major axis of 60 pixels and a semi-minor axis of 30 pixels and is centered on the mean location in image coordinates for a disc at that level, and the tilts for each level are 0°, 0°, −5°, −18°, and −30° for levels L1L2 to L5S1 respectively, although other configurations can also be used. This approach is justified as the lumbar image prescription protocol is very well standardized and followed in the studies acquired to date. In some embodiments, the system may use active shape modeling to locate ROIs or operator intervention to identify and/or confirm ROIs.

As would be apparent to one of ordinary skill based upon the disclosure immediately above, this present illustrated embodiment thus provides a template for refining statistical methods to determine actual disc locations based upon an atlas applied to the image developed from pre-existing knowledge of typical locations derived from prior acquisitions and segmentation defining the disc locations (which segmentation may even be done manually for purpose of creating the atlas). The template provides default regions in which the various disc levels in spines previously used to construct the template were known to be located, thus providing default regions applied to a given spine image so that processing algorithms may more effectively narrow a focused statistical search for the actual discs within that one new spine image. In some embodiments a single default search area 260 can be applied if a single ROI is to be identified, and in some embodiments, a plurality of default search areas 260 can be applied if multiple ROI to be identified.

After applying default ellipsoid search areas 260 to the image, such as at block 221 of Phase 220 of the voxel automation 200, the following can be performed. At block 222, for each or one or more of the elliptical search areas 260, all the pixels within the area which have a particular property (e.g., an intensity of at least 0.15) can be assigned to a pixel population corresponding to the ROI. The pixels can be identified by their spatial coordinates in the image (which correspond to world coordinates in the imaged object).

In some embodiments, the system can analyze the population of pixels 270 based on a reliability criteria. One criteria that may be applied, for example, is to require a certain threshold number, such as for example at least 300, of pixels in the pixel population (or grouped together) to qualify as a reliable estimate. In some embodiments, a tiered approach can be used depending on the number of pixels detects as part of the pixel population. In some embodiments, if there are between 150 and 299 pixels the pixel population may still be processed but considered, and flagged, as potentially unreliable; or, the pixel population may be kicked out of the automated system for manual prescription; or, further algorithms may be employed specifically tailored to overcome such circumstance. If there are fewer than 150 pixels, in some embodiments, the system can be set such that no attempt is made to locate the corresponding disc. Many variations and alternatives are possible. The comparison of the reliability criteria can reduce or avoid incorrectly keying on residual image artifacts as though they were a ROI. The aforementioned values have been empirically determined for a given population of examples, which is relatively small. Thus, values other than those specifically disclosed herein may be used in view of further data of clinically relevant numbers representative of a given target population distribution. Also, values other than those specifically disclosed herein may be used for other specific applications other than that described herein (e.g., voxelation in regions of the body other than intervertebral discs).

In this regard, it is to be appreciated that the default and estimated aspects of these detailed embodiments applied may be influenced by certain subject-dependent variables, such as height, weight, BMI, gender, age, race or ethnicity. The present disclosure contemplates that aspects of the present embodiments may take such variability into account, such as for example generating default ellipsoid search areas 260 from spine MRIs from target numbers of samples on such uniquely identifiable sub-population bases (e.g., based on age, gender, race, height, weight, or BMI).

FIG. 8B shows a bright spot 272 that appears structurally to be near but clearly outside of the L3-L4 disc nucleus, but is still nonetheless captured within that respectively assigned default ellipsoid search area 260. The bright spot 272 is separated from the more heavily populated pixilated region that does appear to be the respective disc nucleus. Such non-target tissue region artifact 272 may result in statistics used in further processing to capture signal intensity from such peripheral structures outside of the target disc nucleus, and thus potentially compromise the statistics used to estimate the disc nucleus. In fact, one possible result for this example is shown in FIG. 8C at the estimated ellipsoid shape 285 for that same L3-L4 disc. Relative to the other estimated disc nucleus ROI ellipsoids 280, the estimated shape 285 is slightly off-angle and extended partially in the direction of the artifact signal 272, and appears to potentially capture some inferior vertebral body structure.

Accordingly, some embodiments of this disclosure contemplate use of further algorithms and methods to distinguish possible sources for such potential artifact, such as by statistical methods to exclude artifacts in one step from being used in calculations in the next step (e.g., confidence interval calculations, basing on separation between strongest contiguous signal region, location relative to the default ROI, combinations thereof, etc.). In some embodiments artifacts can be excluded by review of the quality of the results 285 shown in FIG. 8C relative to signal intensity, contrast, or image homogeneity captured within the drawn shape. The results can be modified to correct or allow for circular correction algorithms back to prior operations (but performed differently based on data obtained from subsequent operation(s)). In the example of FIG. 8C, a neighboring function can be performed that identifies that the identified population of pixels includes a neighboring group of pixels near the main group of pixels, and the neighboring function can cause the neighboring group of pixels to be excluded from analysis of the population of pixels. The neighboring function can identify neighboring groups of pixels that do not contact and are separated from the main group of pixels. In some embodiments, the neighboring function can be configured to identify a neighboring group of pixels that do contact the main group of pixels by recognizing that the neighboring group of pixels do not conform to an expected shape of the ROI, for example, if the bright spot 272 of FIG. 8B were connected to the bright ellipsoid disc shape as an arm or extension that does not fit with the ellipsoid shape.

In some embodiments, further manual opportunities may be provided for assistance. For example, the image 250 shown as modified in FIG. 8B may be presented to a user to allow for regions to be manually captured (e.g. mouse drag) for exclusion or inclusion. Manual indications of areas of exclusion or inclusion may be done as a matter of course or may be done only when a particular interim result is "flagged" as potentially erroneous and thus appropriate for manual intervention. Thus, in some embodiments, review of the process and/or results can be performed in order to optimize results or to correct or remove sources of error.

At block 224, the system can calculate a two dimensional model from the shape of the population of pixels. In the embodiment illustrated in FIG. 8C, for the cluster of pixel locations identified in each level search area, an expectation maximization algorithm for decomposing Gaussian mixtures (EM_GM algorithm) can be applied at block 223. The EM_GM algorithm can provide parameters (e.g., means and covariance matrix) of a two dimensional Gaussian distribution representing the spatial distribution of the pixels in the cluster. A cross section or footprint of the 2D Gaussian distribution can have a generally ellipsoidal shape. With appropriate scaling, experimental observation indicates that the EM_GM algorithm appears to form a very good approximation to the generally ellipsoidal shape of the disc nucleus, although other methods can be used to form a 2D shape or model based on the population of pixels. In the illustrated embodiment, examining the eigenvectors of the covariance matrix can be used to yield the orientation (tilt) of the disc, which initial experimental observation has also suggested results in very good accuracy. An experimentally determined scale factor of 2.5 can be applied to the standard deviations from the covariance matrix to use as the semi-major and semi-minor axes of the disc ellipse estimate. Various other shape approximation operations can be used to estimate the shape of the ROI based on the population of pixels identified at block 222. For example, active shape modeling, statistical shape modeling, or various other techniques such as those generally referred to as blob detection can be used to estimate the shape of the ROI.

Many variations to the disclosed ROI location and isolation process 220 can be made. For example, in some embodiments, one or more of the operations discussed herein can be omitted or combined with other operations. For example, in some embodiments, the image processing can emphasize the ROI so that the process can locate the populations of pixels without using the applying the default search areas at block 221. In some embodiments, a default area (e.g., formed by atlas-based segmentation and/or historical date of common ROI locations) can be used after ROI detection or after voxel formation as a check. For example, if the location of an identified ROI, or prescribed voxel, does not fit into or correspond with the default area, the identified ROI, or prescribed voxel, can be flagged as potential unreliable, disregarded, presented to the user for review, recalculated, and/or adjusted. Also, operations can be added in combination with, or in place of, the operations illustrated in the method shown in FIG. 8A. For example, as mentioned above, various types of blob detection techniques can be used to identify the shape of a ROI.

Also, in some embodiments, the method can use user input along with automated procedures to identify the ROI. For example, the user can be permitted to identify a location (e.g., by clicking on the image) that is inside of a ROI (a single location for a single ROI or multiple locations for multiple ROI) to provide guidance in locating the ROI. For example, the process can search within an area centered on the location identified by the user to search for the ROI boundaries. For example, the process can use an edge detection operation to identify edges of the ROI around the location identified by the user. The program can also use the image brightness of the location clicked by the user in determining what brightness threshold to apply for identifying other pixels associated with the ROI. The contrast ratio between ROI and non-ROI portions of the image can vary significantly between patients, but if the user specifies a location that is known to be part of the ROI, the brightness of that portion of the image can be used to set the brightness threshold used to identify other portions of the same ROI or of other ROI. In some embodiments, the program can allow the user to identify (e.g., click) points outside the ROI, such as along one or both of the end plates that surround the intervertebral disc, and the program can use those points to guide the locating of the end plates or of the ROI (e.g., disc between the end plates). The program can select the voxel size and/or orientation based at least in part on the clicked end plate points, e.g., by fitting a linear line or curve between the clicked end plate points and placing the voxel between the lines associated with the end plates. The end plate clicks can be used to define a search area for locating the ROI as well.

The methods and systems disclosed herein can perform one or more of the operations of the ROI location and isolation phase 220 alone or with various combinations of the other components of the method shown in FIG. 5 or described herein.

Given the above ROI (disc nucleus) characteristic data provided per the operations above, it becomes possible to automatically form two dimensional (2D) shapes or voxels, at phase 230. At block 231, image coordinate data can be extracted, and at block 232, the image coordinates can be converted to world coordinates using a transformation matrix. The system can, for example, apply an experimentally determined scale factor (e.g., of 2.9 times the image to world scale factor (e.g., 0.39 from the DICOM metadata)) to the semi-minor axis to determine the voxel thickness in the z-axis (axial axis), and to the semi-minor axis to determine the voxel dimensions in the machine y-axis (coronal axis), as shown in block 233. In some embodiments, the 2D shape can be a rectilinear shape such as a rectangle, although many other 2D shapes can be used. Many variations are possible. Various components of the 2D voxel formation phase 230 can be combined or omitted. For example, in some embodiments, the 2D shape can be defined in image coordinates and then the coordinates of the 2D image can be transformed to machine (or world) coordinates, or the transformation to world coordinates can be omitted from the 2D voxel formation phase 230, for example by transforming image coordinates to world coordinates after the 3D voxel is formulated. The methods and systems disclosed herein can perform one or more of the operations of the 2D voxel formation phase 230 alone or with various combinations of the other components of the method shown in FIG. 5 or described herein.

3D Voxel Formation of phase 240 can include determining voxel width across the coronal plane or x-axis (sagittal axis), which can include the following. The system can locate a sagittal slice adjacent to the previous processed sagittal image slice at block 214, and can repeat image processing 242, ROI location and isolation 243, and 2D voxel formation 244 for the sagittal slice adjacent to the previously processed sagittal image. The system can compare the newly calculated 2D voxel to the 2D voxel from the previously processed sagittal slice to determine if the previously established 2D voxel dimensions fit within the current 2D voxel of the current sagittal slide being analyzed. The system can modify (e.g., decrease) the 2D voxel dimensions if required to fit the current 2D voxel. This process can be repeated for each sagittal slice being considered (e.g., until all sagittal slices that encompass the ROI have been analyzed). A three dimensional (3D) volume or voxel can be formed using the final 2D voxel dimensions as a cross sectional shape for the 3D voxel projected across the width of the analyzed sagittal slices to form a rectilinear volume. Although many embodiments are described herein as using a series of MRI images corresponding to sagittal slices, coronal, axial, or oblique axial MRI images can also be used.

In some embodiments, the volume of the 3D voxel can be increased or maximized while also being contained within the ROI. For example, for a voxel with a rectilinear volume shape and a ROI having a generally ellipsoidal shape (e.g., an intervertebral disc), various 3D voxel shapes and sizes can be used having various different dimensions (e.g., a voxel having a smaller height may have a larger length and/or width while remaining contained in the ROI than a voxel having a larger height, which can have a smaller length and/or width in order to fit into the ROI). The system can select a 3D voxel having a maximized or increased volume. In some embodiments, one or more of the MRI images may not contribute to the formation of the voxel, for example, if inclusion of an MRI image near the end of the ROI would require that the height of the voxel be reduced to a degree that would lower the total volume of the voxel, the MRI image near the end of the ROI can be disregarded for the forming of the voxel. In some embodiments, the volume can be maximized by defining a voxel for multiple combinations of MRI images and the voxel with the largest volume can be selected. For example, for an array of MRI images having 13 slices, voxels can be defined using 13 slices, 12 slices, 11 slices, 10 slices, etc. The volumes for the voxels can be calculated and compared and the voxel having the largest volume can be selected (e.g., a voxel using 9 MRI images and omitting the 2 end slices from each side). In some embodiments, the voxel can be formed to provide an increased or maximized dimension (e.g., height, width, or length) of the voxel.

In some embodiments, the process can define the voxel contained within an inward offset from the boundaries of the ROI. For example, the offset can provide a buffer that can prevent the voxel from covering non-ROI tissue in the event of minor inaccuracies in voxelation and/or minor patient movement during a procedure. In some cases, if the voxel were defined to reach to the edge (or very close to the edge) of the ROI, patent movement during the examination or minor inaccuracies in voxelation can cause the voxel to cover a portion of non-ROI tissue during a procedure, which can reduce the quality of the procedure as discussed above. The offset can be applied at various stages of the process. For example, in some embodiments, the final voxel can be reduced in size after voxelation. The population of pixels can be reduced in size after being populated, for example, by removing a layer of pixels (e.g., 1, 2, 5, 10 pixels, etc.) at the edge of the population of pixels. The size of the shape that approximates the population of pixels can be reduced in size, or the 2D voxel shapes can be reduced in size before they are used to form the 3D voxel. The process can be configured to increase or maximize the area of the voxel (similar to the description above) while containing the voxel within the inward offset boundary of the ROI.

In some embodiments, multiple voxels can be formed for a single ROI. For example, a plurality of rectilinear voxels can be positioned inside of an ellipsoidal shape to increase the amount of the ellipsoidal shape that is included for a procedure. The plurality of voxels can have different shapes and/or sizes. For example, a relatively large voxel can be positioned at a central region of the ROI and one or more smaller voxels can be positioned around the larger voxel in the ROI. In some embodiments, the plurality of voxels can have the same size. For example, a standard voxel size and shape (e.g., cube or square) can be used and the process can be configured to fit the standard voxels into the shape of the ROI.

Many other variations are possible. For example, in some embodiments, the y-axis (coronal axis) value can be set equal to the x-axis (sagittal axis) value, thereby simplifying the voxel formation. In some embodiments, instead of modifying the 2D shape as needed at each sagittal layer, the system can form the 2D shapes for each sagittal layer independent of the other layers, and the system can then define the cross sectional shape of the 3D voxel to be the area shared by all the 2D shapes when the 2D shapes are overlay on each other. In some embodiments, the 3D voxel can be a non-rectilinear volume shape. For example, the 3D voxel can be formed by connecting the multiple 2D shapes (e.g., by interpolating) to form a 3D voxel, which can have an irregular shape not defined by an equation or mathematical shape. In some embodiments, the system can skip the 2D voxel formulation phase 230. For example, the system can calculate a 3D model for the ROI based on the populations of pixels that are identified in the series of parallel sagittal slices. A 3D voxel can then be selected that fits into the 3D model. For example, a 3D voxel can be selected that provides an increased or substantially maximized volume for the given 3D model.

At block 245, the 3D voxel can be displayed, for example, so that a user can inspect the 3D voxel. As shown in FIG. 10B, the 3D voxel can be displayed relative to a mid-sagittal MRI image, a mid-coronal MRI image, and/or an axial (or oblique axial) MRI image (not shown in FIG. 10B), so that the 3D voxel can be compared to the ROI displayed on the MRI images. In some embodiments, the system can allow the user to manipulate the view of the 3D voxel for inspection at various angles. In some embodiments, the system can allow the user to manually adjust the size or shape of the 3D voxel. In some embodiments, block 245 can be omitted. In some embodiments, block 245 can be performed only if one or more of the prior operations caused the procedure to be flagged as being potentially unreliable.

At block 246, the system can display the voxel dimensions, coordinates, and/or angles for the user. In some embodiments, the voxel dimensions, coordinates, angles, and/or other voxel data can be transferred to an MRS system so that the 3D voxel can be used as a scan area during a MRS exam, as described above. The system can provide the 3D voxel information to the MRS system in machine (or world) coordinates. The conversion from image coordinates to world coordinates can be performed at various stages of the process 200. For example, in some embodiments, the system can convert image coordinates for the pixels in the population of pixels to world coordinates, and the formation of the 2D model, 2D voxel, 3D model, and/or 3D voxel can be done in world coordinates. In some embodiments, the system can use image coordinates for formation of the 2D model, 2D voxel, 3D model, and/or 3D voxel, and the final data transferred to the MRS system can be converted to world coordinates. It will be understood that the conversion from image coordinates to world coordinates can be performed at other stages of the process 200 than those specifically identified.

The methods and systems disclosed herein can perform one or more of the operations of the 3D voxel formation phase 240 alone or with various combinations of the other components of the method shown in FIG. 5 or described herein. Various components of the illustrated 3D voxel formation phase 240 can be combined, omitted, or supplemented with additional components.

In some embodiments, the program can use images of different modes to improve the accuracy of the voxelation process or to check the accuracy. Different modes of MRI images can be, for example, MRI images made using a T1 process (first mode) and MRI images made using a T2 process (second mode). The images can be made of the same tissue to allow for comparison between the images of the different modes. The voxelation process can be performed on the images of different modes, and the resulting voxel results can be compared. Because images of different modes can have differences such as different contrast ratios applied to different tissues, the resulting voxels can be different for each mode of imaging. The voxels produced using the different modes of images can be combined (e.g., averaged) to form a final voxel to be used in the MRS exam. Thus, if one mode of images does not sufficiently represent one aspect of the tissue being imaged, one or more of the other modes of images can better represent that aspect of the tissue and improve the accuracy of the final voxel. The voxels produced by the different modes of images can also be compared, and if the differences between the voxels is above a threshold level, the voxelation process can be flagged as potentially unreliable, can be restarted, can be aborted, or can be supplemented with additional operations designed to minimize errors. In some embodiments, the information derived from the images of different modes can be compared or combined before voxel formation, for example after defining populations of pixels for the multiple images of different modes, the defined pixel populations can be combined (e.g., averaged) or compared to confirm accuracy.

One further embodiment uses two different images of the same area of tissue via two different imaging modalities, and performs an image fusion operation between them. In one embodiment, the fusion operation includes a "differencing" between the images to produce a third "differencing" image. In another embodiment, the fusion operation comprises performing a blending or merging between the images (e.g. alpha blend, for example). Such image fusion, according to these or other illustrative examples, is applied in certain embodiments for emphasizing contrast at certain particular tissue structures, or interfaces between adjacent amorphous tissue structures—such as that vary in different chemicals that are respectively emphasized by each different modality. One particular embodiment differences T1 and T2-weighted images, whereas another applies the fusion (e.g. differencing or blending) to emphasize contrast at the borders, e.g. bony boundaries, of musculoskeletal joints (e.g. adjacent vertebral bodies bordering intervertebral discs), whereas another applies this T1 and T2-weighted image fusion to musculoskeletal joints, such as spinal joints. According to these various embodiments, the results of the fusion themselves may provide various different benefits, either in their own right for diagnostic image analysis, or for further downstream operations (such as for example consistent with other embodiments disclosed herein, e.g. for use in generating voxel prescription, generating related structural measurements, directing certain further operations, or otherwise regarding segmented target regions of interest, or other purposes and combination uses).

Figure 11A:
FIG. 11A shows a T1-weighted image from a commercially available 3T MRI scanner of a lumbar spine segment in a volunteer human subject.
Figure 11B:
FIG. 11B shows a T2-weighted image from the same scanner of the same lumbar spine segment in same subject, and acquired during a different pulse sequence acquisition segment of the same scanning session, as the T1-weighted image shown in FIG. 11A.
Figure 11C:
FIG. 11C shows a T1-T2 differencing image derived from the T1 and T2-weighted images of FIGS. 11A-B, respectively.

FIGS. 11A-C illustrate one more detailed example applying this fusion approach described immediately above for emphasizing image contrast along pixel populations corresponding with vertebral body end-plate borders above and below intervertebral discs of spinal joints (in this case lumbar), and also elsewhere at other borders around such disc and vertebral body structures, as follows.

FIG. 11A shows a T1-weighted image of a lumbar region of a volunteer human test subject, taken via a commercial 3T MRI scanner. FIG. 11B shows a T2-weighted image of the same lumbar region of the same subject, taken during the same imaging session on same scanner. FIG. 11C shows the T1-T2 differencing result, again of the same lumbar region. As is clearly demonstrated in comparing these results, the differencing result of FIG. 11C provides more significant contrast at the end-plate borders above and below each disc than is provided by either the T1 or T2-weighted images independently shown in FIGS. 11A-B, respectively.

This T1-T2 differencing shown in FIG. 11C was derived by processing the T1 and T2-weighted images of FIGS. 11A-B as follows. Differencing is a built-in capability on most scanner or image viewer systems, either for post-processing after a study or such that a technician operator may readily do so at the time of an exam, e.g. to check for patient motion (which may be a valuable utility to determine if a rescan may be required or a good idea—clearly best determined if possible while the patient is still in the imaging modality). Commercially available software packages and related tools, such as for example "MATLAB" (Version 7.14 with Imaging Processing Toolbox Version 8.0), a commercially available programming language and environment from MathWorks, Inc., provides the capability to directly perform image processing operations, including fusion as described above. For example, the difference image of FIG. 11C was generated by the MATLAB code segment:

```
T1T2Diff = imfuse(T1s6, -T2s6, 'diff');
imshow(T1T2Diff, [ ]).
``` where T1s6 and T2s6 are MATLAB intensity image matrices as formed directly from the corresponding DICOM files by the MATLAB function "dicomread"

Figure 11D:
FIG. 11D shows a T1-T2 "blended" or "merged" image derived from the T1 and T2-weighted images of FIGS. 11A-B.

FIG. 11D shows the result according to another illustrated embodiment, wherein the same T1 and T2-weighted images are "blended" or "merged"—in this particular example according to an "alpha-blend" approach. This blended image is formed in a manner similar to deriving the differenced image, as by the same MATLAB program but invoking instead the following code segment:

```
T1T2Blend = imfuse (-T1s6, -T2s6, 'blend');
imshow(T1T2Blend, [ ]).
```

Figure 11E:
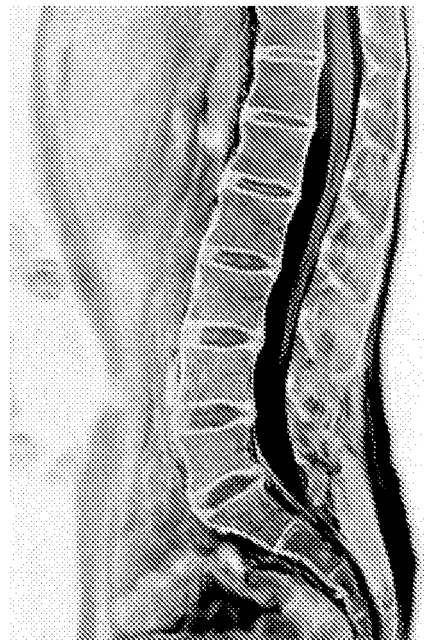
FIG. 11E shows the T1-T2 differencing image of 11C at a first contrast setting.
Figure 11F:
FIG. 11F shows the T1-T2 differencing image of 11C at a second contrast setting that is different than the first contrast setting of the embodiment shown in FIG. 11E.

It is also noted that the illustrated embodiments shown in FIGS. 11C and 11D are "negative" images of the processed combined image approaches, as in the target contrast area of the end-plate borders were observed to be particularly emphasized in that negative mode. The reference T1 and T2-weighted images shown in FIGS. 11A-B are shown with contrast and brightness settings (range and center) as would typically be viewed. However, contrast can be varied to also vary the results. For example, FIGS. 11E and 11F show the same differencing result at lower and higher relative contrast settings—with varied emphasis at the end-plate borders (which may impact how subsequent functions operate to segment the disc, or conversely vertebral bodies, between adjacent end-plates). Note also that the contrast is also clearly emphasized not just at the end-plate borders, but also along the lateral anterior and posterior walls of the spinal column, both along the vertebral bodies and disc regions (in particular via bright white in FIG. 11F). This results in nearly completely defining the enclosed circumferential borders surrounding these respective tissue structures of the spinal linkage system (e.g. serial vertebral bodies and discs), and are well permissive for success in further refinement operations such as edge detection and/or modeling for use in other applied purposes (e.g. dimensional or volumetric measurements, voxel prescription, or other further aspects of this disclosure). The processed images are on same slice from a multi-slice acquisition (in the particular case, slice 6).

In performing these imaging combining approaches, such as for example differencing and/or to show evidence of motion between images taken at two different time points, the field of views may be the same, or the two acquisitions may be performed with different resolutions. For illustration, a T2-weighted image may be a 320×320 image while the T1 maybe a 384×384 image for example. In this situation, they could be resampled to equalize them and then difference or otherwise combination-process them. An acquisition protocol may also specify that the different images be collected under the same prescription to facilitate differencing or other combination processing.

The differencing vs. blended approaches illustrated in these examples may vary or be roughly equivalent in terms of respective benefits for a specific implementation. In this particular case, while roughly equivalent, the blended approach may be slightly superior for endplate emphasis. Certain other aspects may impact results, such as for example "leveling," which generally refers to compensating for the brightness variation that varies with signal strength as a function distance from the receive coil. On FIG. 11A, for example, the fat is much brighter posterior than anterior but not with such apparent difference on the T2 of FIG. 11B—a difference which could potentially impact preferred images in a given case, such as one fusion approach vs. another.

An additional step in such image combining processing may also include a registration operation, to ensure exact overlay anatomically between the images (as they are taken at different times in the sequencing, and patient motion may intervene). Commercial tools are available for such registering between two separate images, such as for example the MATLAB (referenced above) Image Processing Toolbox function: "imregister". Registering may also be done for example by use of commercially available software packages or utilities, such as for example the same MATLAB package referenced above for other operations, but for example using a code segment such as the following:

```
[optimizer, metric] = imregconfig('multimodal')
T1Reg= imregister((T1s6, T2s6, 'rigid', optimizer, metric);.
```

This transforms the first image, T1s6 to be in alignment with the second, T2s6 and returns the transformed (registered) image as T1Reg. The first line defines a set of parameters to the registration algorithm appropriate for registering images of different modalities, in particular, having different brightness ranges.

In this particular example of FIGS. 11A-F, registering the separate T1 and T2-weighted images was tried—although no need was apparent as they are in essentially perfect registration in their original forms.

It is to be appreciated that these embodiments illustrated above by reference to FIGS. 11A-F are shown and described in context of an MR scanner operation, and in particular context of T1 and T2-weighted images. However, the broad aspects contemplated may also be achieved by further embodiments involving different pulse sequence acquisition approaches (E.g. T1rho or T2*), a combination of more than 2 different images, or images taken on different imaging modalities than these specific examples.

Figure 12:
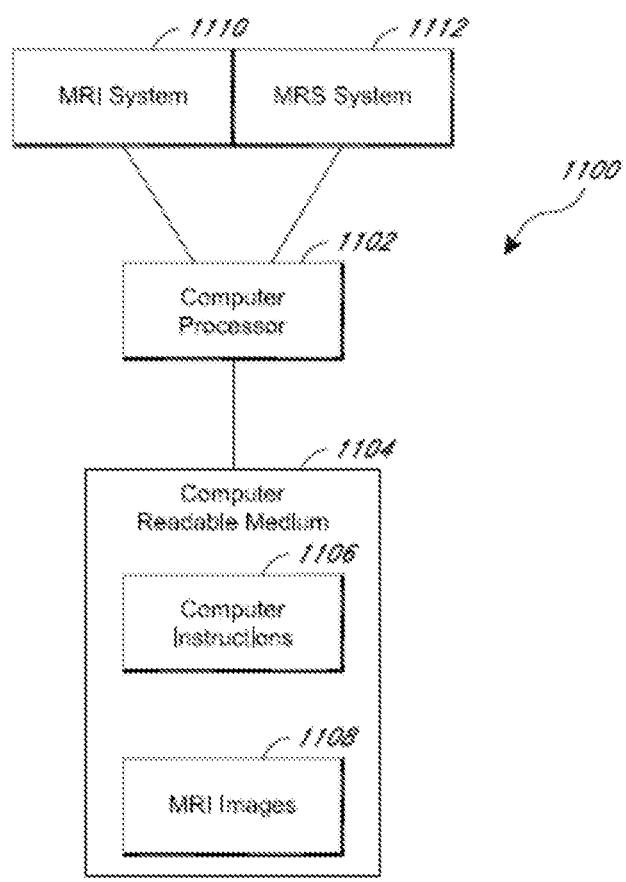
FIG. 12 shows an example embodiment of a system for performing voxelation or for otherwise analyzing a ROI in one or more MRI images.

FIG. 12 schematically illustrates an example embodiment of a system 1100 that can be configured to perform the process 200, or some portion thereof, or some variation thereof. The system 1100 can include a computer processor 1102 and computer readable medium 1104. The processor 1102 can be a general purpose processor or a special purpose processor, and the computer readable medium 1104 can be, for example, a tangle, non-transitory computer readable medium such as a hard disk, a non-volatile memory module, a volatile memory module, an optical disc, etc. The computer readable medium 1104 can include computer instructions 1106 (e.g., a software program) which can be configured to cause the system 1100 to perform the method 200, or some portion thereof, or some variation thereof, as disclosed herein. In some embodiments, different code modules can be stored on separate computer storage devices or media, and can be executed by different processors or machines. In some embodiments, the computer readable medium can include one or more MRI images 1108 to be used for voxelation or for otherwise analyzing a ROI represented in the MRI images.

In some embodiments, the system can include an MRI system 1110, which can be used to acquire the MRI images 1108. The system 1112 can also include an MRS system configured to perform an MRS exam, which can use a voxel provided by the system 1100 as a scan area. In some embodiments, the MRI system 1110 and the MRS system 1112 can be integrated into a single system configured to generate MRI images and to perform MRS examinations. In some embodiments, the MRI system 1110 and/or the MRS system 1112 can be omitted, and the system 1100 can perform voxelation without being connected to the MRI system 1110 or the MRS system 1112. The components of the system 1100 can be in communication with each other and can be located in close proximity to each other. For example, the entire system 1100 can be integrated into a single device (e.g., with a computer system integrated into a joint MRI/MRS system). The components of the system 1100 can be located in a single room or within the same building (e.g., a hospital). In some embodiments, some components of the system 1100 can be located remotely from other components. For example, the MRI system 1110 and/or the MRS system 1112 can be located remotely from the processor 1102 and computer memory 1104, and a communication connection can be established using the internet or a network. In some embodiments, the prescription of one or more voxels, or other analysis of the ROI, can be performed by a different system or by a different party than the system or party that acquires the images 1108 and/or performs the MRS exam. In some embodiments, the prescription of one or more voxels, or other analysis of the ROI, can be performed at a later time and/or at a different place than the acquisition of the images 1108 and/or than the MRS exam.

In some embodiments, the MRI images can be acquired (e.g., by MRI system 1110) using a first acquisition mode (e.g., T2 MRI imaging) and an MRS procedure (e.g., performed by MRS system 1112) can be performed using a second acquisition mode (e.g., T1 rho MRI imaging). Thus, in some embodiments, the ROI locating and voxelation can be performed based on data obtained from the first acquisition mode (e.g., T2) and the voxel can be used for a procedure or exam that uses the second acquisition mode (e.g., T1 rho).

In some embodiments, information provided by the ROI locating or voxelation process can be used for treatment of a patient. For example, a voxel can identify a target area in the patient's body for treatment such as radiation therapy, high-intensity focused ultrasound therapy, or various other procedures.

Although various embodiments are described herein in connection with nuclear magnetic resonance (MR) processes such as MRI and MRS, other imaging and analysis processes can be used. For example, a CT system, an X-ray system, a PET imaging system, or other imaging systems can be used for identifying or analyzing the ROI. Thus, although many embodiments discuss the use of MRI images, it will be understood that CT images, PET images, X-ray images, or images of a different modality can be used in combination with or instead of the MRI images discussed herein. Also, although some embodiments discuss the use of the voxel or ROI information in connection with an MRS exam procedure, it will be understood that CT, PET, X-ray, and other procedures can be performed based on the voxel or ROI information.

Figure 13:
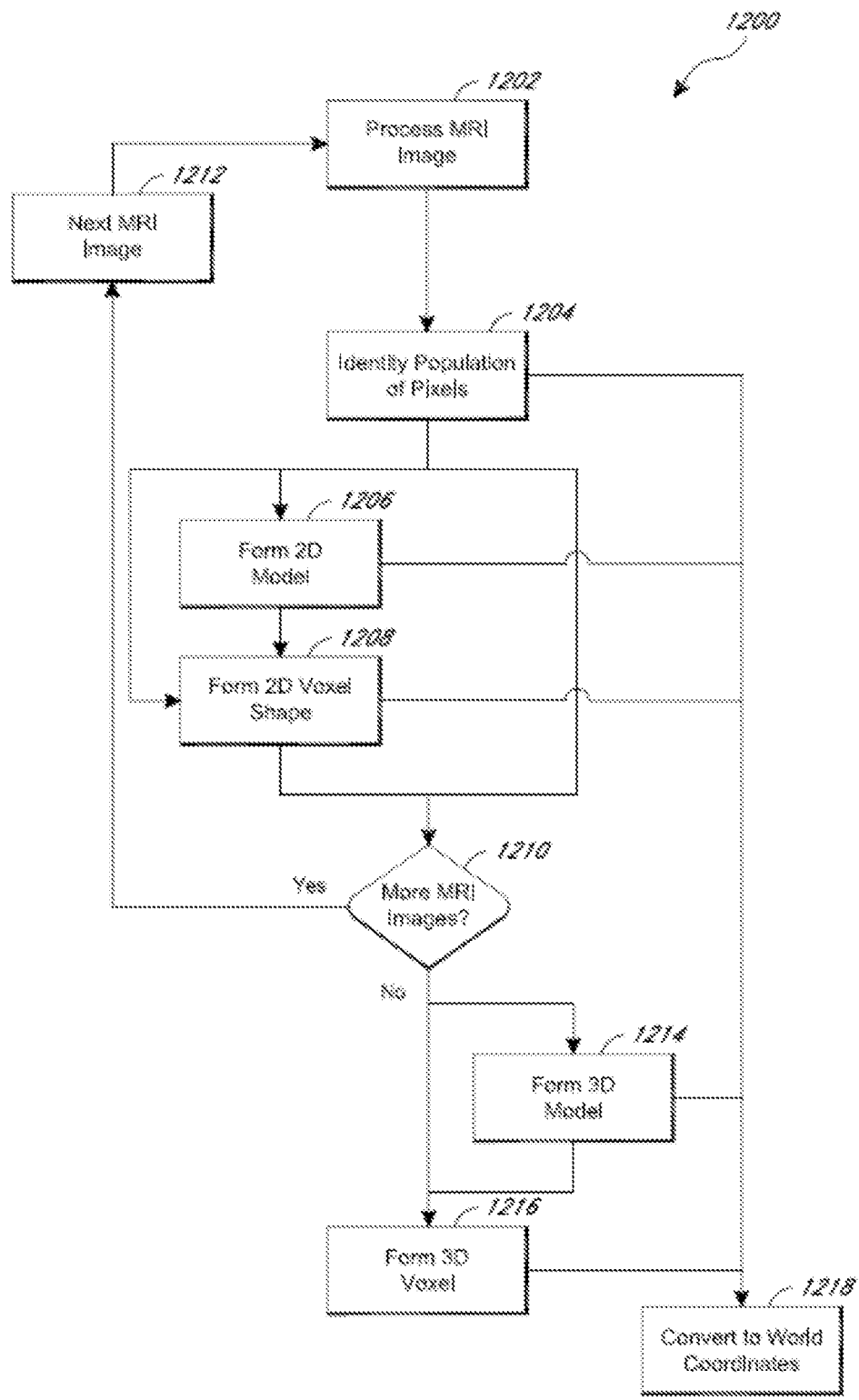
FIG. 13 is a flow chart illustrating example embodiments of methods for obtaining information relating to a ROI in one or more MRI images.

FIG. 13 is a flow diagram showing various example methods. In some embodiments, a method can start at block 1202 by processing an MRI image as described herein, and at block 1204, the system can identify a population of pixels relating to the ROI in the MRI image. The process can proceed to block 1206 where the system can form a 2D model of the ROI shown in the MRI image using the population of pixels. The 2D model can be used to form a 2D voxel shape at block 1208. In some embodiments, the system can form a 2D voxel shape directly from the population of pixels, without forming a 2D model of the ROI (as shown by the arrow between blocks 1204 and 1208). The process can proceed to block 1210 after forming a 2D model or a 2D voxel shape, or the process can proceed to block 1210 after identifying a population of pixels for the MRI image (e.g., without forming a 2D model or voxel shape). At block 1210, if additional MRI images are to be analyzed, the process can move to block 1212 to access the next MRI image, and then proceed back to block 1202 to repeat. If no additional MRI images are to be analyzed, the process can proceed to block 1214 to form a 3D model of the ROI (e.g., using data from the populations of pixels from the MRI images or by calculating a composite of the 2D models made at block 1206 for the MRI images). The process can advance to block 1216 and use the 3D model to form a 3D voxel that fits into the 3D model of the ROI. The process can also advance from block 1210 to block 1216 to create a 3D voxel without a 3D model. For example, the process can form a 3D voxel by expanding one of the 2D voxel shapes (formed at block 1208) across the width of the MRI image slices, and the process can adjust the shape of the 2D voxel shape as needed to remain inside the ROI for each MRI image slice, as described above.

The lines leading from blocks 1204, 1206, 1208, 1214, and 1216 to the block 1218 illustrate that at various stages of the process, data can be converted from image coordinates to world coordinates (e.g., for use in an MRS exam or for locating a ROI). For example, in some embodiments, the image coordinates corresponding to the population of pixels can be converted to world coordinates that represent the location of a ROI. Thus, in some embodiments, the method can be performed for a single image and can proceed from block 1202, to 1204, and then to 1218. In some embodiments, one or more 2D models (for a single MRI image or multiple MRI images), or a 3D model can be converted to world coordinates for identifying the location, size, and/or orientation of the ROI. Thus, in some embodiments, the method does not create a voxel to define a scan area for an MRS exam, and the process can merely provide information about the ROI (e.g., size, location, orientation) to a user or to a system. In some embodiments, the world coordinates can be used for an MRS exam or other procedure or can be reported to a user or system for additional analysis. In some embodiments, the world coordinates can be used for additional portions of the processes disclosed in FIG. 12. For example, a 3D model formed at block 1214 can be converted to world coordinates at block 1218 and the world coordinates can be used to form a 3D voxel at block 1216. Also, the 2D voxel shapes formed at block 1208 can be converted to world coordinates and the world coordinates can then be used for forming the 3D voxel at block 1216. Many other variations are possible. Alternative flow paths through the flow cart of FIG. 13 are possible other than those specifically discussed, and are contemplated as part of this disclosure. The methods illustrated by FIG. 13 can be implemented by a system such as system 1100 of FIG. 12.

The following United States patent application Publications are herein incorporated in their entirety by reference thereto: US 2005/0240104, US 2010/0086185, US 2010/0268225.

The following additional references are also herein incorporated in its entirety by reference thereto:

Peng Z, "Automated Vertebra Detection and Segmentation from the Whole Spine MR Images," Proceedings of the 2005 IEEE Engineering in Medicine and Biology 27$^{th}$ Annual Conference, Shanghai, China, Sep. 1-4, 2005.

Wu M et al., "Quantitative comparison of AIR, SPM, and the fully deformable model for atlas-based segmentation of functional and structural MR images." *Hum Brain Mapp.* 2006 September; 27(9):747-54.

Liu J et al., "Rigid model-based 3D segmentation of the bones of joints in MR and CT images for motion analysis." *Med Phys.* 2008 August; 35(8):3637-49.

Liu J et al., "Oriented active shape models." *IEEE Trans Med Imaging.* 2009 April; 28(4):571-84.

Chevrefils C et al., "Texture analysis for automatic segmentation of intervertebral disks of scoliotic spines from MR images." *IEEE Trans Inf Technol Biomed.* 2009 July; 13(4): 608-20.

Huang S H et al., "Learning-based vertebra detection and iterative normalized-cut segmentation for spinal MRI." *IEEE Trans Med Imaging,* 2009 October; 28(10):1595-605.

Michopoulou S K et al., "Atlas-based segmentation of degenerated lumbar intervertebral discs from MR images of the spine." *IEEE Trans Biomed Eng,* 2009 September; 56(9): 2225-31.

Kadoury S et al., "Personalized X-ray 3-D reconstruction of the scoliotic spine from hybrid statistical and image-based models." *IEEE Trans Med Imaging.* 2009 September; 28(9): 1422-35.

Koh J et al., "Automatic segmentation of the spinal cord and the dural sac in lumbar MR images using gradient vector flow field." *Conf Proc IEEE Eng Med Biol Soc.* 2010; 2010:3117-20.

Hao S et al., "[Spine disc MR image analysis using improved independent component analysis based active appearance model and Markov random field]." *Sheng Wu Yi Xue Gon Chen Xue Za Zhi.* 2010 February; 27(1):6-9, 15 [Article in Chinese]

Horsfield M A et al., "Rapid semi-automatic segmentation of the spinal cord from magnetic resonance images: application in multiple sclerosis." *Neuroimage.* 2010 Apr. 1; 50(2): 446-55.

Bechara B P et al., "Application of a semiautomated contour segmentation tool to identify the intervertebral nucleus pulposus in MR images." *AJNR Am J Neuroradiol.* 2010 October; 31(9):1640-4.

Ben Ayed I et al., "Graph cuts with invariant object-interaction priors: application to intervertebral disc segmentation." *Inf Process Med Imaging,* 2011; 22:221-32.

Dalca A et al., "Segmentation of nerve bundles and ganglia in spine MRI using particle filters." *Med Image Comput Comput Assist Interv.* 2011; 14(Pt 3):537-45.

Michopoulou S et. al., "Texture-based quantification of lumbar intervertebral disc degeneration from conventional T2-weighted MRI," *Acta Radiologica* 2011; 52: 91-98.

Neubert A, "Automated 3D Segmentation of Vertebral Bodies and Intervertebral Discs from MRI," 2011 International Conference on Digital Image Computing: Techniques and Applications.

Strickland C G et al., "Development of subject-specific geometric spine model through use of automated active contour segmentation and kinematic constraint-limited registration." *J Digit Imaging.* 2011 October; 24(5):926-42.

Giulietti G et al., "Semiautomated segmentation of the human spine based on echoplanar images," *Magn Reson Imaging,* 2011 December; 29(10):1429-36.

Stern D et al., "Parametric modelling and segmentation of vertebral bodies in 3D CT and MR spine images." *Phys Med Biol.* 2011 Dec. 7; 56(23):7505-22.

Neubert A et. al., "Automated detection, 3D segmentation and analysis of high resolution spine MR images using statistical shape models." *Phys Med Biol.* 2012 Dec. 21; 57(24): 8357-76. Egger J et al., "Square-cut: a segmentation algorithm on the basis of a rectangle shape." *PLoS One.* 2012; 7(2).

Vrtovec T et al., "Automated curved planar reformation of 3D spine images." *Phys Med Biol.* 2005 Oct. 7; 50(19):4527-40.

As would be apparent to one of ordinary skill, combinations and sub-combinations between the disclosed aspects, modes, embodiments, features, and variations of references that are incorporated hereunder by reference thereto, and the various aspects, modes, embodiments, features, and variations shown and/or described in the present disclosure, are further contemplated as part of and falling with the intended scope of this disclosure.

It is to be appreciated that the foregoing description provides many details with respect to the embodiments shown and/or described. The specific details disclosed are intended to provide one of ordinary skill sufficient detailed examples to gain a full and complete understanding of the broader aspects of the present disclosure. While considered highly beneficial and illustrative of useful specific applications of the broader aspects contemplated hereunder, such details however are not intended to be necessarily limiting to such broader aspects, as would be apparent to one of ordinary skill. The present disclosure describes various features, no single one of which is solely responsible for the benefits described herein. It will be understood that various features described herein may be combined, modified, or omitted, as would be apparent to on of ordinary skill.

The present description provides for an automated voxelation system and method useful for providing voxels (e.g., for single voxel MRS exams), with particular application described for lumbar intervertebral disc nuclei. However, the broad aspects may be applied to other specific applications without departing from the broad intended scope hereof, such as larger disc volumes to include annulus (often becoming less distinguished from nuclei in degenerative discs), other disc levels along the spine, or other structures of the body where single voxel MRS might be performed. Also, the methods and systems described herein can be used in connection with multivoxel MRS exams.

Although many of the methods and systems described herein are described as using sagittal images to form a voxel, or to model a ROI, or otherwise provide information relating to a ROI, in some embodiments, coronal or axial (or oblique axial) images can also be used. For example a series of coronal plane slices can be used to create a 3D voxel, for example, by creating 2D voxel shapes for the coronal images, modifying the 2D voxel shapes as needed to remain in the ROI, and defining a voxel length (in the y-axis) from the distance covered by the series of coronal images. Other methods disclosed herein can also be modified to use coronal or axial (or oblique axial) images where sagittal images are described.

Furthermore, it is also contemplated that the various specific approaches taken among the various methods herein described for the specific application of automated voxelation also have other beneficial uses than only in such overall system and method. For example, the current disclosure describes a system and method for automatically estimating the location, shape, and volume of intervertebral disc nuclei based on MRI images from an otherwise standard MRI exam. While this can be beneficial for further use in the additional automated voxelation approaches further developed in these detailed embodiments, this approach and result alone is considered an independent, beneficial aspect of the present disclosure, with many beneficial uses contemplated. For example, such result may be applied as useful for other MR-based exams and pulse sequences, such as for example estimating T1 or T2 signal intensities, T1-rho data, etc. for the defined ROI.

Similarly, the voxelated results of the disclosure may be used for other applications than merely MRS, such as immediately described above. By assigning a voxel to MRS data and also to other data acquired for the same region but using a different MR modality, certain benefits may arise from such combination. For example, MRS and T1-rho values can both be taken for the same ROI or voxel, such as for example in a complex multi-pulse sequence exam of disc chemistry, which may be algorithmically diagnostically useful, such as for example in calibrating an MRS curve based on NAA/proteoglycan peak region calibration against T1-rho-based calculations for the same. In yet a further example of other contemplated applications of various disclosed aspects, the ability to automatically and accurately calculate disc angle, disc height, and other tissue structure-related aspects are considered of broad value and application, beyond only the specific further embodiments to which such accomplishments are put in the examples provided herein.

In some embodiments, the location of the disc (e.g., the center of the disc nucleus) and the orientation of the disc (e.g., the angle of tilt) can be automatically identified as described herein and can be used to facilitate the prescription of clinical MRI imaging sequences in the sagittal, coronal, and axial or oblique axial directions. The location and orientation of the disc can be used to prescribe the location and orientation for MRI image slices to be used in clinical analysis. This can be particularly advantageous in the axial or oblique axial orientation where the angle of disc tilt can vary significantly between discs and between patients.

Still further, the approaches taken in the current embodiments may be modified by one of ordinary skill without departing from the scope of the broadly intended aspects of this disclosure. For example, one or more edge detection algorithms (e.g. contrast based, filter assisted, etc.) may be used to estimate the location and dimensions of the vertebral body end-plates bordering above and below discs, to facilitate exclusion of the end-plates from a disc voxelation and MRS exam. These perimeter structures may themselves be estimated to prescribe a perimeter around a disc, from the "outside-in" approach, and in which a voxel prescription is then optimized. Thus, in some embodiments, the methods and systems described herein can identify a population of pixels associated with a structure adjacent the ROI or otherwise useful in determining the location of the ROI. A model of the ROI and/or a voxel defining a scan area can then be created in a manner similar to the descriptions above but wherein the populations of pixels are used to define the ROI from the "outside-in" approach instead of defining the ROI directly. In some embodiments, the anterior and posterior borders are less defined than the superior and inferior end-plates (which are typically well defined via T1 and/or T2 MRI contrast). The system can automatically connect the anterior and posterior ends of the curvilinear estimated lines for the superior and inferior end-plates to define the anterior and posterior borders to appropriately encapsulate the disc in at least many cases, if not nearly all cases with only fringe exceptions. This is one example of another viable approach different than certain specific approaches shown and described herein by reference to the detailed illustrative embodiments and figures, yet are considered within the scope contemplated herein and representative of the broad intended aspects of this disclosure.

While the present description is primarily directed toward automated voxelation systems and methods, it is also to be appreciated that such disclosure may be applied in whole or in part as to the embodiments described, and thus provide for more fully or only partial automation of the voxelation, or related image reconstruction, or region of interest estimation processes. Provisions for certain aspects to be automated, and certain aspects to be manual, may be made. For example, a user/operator technician can click on estimated centers of disc levels intended to be voxelated in order to indicate their general location relative to the field of view in the image. Such manual operations can either replace some of the automated estimation operations provided herein (e.g., replacing the use of empirically derived default ellipsoid search areas), or may rather enhance the likelihood of accurate results (e.g., to better refine the locations at or by which to apply the other estimation algorithms). Moreover, manual overrides may be provided, at operator option. For example, after automated voxelation, the users may be permitted to re-prescribe or modify the automated result based on their own observations, and/or knowledge of patient movement. In some cases the result of the automated voxelation can be automatically flagged for manual adjustment or inspection, as described herein. For example, if a potential source of error is observed by the automated system, the system may prompt the user to inspect or modify the automatically generated voxel. In these regards, the interim operations taken by the automation system may be made invisible to the operator, or all or various operations may be made available to user for review, which may aid in interpreting results. In some cases the operations can be made available to a reviewer of the results after completion of the voxelation or MRS exam report.

In some embodiments, the system can perform a post-acquisition scan for validation that the subject did not move during the MRS data acquisition. The system can automatically locate the targeted disc after the MRS data acquisition and compare that post-acquisition position to the pre-acquisition position to determine if the voxel prescription remains valid after the data acquisition. In some embodiments, the post-acquisition scan can be faster than the initial scan. For example, in some cases only a limited area is scanned that is near the original position of the disc. In some embodiments, only a post-acquisition mid-sagittal scan is compared to the pre-acquisition mid-sagittal scan to assess patient movement. In some cases, the post-acquisition disc location can be identified similarly as described above in connection with the pre-acquisition scan, and the coordinates of the pre and post-acquisition scans can be compared and the acquisition can be deemed invalid if the difference is greater than a threshold value.

The present disclosure describes various features, no single one of which is solely responsible for the benefits described herein. It will be understood that various features described herein may be combined, modified, or omitted, as would be apparent to one of ordinary skill. Other combinations and sub-combinations than those specifically described herein will be apparent to one of ordinary skill, and are intended to form a part of this disclosure. Various methods are described herein in connection with various flowchart steps and/or phases. It will be understood that in many cases, certain steps and/or phases may be combined together such that multiple steps and/or phases shown in the flowcharts can be performed as a single step and/or phase. Also, certain steps and/or phases can be broken into additional sub-components to be performed separately. In some instances, the order of the steps and/or phases can be rearranged and certain steps and/or phases may be omitted entirely. Also, the methods described herein are to be understood to be open-ended, such that additional steps and/or phases to those shown and described herein can also be performed.

Some aspects of the systems and methods described herein can advantageously be implemented using, for example, computer software, hardware, firmware, or any combination of computer software, hardware, and firmware. Computer software can comprise computer executable code stored in a computer readable medium (e.g., non-transitory computer readable medium) that, when executed, performs the functions described herein. In some embodiments, computer-executable code is executed by one or more general purpose computer processors. A skilled artisan will appreciate, in light of this disclosure, that any feature or function that can be implemented using software to be executed on a general purpose computer can also be implemented using a different combination of hardware, software, or firmware. For example, such a module can be implemented completely in hardware using a combination of integrated circuits. Alternatively or additionally, such a feature or function can be implemented completely or partially using specialized computers designed to perform the particular functions described herein rather than by general purpose computers.

Multiple distributed computing devices can be substituted for any one computing device described herein. In such distributed embodiments, the functions of the one computing device are distributed (e.g., over a network) such that some functions are performed on each of the distributed computing devices.

Some embodiments may be described with reference to equations, algorithms, and/or flowchart illustrations. These methods may be implemented using computer program instructions executable on one or more computers. These methods may also be implemented as computer program products either separately, or as a component of an apparatus or system. In this regard, each equation, algorithm, block, or step of a flowchart, and combinations thereof, may be implemented by hardware, firmware, and/or software including one or more computer program instructions embodied in computer-readable program code logic. As will be appreciated, any such computer program instructions may be loaded onto one or more computers, including without limitation a general purpose computer or special purpose computer, or other programmable processing apparatus to produce a machine, such that the computer program instructions which execute on the computer(s) or other programmable processing device(s) implement the functions specified in the equations, algorithms, and/or flowcharts. It will also be understood that each equation, algorithm, and/or block in flowchart illustrations, and combinations thereof, may be implemented by special purpose hardware-based computer systems which perform the specified functions or steps, or combinations of special purpose hardware and computer-readable program code logic means.

Furthermore, computer program instructions, such as embodied in computer-readable program code logic, may also be stored in a computer readable memory (e.g., a non-transitory computer readable medium) that can direct one or more computers or other programmable processing devices to function in a particular manner, such that the instructions stored in the computer-readable memory implement the function(s) specified in the block(s) of the flowchart(s). The computer program instructions may also be loaded onto one or more computers or other programmable computing devices to cause a series of operational steps to be performed on the one or more computers or other programmable computing devices to produce a computer-implemented process such that the instructions which execute on the computer or other programmable processing apparatus provide steps for implementing the functions specified in the equation (s), algorithm(s), and/or block(s) of the flowchart(s).

All of the methods and tasks described herein may be performed and fully automated by a computer system. The computer system may, in some cases, include multiple distinct computers or computing devices (e.g., physical servers, workstations, storage arrays, etc.) that communicate and interoperate over a network to perform the described functions. Each such computing device typically includes a processor (or multiple processors) that executes program instructions or modules stored in a memory or other non-transitory computer-readable storage medium or device. The various functions disclosed herein may be embodied in such program instructions, although some or all of the disclosed functions may alternatively be implemented in application-specific circuitry (e.g., ASICs or FPGAs) of the computer system. Where the computer system includes multiple computing devices, these devices may, but need not, be co-located. The results of the disclosed methods and tasks may be persistently stored by transforming physical storage devices, such as solid state memory chips and/or magnetic disks, into a different state.

What is claimed is:

1. One or more non-transitory computer readable media comprising computer instructions configured to cause one or more computer processors to perform actions comprising:
   accessing a plurality of electronic magnetic resonance imaging (MRI) images of an area that includes a region of interest in an intervertebral disc of a spine;
   for each of the plurality of electronic MRI images:
      processing the electronic MRI image to emphasize pixels associated with two opposite borders between the intervertebral disc and two superiorly and inferiorly adjacent vertebral bodies, respectively;

identifying a population of pixels in the electronic MRI image associated with the borders; and fitting a two dimensional rectilinear shape inside a cross-section of the region of interest in the intervertebral disc and between the borders shown by the electronic MRI image based on the population of pixels; and generating world coordinates that define a three dimensional selected volume comprising a voxel that fits inside of the region of interest in the intervertebral disc and excludes the two superiorly and inferiorly adjacent vertebral bodies associated with the borders based on one or more of the two dimensional rectilinear shapes;

wherein the one or more non-transitory computer readable media are configured to be used with a magnetic resonance spectroscopy (MRS) system in communication with the one or more computer processors, and the MRS system is configured to provide an MRS spectrum of chemical constituents within the voxel.

2. The non-transitory computer readable media of claim 1, further comprising calculating a two dimensional model that approximates the region of interest based on the population of pixels.

3. The non-transitory computer readable media of claim 2, wherein calculating the two dimensional model comprises applying an expectation maximization algorithm for estimating parameters of one or more Gaussian distributions for of the population of pixels.

4. The non-transitory computer readable media of claim 2, wherein the computer instructions are configured to cause the one or more computer processors to orient the two dimensional rectilinear shape based on the orientation of the two dimensional model.

5. The non-transitory computer readable media of claim 4, wherein the two dimensional model comprises an ellipsoid shape having a semi-major axis and a semi-minor axis, and wherein the two dimensional rectilinear shape comprises a rectangle having a length and a width that are oriented based on the orientation of the semi-major axis and/or the semi-minor axis of the ellipsoid shape.

6. The non-transitory computer readable media of claim 1, wherein the computer instructions are further configured to cause the one or more computer processors to output information relating to the region of interest based on the world coordinates, the information comprising one or more of a location, an orientation, a shape, an area, and a volume of the region of interest.

7. The non-transitory computer readable media of claim 1, wherein the plurality of electronic MRI images are of slices substantially parallel to, and spaced apart from, each other.

8. The non-transitory computer readable media of claim 1, wherein the computer instructions are further configured to cause the one or more computer processors to analyze a post-acquisition scan to determine whether the region of interest moved during an MRS acquisition.

9. The non-transitory computer readable media of claim 1, wherein the region of interest comprises a nucleus of the intervertebral disc of the spine.

10. The non-transitory computer readable media of claim 1, wherein the computer instructions are configured to cause the one or more computer processors to analyze the MRS spectrum and to determine whether the three dimensional selected volume was likely mis-prescribed based on one or more signals.

11. The non-transitory computer readable media of claim 10, wherein the one or more signals comprise a lipid signal.

12. The non-transitory computer readable media of claim 1, wherein the computer instructions are configured to provide a single three dimensional scan volume to the MRS system configured for single voxel MRS.

13. The non-transitory computer readable media of claim 1, wherein the computer instructions are configured to cause the one or more computer processors to select multiple three dimensional volumes corresponding to multiple regions of interest and to provide the multiple three dimensional volumes to the MRS system.

14. The non-transitory computer readable media of claim 1, wherein the electronic MRI images are of a first acquisition mode, and wherein the MRS spectrum is of a second acquisition mode different than the first acquisition mode.

15. The non-transitory computer readable media of claim 1, wherein the three dimensional selected volume is a rectilinear volume.

16. The non-transitory computer readable media of claim 1, wherein the borders comprise vertebral body end-plates between the intervertebral disc and the adjacent vertebral bodies.

17. The non-transitory computer readable media of claim 1, wherein the computer instructions are configured to cause the one or more computer processors to perform operations comprising:

generating world coordinates that define a first three dimensional selected volume that fits inside of the region of interest in the intervertebral disc;

generating world coordinates that define a second three dimensional selected volume that fits inside of the region of interest in the intervertebral disc based on a different number of the electronic MRI images than used for generating the first three dimensional selected volume;

calculating a volume of the first three dimensional selected volume;

calculating a volume of the second three dimensional selected volume; and selecting as the voxel the one of the first three dimensional selected volume and the second three dimensional selected volume that has the larger volume.

18. The non-transitory computer readable media of claim 1, wherein one or more of the plurality of electronic MRI images are disregarded when generating the world coordinates that define the three dimensional selected volume.

19. The non-transitory computer readable media of claim 1, wherein the three dimensional selected volume is fit within an inward offset from the borders.

* * * * *